US006753158B1

(12) United States Patent
Jackson et al.

(10) Patent No.: US 6,753,158 B1
(45) Date of Patent: Jun. 22, 2004

(54) ASSAYS, AGENTS, THERAPY AND DIAGNOSIS RELATING TO MODULATION OF CELLULAR DNA REPAIR ACTIVITY

(75) Inventors: Stephen Philip Jackson, Cambridge (GB); Susan Elizabeth Critchlow, Cambridge (GB)

(73) Assignee: Kudos Pharmaceuticals Limited, Cambridge (GB)

( * ) Notice: Subject to any disclaimer, the term of this patent is extended or adjusted under 35 U.S.C. 154(b) by 0 days.

(21) Appl. No.: 09/341,505

(22) PCT Filed: Jan. 13, 1998

(86) PCT No.: PCT/GB98/00095

§ 371 (c)(1),
(2), (4) Date: Jul. 12, 1999

(87) PCT Pub. No.: WO98/30902

PCT Pub. Date: Jul. 16, 1998

(30) Foreign Application Priority Data

Jan. 13, 1997 (GB) ................................................ 9700574
Jun. 20, 1997 (GB) ................................................ 9713131

(51) Int. Cl.$^7$ ......................... A61K 38/53; G01N 33/53; G01N 33/50
(52) U.S. Cl. ......................... 435/7.6; 435/7.1; 424/94.5; 514/2; 514/12; 530/350; 530/352
(58) Field of Search ...................... 435/7.1, 7.6, 320.1, 435/325, 6, 194, 354, 455, 440; 530/350, 352, 300; 514/2, 12, 44; 424/94.5; 536/23.1; 800/18

(56) References Cited

FOREIGN PATENT DOCUMENTS

| WO | 94 17189 | 8/1994 |
|---|---|---|
| WO | 95/10288 A | 4/1995 |
| WO | 96 30524 A | 10/1996 |

OTHER PUBLICATIONS

Chen, L. et al. (2000) Interactions of the DNA ligase IV–XRCC4 complex with DNA ends and the DNA–dependent protein kinas J Biol Chem. vol. 275, pp. 26196–26205.*
McElhinny, S. A. N. et al. (2000) Ku recruits the XRCC4–ligase IV complex to DNA ends. Mol Cell Biol. vol. 20, pp. 2996–3003.*
Grawunder, U. et al. (1997) Activity of DNA ligase IV stimulated by complex formation with XRCC4 protein in mammalian cells. Nature. 1997 vol. 388, pp. 492–495.*
Vaeshavsky, V. (1996) The N–end rule: functions, mysteries, uses. Proc Natl Sci U S A. vol. 29, pp. 12142–14149.*
Zhiying et al., Cell, vol. 83, pp. 1079–1089, Dec. 1995.*
Hartley et al., Cell, vol. 82, pp. 849–856, Sep. 1995.*
Critchlow, S. E. et al., "Mammalian Double Strand Break repair Protein XRCC4 Interacts With DNA Ligase IV," Current Biology (Aug. 1997) vol. 7, No. (8):588–598.

(List continued on next page.)

*Primary Examiner*—Christopher S. F. Low
*Assistant Examiner*—Samuel W. Liu
(74) *Attorney, Agent, or Firm*—Pamela J. Sherwood; Bozicevic, Field & Francis LLP

(57) ABSTRACT

A yeast homologue of mammalian DNA ligase IV is provided and a role for DNA ligase IV established in the Ku-associated DNA repair pathway. Additionally interactions between DNA ligase IV and XRCC4, and interaction between XRCC4 and DNA-PKcs/Ku are established, providing for assays for agents which modulate such interactions and therefore cellular DNA repair activity. Such agents are useful in treatment of cancers, retroviral infections, immune system disorders and other conditions in which cellular DNA repair activity plays a role. Individuals with a predisposition to a disorder in which DNA repair plays a role may be diagnosed, by screening for the presence or absence of a defect in XRCC4 and/or DNA ligase IV activity.

3 Claims, 11 Drawing Sheets

OTHER PUBLICATIONS

Gaken, Joop, et al., "Efficient Retroviral Infection Of Mammalian Cells Is Blocked By Inhibition Of Poly(ADP–Ribose) Polymerase Activity," *J. Virol.* (1996) vol. 70, No. (6):3992–4000.

Grawunder, U., et al., "Activity Of DNA Ligase IV Stimulated By Complex Formation With XRCC4 Protein In Mammalian Cells," *Nature* (Jul. 1997) vol. 388:492–495.

Hartley, K., et al., "DNA–Dependent Protein Kinase Catalytic Subunit: A Relative Of Phosphatidylinositol 3–Kinase And The Ataxia Telangiectasia Gene Product," *Cell* (Sep. 1995) vol. 82, No. (8):849–856.

Hidaka, H. et al., "Methods In Enzymology ," vol. 201; Protein Phosphorylation Part B Analysis Of Protein Phosphorylation, Protein Kinase Inhibitors And Protein Phosphatases; Ed, T. Hunter and B.M. Sefton; Chapter 27: "Properties And Use Of H–Series Compounds As Protein Kinase Inhibiotrs," 1991, Academic Press, San Diego, pp:328–339.

Kaczmarski, Wojciech, et al., "Lupus Autoantigen Ku Protein Binds HIV–1 TAR RNA In Vitro," *Biochem Biosphys. Res. Commun.* (1993) vol. 196, No. (2):935–42.

Poltoratsky, V.P., et al., "Human DNA Activated Protein Kinase (DNA–PK) Is Homologous To Phosphatidylinositol Kinase," *The Journal Of Immunology* (1995) vol. 155:4529–4533.

Salles, B. et al., "Rapid Quantification Of DNA Repair Synthesis In Cell Extracts," *Analytical Biochemistry* (1993) vol. 215:304–306.

Tomkinson, A.E., et al., "Structure And Function Of Mammalian DNA Ligases," *Mutat. Res.* (Jan. 1998) vol. 407, No. (1):1–9.

Wei, Y.F., et al., "Molecular Cloning And Expression Of Human cDNAs encoding A Novel DNA Ligase IV And DNA Ligase III, An Enzyme Active In DNA Repair And Recombination," *Molecular And Cellular Biology* (Jun. 1995) vol. 15, No. (6):3206–3216.

Grawunder et al. (1998). "DNA Ligase IV Binds to XRCC4 via a Motif Lacated Between rather Than Within its BRCT Domains," *Current Biology*, vol. 8(15):873–873.

* cited by examiner

Figure 2

Fig.4.
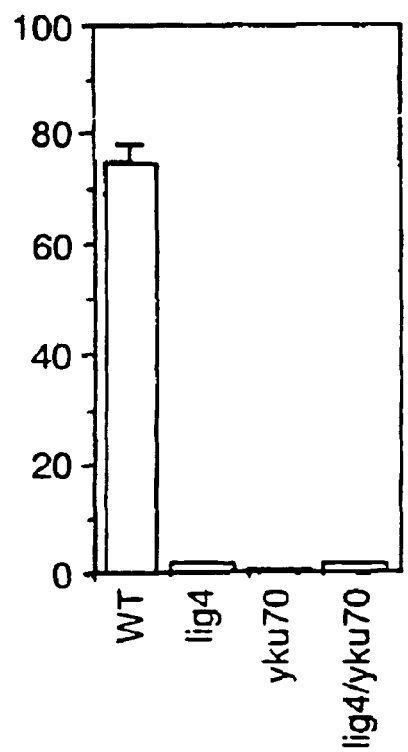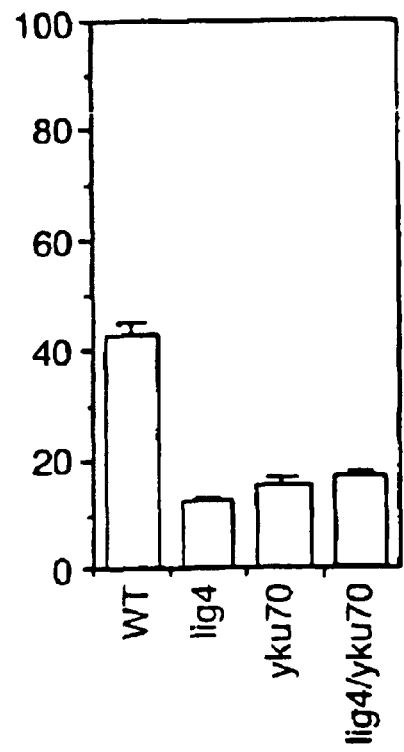

Figure 6

```
     GTGATTAAATAGGCTGAAATCAGTGTTTAGTAACTACGTACGTTGTACATGTAACATTGT
  1  ------------+---------+---------+---------+---------+---------+  60
     CACTAATTTATCCGACTTTAGTCACAAATCATTGATGCATGCAACATGTACATTGTAACA

V  I  K  *  A  E  I  S  V  *  *  L  R  T  L  Y  M  *  H  C  -

GATATAAATCGTAAGATTCGCCGAGTATAGATCAATAATATCGGTTTCATCACTTACGTT
 61  ------------+---------+---------+---------+---------+---------+  120
     CTATATTTAGCATTCTAAGCGGCTCATATCTAGTTATTATAGCCAAAGTAGTGAATGCAA

D  I  N  R  K  I  R  R  V  *  I  N  N  I  G  F  I  T  Y  V  -

GTTTGTGCAGTACTAGAGTTAAGATCGTTTTCGATCCCTTATTTTCTTCTTTTTTCCTTT
121  ------------+---------+---------+---------+---------+---------+  180
     CAAACACGTCATGATCTCAATTCTAGCAAAAGCTAGGGAATAAAAGAAGAAAAAAGGAAA

V  C  A  V  L  E  R  S  F  S  I  P  Y  F  L  L  F  S  F  -

TTTTTGTTATTTTTCTCTTTTTACCTTTTGTCACCATATTAAATCTTTAAACAAATCTAA
181  ------------+---------+---------+---------+---------+---------+  240
     AAAAACAATAAAAAGAGAAAAATGGAAAACAGTGGTATAATTTAGAAATTTGTTTAGATT

F  L  L  F  F  S  F  Y  L  L  S  P  Y  *  I  F  K  Q  I  *  -

CTATGAAAAAATCCTTTAAACATATGTTAATATGTGGAAAATAAATACTAAAATAAAAAT
241  ------------+---------+---------+---------+---------+---------+  300
     GATACTTTTTTAGGAAATTTGTATACAATTATACACCTTTTATTTATGATTTTATTTTTA

L  *  K  N  P  L  N  I  C  *  Y  V  E  N  K  Y  *  N  K  N  -

CTAGAACTGAAGGAAATAGTAACGGATTATTTAGGTATGATATCAGCACTAGATTCTATA
301  ------------+---------+---------+---------+---------+---------+  360
     GATCTTGACTTCCTTTATCATTGCCTAATAAATCCATACTATAGTCGTGATCTAAGATAT

L  E  L  K  E  I  V  T  D  Y  L  G  M  I  S  A  L  D  S  I  -

CCCGAGCCCCAAAACTTTGCGCCTAGTCCAGATTTCAAATGGCTTTGTGAAGAGCTATTT
361  ------------+---------+---------+---------+---------+---------+  420
     GGGCTCGGGGTTTTGAAACGCGGATCAGGTCTAAAGTTTACCGAAACACTTCTCGATAAA

P  E  P  Q  N  F  A  P  S  P  D  F  K  W  L  C  E  E  L  F  -

GTGAAGATACATGAAGTTCAAATTAATGGAACGGCCGGCACTGGCAAATCAAGGTCTTTC
421  ------------+---------+---------+---------+---------+---------+  480
     CACTTCTATGTACTTCAAGTTTAATTACCTTGCCGGCCGTGACCGTTTAGTTCCAGAAAG

V  K  I  H  E  V  Q  I  N  G  T  A  G  T  G  K  S  R  S  F  -

AAGTACTATGAAATAATATCGAATTTCGTCGAAATGTGGAGAAAAACCGTGGGAAATAAT
481  ------------+---------+---------+---------+---------+---------+  540
     TTCATGATACTTTATTATAGCTTAAAGCAGCTTTACACCTCTTTTTGGCACCCTTTATTA

K  Y  Y  E  I  I  S  N  F  V  E  M  W  R  K  T  V  G  N  N  -

ATATATCCTGCACTGGTTCTTGCTCTTCCCTACCGCGATAGACGAATCTATAATATTAAG
541  ------------+---------+---------+---------+---------+---------+  600
     TATATAGGACGTGACCAAGAACGAGAAGGGATGGCGCTATCTGCTTAGATATTATAATTC

```
      GATTATGTATTAATAAGAACTATATGCTCTTACTTGAAGTTGCCAAAAAATTCTGCAACA
 601  ---------+---------+---------+---------+---------+---------+ 660
      CTAATACATAATTATTCTTGATATACGAGAATGAACTTCAACGGTTTTTTAAGACGTTGT

D  Y  V  L  I  R  T  I  C  S  Y  L  K  L  P  K  N  S  A  T  -

GAGCAGCGGTTAAAAGATTGGAAACAGCGTGTCGGTAAAGGTGGGAATCTTTCTTCTCTT
 661  ---------+---------+---------+---------+---------+---------+ 720
      CTCGTCGCCAATTTTCTAACCTTTGTCGCACAGCCATTTCCACCCTTAGAAAGAAGAGAA

E  Q  R  L  K  D  W  K  Q  R  V  G  K  G  G  N  L  S  S  L  -

CTTGTGGAAGAAATTGCTAAAAGAAGGGCTGAACCTAGCTCAAAAGCGATTACAATTGAT
 721  ---------+---------+---------+---------+---------+---------+ 780
      GAACACCTTCTTTAACGATTTTCTTCCCGACTTGGATCGAGTTTTCGCTAATGTTAACTA

L  V  E  E  I  A  K  R  R  A  E  P  S  S  K  A  I  T  I  D  -

AACGTCAATCACTATCTGGATAGTTTGAGTGGAGACAGGTTCGCTTCCGGACGAGGATTT
 781  ---------+---------+---------+---------+---------+---------+ 840
      TTGCAGTTAGTGATAGACCTATCAAACTCACCTCTGTCCAAGCGAAGGCCTGCTCCTAAA

N  V  N  H  Y  L  D  S  L  S  G  D  R  F  A  S  G  R  G  F  -

AAGAGTCTTGTCAAGTCCAAACCTTTCCTGCACTGTGTGGAGAATATGAGTTTCGTCGAA
 841  ---------+---------+---------+---------+---------+---------+ 900
      TTCTCAGAACAGTTCAGGTTTGGAAAGGACGTGACACACCTCTTATACTCAAAGCAGCTT

K  S  L  V  K  S  K  P  F  L  H  C  V  E  N  M  S  F  V  E  -

TTAAAATACTTCTTTGATATCGTGCTTAAAAATAGAGTAATAGGAGGTCAAGAGCACAAA
 901  ---------+---------+---------+---------+---------+---------+ 960
      AATTTTATGAAGAAACTATAGCACGAATTTTTATCTCATTATCCTCCAGTTCTCGTGTTT

L  K  Y  F  F  D  I  V  L  K  N  R  V  I  G  G  Q  E  H  K  -

TTGCTAAACTGCTGGCATCCTGATGCTCAGGATTATCTTAGCGTGATATCTGATTTAAAG
 961  ---------+---------+---------+---------+---------+---------+ 1020
      AACGATTTGACGACCGTAGGACTACGAGTCCTAATAGAATCGCACTATAGACTAAATTTC

L  L  N  C  W  H  P  D  A  Q  D  Y  L  S  V  I  S  D  L  K  -

GTGGTAACTTCAAAACTTTATGATCCAAAAGTTCGTCTAAAGGATGATGATTTGAGTATA
1021  ---------+---------+---------+---------+---------+---------+ 1080
      CACCATTGAAGTTTTGAAATACTAGGTTTTCAAGCAGATTTCCTACTACTAAACTCATAT

V  V  T  S  K  L  Y  D  P  K  V  R  L  K  D  D  D  L  S  I  -

AAAGTTGGCTTTGCATTCGCCCCCCAATTAGCCAAAAAAGTGAATCTTTCTTATGAGAAA
1081  ---------+---------+---------+---------+---------+---------+ 1140
      TTTCAACCGAAACGTAAGCGGGGGGTTAATCGGTTTTTTCACTTAGAAAGAATACTCTTT

K  V  G  F  A  F  A  P  Q  L  A  K  K  V  N  L  S  Y  E  K  -

ATATGCCGTACACTACATGATGATTTTTTTGGTAGAAGAAAAAATGGATGGAGAACGAATT
1141  ---------+---------+---------+---------+---------+---------+ 1200
      TATACGGCATGTGATGTACTACTAAAAAACCATCTTCTTTTTTACCTACCTCTTGCTTAA

I  C  R  T  L  H  D  D  F  L  V  E  E  K  M  D  G  E  R  I  -

CAAGTTCATTATATGAATTATGGTGAATCCATAAAATTTTTTAGTAGACGGGGCATCGAC
1201  ---------+---------+---------+---------+---------+---------+ 1260
      GTTCAAGTAATATACTTAATACCACTTAGGTATTTTAAAAAATCATCTGCCCCGTAGCTG

```
       TATACCTATTTGTACGGAGCGAGCTTATCATCAGGAACTATATCTCAACATTTGAGGTTT
1261   ------------+---------+---------+---------+---------+---------+  1320
       ATATGGATAAACATGCCTCGCTCGAATAGTAGTCCTTGATATAGAGTTGTAAACTCCAAA

Y  T  Y  L  Y  G  A  S  L  S  S  G  T  I  S  Q  H  L  R  F   -

ACAGATAGTGTTAAAGAATGTGTTTTAGATGGAGAAATGGTGACGTTTGATGCAAAAAGA
1321   ------------+---------+---------+---------+---------+---------+  1380
       TGTCTATCACAATTTCTTACACAAAATCTACCTCTTTACCACTGCAAACTACGTTTTTCT

T  D  S  V  K  E  C  V  L  D  G  E  M  V  T  F  D  A  K  R   -

CGGGTGATTCTTCCATTCGGTCTTGTTAAAGGAAGTGCAAAGGAAGCGCTATCTTTTAAT
1381   ------------+---------+---------+---------+---------+---------+  1440
       GCCCACTAAGAAGGTAAGCCAGAACAATTTCCTTCACGTTTCCTTCGCGATAGAAAATTA

R  V  I  L  P  F  G  L  V  K  G  S  A  K  E  A  L  S  F  N   -

AGTATAAATAATGTTGACTTTCACCCCTTATATATGGTGTTTGATCTGTTATACCTGAAT
1441   ------------+---------+---------+---------+---------+---------+  1500
       TCATATTTATTACAACTGAAAGTGGGGAATATATACCACAAACTAGACAATATGGACTTA

S  I  N  N  V  D  F  H  P  L  Y  M  V  F  D  L  L  Y  L  N   -

GGGACTTCGTTGACACCATTACCCCTTCATCAAAGGAAGCAATATCTGAACAGCATTTTA
1501   ------------+---------+---------+---------+---------+---------+  1560
       CCCTGAAGCAACTGTGGTAATGGGGAAGTAGTTTCCTTCGTTATAGACTTGTCGTAAAAT

G  T  S  L  T  P  L  P  L  H  Q  R  K  Q  Y  L  N  S  I  L   -

AGTCCCTTGAAAAATATTGTAGAAATAGTACGATCTTCTAGATGTTATGGTGTGGAGTCA
1561   ------------+---------+---------+---------+---------+---------+  1620
       TCAGGGAACTTTTTATAACATCTTTATCATGCTAGAAGATCTACAATACCACACCTCAGT

S  P  L  K  N  I  V  E  I  V  R  S  S  R  C  Y  G  V  E  S   -

ATCAAAAAGTCTTTAGAAGTTGCAATCTCACTGGGTTCAGAAGGAGTTGTTTTGAAATAT
1621   ------------+---------+---------+---------+---------+---------+  1680
       TAGTTTTTCAGAAATCTTCAACGTTAGAGTGACCCAAGTCTTCCTCAACAAAACTTTATA

I  K  K  S  L  E  V  A  I  S  L  G  S  E  G  V  V  L  K  Y   -

TATAATTCAAGTTATAATGTCGCCAGTCGAAACAACAACTGGATCAAGGTAAAACCTGAA
1681   ------------+---------+---------+---------+---------+---------+  1740
       ATATTAAGTTCAATATTACAGCGGTCAGCTTTGTTGTTGACCTAGTTCCATTTTGGACTT

Y  N  S  S  Y  N  V  A  S  R  N  N  N  W  I  K  V  K  P  E   -

TATTTGGAGGAATTTGGAGAGAATTTAGACTTAATAGTAATAGGCAGAGATTCTGGGAAA
1741   ------------+---------+---------+---------+---------+---------+  1800
       ATAAACCTCCTTAAACCTCTCTTAAATCTGAATTATCATTATCCGTCTCTAAGACCCTTT

Y  L  E  E  F  G  E  N  L  D  L  I  V  I  G  R  D  S  G  K   -

AAAGATTCTTTTTATGCTAGGGTTACTTGTGCTAGATGAAGAAGAGTATAAAAAGCACCAA
1801   ------------+---------+---------+---------+---------+---------+  1860
       TTTCTAAGAAAATACGATCCCAATGAACACGATCTACTTCTTCTCATATTTTTCGTGGTT

K  D  S  F  M  L  G  L  L  V  L  D  E  E  E  Y  K  K  H  Q   -

GGAGACTCCTCTGAAATTGTAGACCACTCAAGCCAAGAAAAACACATACAAAATTCAAGA
1861   ------------+---------+---------+---------+---------+---------+  1920
       CCTCTGAGGAGACTTTAACATCTGGTGAGTTCGGTTCTTTTTGTGTATGTTTAAGTTCT

G  D  S  S  E  I  V  D  H  S  S  Q  E  K  H  I  Q  N  S  R   -

AGAAGGGTGAAAAAAATACTTTCATTCTGTTCTATCGCAAACGGTATATCTCAAGAAGAA
```

Figure 6 (Continued)

```
1921 ---------+---------+---------+---------+---------+---------+ 1980
     TCTTCCCACTTTTTTTATGAAAGTAAGACAAGATAGCGTTTGCCATATAGAGTTCTTCTT

R  R  V  K  K  I  L  S  F  C  S  I  A  N  G  I  S  Q  E  E   -

TTCAAAGAAATCGACCGCAAAACGAGAGGACATTGGAAAAGAACCTCCGAAGTTGCTCCC
1981 ---------+---------+---------+---------+---------+---------+ 2040
     AAGTTTCTTTAGCTGGCGTTTTGCTCTCCTGTAACCTTTTCTTGGAGGCTTCAACGAGGG

F  K  E  I  D  R  K  T  R  G  H  W  K  R  T  S  E  V  A  P   -

CCTGCTTCAATTTTAGAATTTGGCTCAAAAATACCTGCCGAATGGATTGACCCCAGTGAA
2041 ---------+---------+---------+---------+---------+---------+ 2100
     GGACGAAGTTAAAATCTTAAACCGAGTTTTTATGGACGGCTTACCTAACTGGGGTCACTT

P  A  S  I  L  E  F  G  S  K  I  P  A  E  W  I  D  P  S  E   -

TCAATTGTTCTAGAAATAAAATCACGGTCTTTGGATAACACAGAAACGAATATGCAGAAG
2101 ---------+---------+---------+---------+---------+---------+ 2160
     AGTTAACAAGATCTTTATTTTAGTGCCAGAAACCTATTGTGTCTTTGCTTATACGTCTTC

S  I  V  L  E  I  K  S  R  S  L  D  N  T  E  T  N  M  Q  K   -

TACGCTACCAATTGTACTTTGTACGGTGGCTATTGTAAAAGAATACGGTACGATAAAGAA
2161 ---------+---------+---------+---------+---------+---------+ 2220
     ATGCGATGGTTAACATGAAACATGCCACCGATAACATTTTCTTATGCCATGCTATTTCTT

Y  A  T  N  C  T  L  Y  G  G  Y  C  K  R  I  R  Y  D  K  E   -

TGGACAGATTGTTACACACTTAACGACTTATACGAAAGTAGGACGGTTAAATCTAACCCC
2221 ---------+---------+---------+---------+---------+---------+ 2280
     ACCTGTCTAACAATGTGTGAATTGCTGAATATGCTTTCATCCTGCCAATTTAGATTGGGG

W  T  D  C  Y  T  L  N  D  L  Y  E  S  R  T  V  K  S  N  P   -

AGCTATCAAGCGGAAAGGTCACAGCTTGGATTGATACGGAAAAAGAGAAAGAGAGTACTT
2281 ---------+---------+---------+---------+---------+---------+ 2340
     TCGATAGTTCGCCTTTCCAGTGTCGAACCTAACTATGCCTTTTTCTCTTTCTCTCATGAA

S  Y  Q  A  E  R  S  Q  L  G  L  I  R  K  K  R  K  R  V  L   -

ATTTCAGACAGCTTTCACCAAAACAGGAAACAACTGCCAATTTCAAACATCTTTGCCGGA
2341 ---------+---------+---------+---------+---------+---------+ 2400
     TAAAGTCTGTCGAAAGTGGTTTTGTCCTTTGTTGACGGTTAAAGTTTGTAGAAACGGCCT

I  S  D  S  F  H  Q  N  R  K  Q  L  P  I  S  N  I  F  A  G   -

TTACTTTTTTATGTTCTCTCTGACTATGTCACGGAGGACACTGGAATACGGATTACACGG
2401 ---------+---------+---------+---------+---------+---------+ 2460
     AATGAAAAAATACAAGAGAGACTGATACAGTGCCTCCTGTGACCTTATGCCTAATGTGCC

L  L  F  Y  V  L  S  D  Y  V  T  E  D  T  G  I  R  I  T  R   -

GCAGAACTTGAAAAAACTATTGTGGAACATGGTGGTAAACTGATATATAATGTAATTTTA
2461 ---------+---------+---------+---------+---------+---------+ 2520
     CGTCTTGAACTTTTTTGATAACACCTTGTACCACCATTTGACTATATATTACATTAAAAT

A  E  L  E  K  T  I  V  E  H  G  G  K  L  I  Y  N  V  I  L   -

AAACGTCATTCAATTGGGGACGTTCGGTTAATCAGCTGTAAAACTACCACGGAATGCAAG
2521 ---------+---------+---------+---------+---------+---------+ 2580
     TTTGCAGTAAGTTAACCCCTGCAAGCCAATTAGTCGACATTTTGATGGTGCCTTACGTTC

K  R  H  S  I  G  D  V  R  L  I  S  C  K  T  T  T  E  C  K   -

GCTTTAATAGATCGAGGATATGATATATTGCACCCAAATTGGGTACTCGATTGTATAGCA
2581 ---------+---------+---------+---------+---------+---------+ 2640
```

Figure 6 (Continued)

```
             CGAAATTATCTAGCTCCTATACTATATAACGTGGGTTTAACCCATGAGCTAACATATCGT

A  L  I  D  R  G  Y  D  I  L  H  P  N  W  V  L  D  C  I  A   -
        TATAAGAGGCTCATCCTGATCGAGCCCAATTATTGCTTTAACGTCTCTCAAAAAATGAGA
2641    ---------+---------+---------+---------+---------+---------+ 2700
        ATATTCTCCGAGTAGGACTAGCTCGGGTTAATAACGAAATTGCAGAGAGTTTTTTACTCT

Y  K  R  L  I  L  I  E  P  N  Y  C  F  N  V  S  Q  K  M  R   -
        GCCGTCGCTGAAAAAAGGGTAGATTGTTTGGGTGATAGTTTTGAAAATGACATTTCGGAA
2701    ---------+---------+---------+---------+---------+---------+ 2760
        CGGCAGCGACTTTTTTCCCATCTAACAAACCCACTATCAAAACTTTTACTGTAAAGCCTT

A  V  A  E  K  R  V  D  C  L  G  D  S  F  E  N  D  I  S  E   -
        ACCAAACTGTCATCATTGTATAAATCACAACTAAGTCTACCACCGATGGGGAACTCGAG
2761    ---------+---------+---------+---------+---------+---------+ 2820
        TGGTTTGACAGTAGTAACATATTTAGTGTTGATTCAGATGGTGGCTACCCCCTTGAGCTC

T  K  L  S  S  L  Y  K  S  Q  L  S  L  P  P  M  G  E  L  E   -
        ATAGATTCTGAGGTTCGGCGGTTTCCATTATTTTTATTCTCCAACAGGATTGCATACGTA
2821    ---------+---------+---------+---------+---------+---------+ 2880
        TATCTAAGACTCCAAGCCGCCAAAGGTAATAAAAATAAGAGGTTGTCCTAACGTATGCAT

I  D  S  E  V  R  R  F  P  L  F  L  F  S  N  R  I  A  Y  V   -
        CCACGTCGCAAAATTAGCACAGAAGATGACATTATAGAAATGAAAATTAAGTTGTTTGGT
2881    ---------+---------+---------+---------+---------+---------+ 2940
        GGTGCAGCGTTTTAATCGTGTCTTCTACTGTAATATCTTTACTTTTAATTCAACAAACCA

P  R  R  K  I  S  T  E  D  D  I  I  E  M  K  I  K  L  F  G   -
        GGAAAAATAACAGATCAACAGTCACTTTGTAACTTAATAATTATACCATATACTGATCCT
2941    ---------+---------+---------+---------+---------+---------+ 3000
        CCTTTTTATTGTCTAGTTGTCAGTGAAACATTGAATTATTAATATGGTATATGACTAGGA

G  K  I  T  D  Q  Q  S  L  C  N  L  I  I  I  P  Y  T  D  P   -
        ATTTTGAGGAAAGACTGCATGAATGAGGTACACGAAAAAAATAAAAGAACAAATAAAGGCT
3001    ---------+---------+---------+---------+---------+---------+ 3060
        TAAAACTCCTTTCTGACGTACTTACTCCATGTGCTTTTTTATTTTCTTGTTTATTTCCGA

I  L  R  K  D  C  M  N  E  V  H  E  K  I  K  E  Q  I  K  A   -
        TCTGATACTATACCGAAAATAGCCAGGGTCGTTGCCCCTGAATGGGTGGATCATTCTATT
3061    ---------+---------+---------+---------+---------+---------+ 3120
        AGACTATGATATGGCTTTTATCGGTCCCAGCAACGGGGACTTACCCACCTAGTAAGATAA

S  D  T  I  P  K  I  A  R  V  V  A  P  E  W  V  D  H  S  I   -
        AATGAAAACTGTCAAGTGCCTGAAGAAGACTTCCCCGTAGTCAACTACTGATGGTGCGTT
3121    ---------+---------+---------+---------+---------+---------+ 3180
        TTACTTTTGACAGTTCACGGACTTCTTCTGAAGGGGCATCAGTTGATGACTACCACGCAA

N  E  N  C  Q  V  P  E  E  D  F  P  V  V  N  Y  *  W  C  V   -
        TTGCCGGAGGCTTAATTTTTTGAAGTTTATTTAATACTATCCTACATATGTACATTAAATA
3181    ---------+---------+---------+---------+---------+---------+ 3240
        AACGCCTCCGAATTAAAAAACTTCAAATAAATTATGATAGGATGTATACATGTAATTTAT

L  R  R  L  N  F  L  K  F  I  *  Y  Y  P  T  Y  V  H  *  I   -
        CTTCCGTAACGTTTATCAATAAGAGTGGAAGATGCGCAATTATATTCAAAAGATTGGCCA
3241    ---------+---------+---------+---------+---------+---------+ 3300
        GAAGGCATTGCAAATAGTTATTCTCACCTTCTACGCGTTAATATAAGTTTTCTAACCGGT
```

Figure 6 (Continued)

```
      L  P  *  R  L  S  I  R  V  E  D  A  Q  L  Y  S  K  D  W  P  -
      GTCAATTAACTTAAGGAAAAAAT
3301  -----------+-----------+--- 3323
      CAGTTAATTGAATTCCTTTTTTA

V  N  *  L  K  E  K        -
```

ASSAYS, AGENTS, THERAPY AND DIAGNOSIS RELATING TO MODULATION OF CELLULAR DNA REPAIR ACTIVITY

CROSS-REFERENCE TO RELATED APPLICATIONS

This application is a §371 National Stage filing of International Patent application no. PCT/GB98/00095, filed Jan. 13, 1998, which claims priority to Great Britain application no. GB9700574.8, filed Jan. 13, 1997 and Great Britain patent application no. GB9713131.2, filed Jun. 20, 1997.

The present invention relates to screening methods, peptides, mimetics, and methods of use based on the surprising discovery and characterisation of an interaction between known proteins and the establishment that such interaction plays a key role in DNA repair, and thus numerous cellular processes of interest in therapeutic contexts. Two proteins in question are XRCC4 and DNA ligase IV. Interaction between XRCC4 and DNA-PKcs/Ku is also indicated.

The invention has arisen on the basis of the work of the present inventors establishing for the first time crucial information about XRCC4. Some information was available on the physiological function of this protein, it having been implicated in the Ku-associated DNA double-strand break repair (KADR) apparatus. However, very little was known about its biological activity and what its role in the KADR apparatus actually is. Prior to the making of the present invention it was not feasible to provide assays useful as primary screens for inhibitors of XRCC4.

Furthermore, the inventors' new cloning work has identified a yeast homologue of mammalian DNA ligase IV. No physiological function has previously been assigned to mammalian DNA ligase IV, but the inventors' yeast work, including analysis of the effect of knock-out mutation in yeast, now establishes the physiological relevance of DNA ligase IV and thus provides indication of therapeutic contexts in which modulation of its function can be effected.

The work disclosed herein establishing interaction between XRCC4 and DNA ligase IV, interaction between XRCC4 and DNA-PKcs/Ku, and also a biological role for such interactions, now gives rise to screening methods for identifying compounds which affect the interaction, particularly those which interfere with it, and which may affect or modulate particular aspects of cellular DNA repair activity, useful in a therapeutic context, for example in the treatment of proliferative disorders, cancers and tumours, disorders involving retroviruses such as AIDS, human adult T-cell leukemia/lymphoma, Type I diabetes and multiple sclerosis, and also in radiotherapy. Furthermore it gives rise to the rational design of peptides or mimetics or functional analogues which fulfil this function.

One of the most dangerous forms of damage that can befall a cell is the DNA double-strand break (DSB), which is the principal lethal lesion induced by ionizing radiation and by radiomimetic agents. Consequently, cells have evolved highly effective and complex systems for recognizing this type of DNA damage and ensuring that it is repaired efficiently and accurately. Two major pathways have evolved to repair DNA DSBs in eukaryotes, homologous recombination and DNA non-homologous end-joining (NHEJ).

Much of what is currently known about DNA NHEJ in mammalian systems has been obtained through studies of a series of mutant rodent cell lines that were identified originally as being hypersensitive towards ionizing radiation and which display severe defects in DNA DSB repair (reviewed in Jeggo et al., 1995; Roth et al., 1995). Characterisation of these cell lines has revealed that they fall into three complementation groups, termed. IR4, IR5 and IR7. The hamster cell line XR-1 defines IR4, IR5 consists of a number of independently isolated hamster cell mutants, and IR7 contains the hamster cell line V3 and cells derived from the severe combined immune-deficient (scid) mouse. Various studies have shown that IR4, IR5 and IR5 cells are defective in antibody and T-cell receptor V(D)J recombination.

Considerable effort has been directed towards establishing the nature of the gene-products defective in cells of IR4, IR5 and IR7, and determining how they function in DNA NHEJ. As a result of such studies, it was shown that cells of IR5 and IR7 are deficient in components of the DNA-dependent protein kinase (DNA-PK) (Ku80 and DNA-PKcs, respectively). DNA-PK is a nuclear protein Ser/Thr kinase that displays the unusual property of being activated upon binding to DNA DSBs or other perturbations of the DNA double-helix (Jackson, 1997). In light of the biochemical properties of DNA-PK which have been established, an attractive hypothesis is that this enzyme serves as a DNA damage sensor in vivo.

In contrast to cells of IR5 and IR7, XR-1 cells of IR4 are not deficient in a DNA-PK component, as evidenced by the fact that extracts of these cells have normal DNA end-binding activity (Getts and Stamato, 1994; Rathmell and Chu, 1994; Finnie et al., 1996) and DNA-PK activity (Blunt et al., 1995), and that expression of neither Ku80 nor DNA-PKcs complements the V(D)J recombination or radiosensitivity defects of XR-1 cells (Taccioli et al., 1994; Blunt et al., 1995). Instead, it has been shown that DNA from human chromosome region 5q13–14 complements XR-1 cells, the complementing gene being termed XRCC4 (Otevrel and Stamato, 1995).

Furthermore, (Li et al., 1995) have identified the XRCC4 gene recently through its ability to confer normal V(D)J recombination activity and partially restore the DSB repair defect on XR-1 cells, and have demonstrated that the XRCC4 locus is deleted in XR-1 cells.

Interestingly, XRCC4 encodes a small 334 amino acid residue protein of calculated molecular weight of 38 kDa, and the human and mouse homologues of this protein have been shown to be approximately 75% identical (Li et al., 1995). Perhaps surprisingly, however, sequence analyses reveal that XRCC4 is not significantly related to any previously-characterized proteins. Therefore, although it is clear that XRCC4 plays a crucial role in DNA DSB repair and V(D)J recombination, the cloning and sequencing of the cDNA for this factor has so far provided little clue to its mechanism of action.

The Li et al. paper is the only paper published on the XRCC4 protein as such prior to the priority date of the present invention. It reports that XRCC4 is not related to any other proteins and so its sequence gives no clear clues as to its function. Prior to the present work, therefore, the only assays available for XRCC4 were cellular radiosensitivity and cellular V(D)J recombination—assays that cannot be used as primary screens for inhibitors. Consequently, it was impossible to conceive of any biochemical screen for the activity of this factor.

It should be noted too that the Li et al. paper does not provide any evidence that XRCC4 is a nuclear protein (shown herein) and discusses on page 1084 that XRCC4 has putative sites for cytoplasmic protein tyrosine kinases. Thus, it is clear that there really was nothing known about how this protein might act.

The present inventors have shown that XRCC4 exists, at least in part, in the cell nucleus and demonstrated convincingly that it interacts with DNA ligase IV, and also DNA-PKcs/Ku. Evidence is provided herein in the experimental section, with confirmation being provided also by Mizuta et al., 1997. Grawunder et al, 1997 has also provided evidence of interaction between XRCC4 and DNA ligase IV. See also the inventors' publications Teo and Jackson, 1997 and Critchlow et al. 1997.

DNA ligases are catalysts which join together Okazaki fragments during lagging strand DNA synthesis, complete exchange events between homologous duplex DNA molecules, and seal single- or double-strand breaks in the DNA that are produced either by the direct action of a DNA damaging agents or by DNA repair enzymes removing DNA lesions (for review, see Lindahl and Barnes, 1992). In contrast to prokaryotic and yeast systems, where only a single species of DNA ligase has been previously been described (Johnston and Nasmyth, 1978), four biochemically distinct DNA ligases have been identified in mammalian cells (Tomkinson et al., 1991; Wei et al., 1995; Robins and Lindahl, 1996). In vitro assays, and studies of yeast and human cells containing mutated alleles of DNA ligase I suggest that this enzyme joins Okazaki fragments during DNA replication (Henderson et al., 1985; Malkas et al., 1990; Tomkinson et al., 1991; Barnes et al., 1992; Li et al., 1994; Prigent et al., 1994; Waga et al., 1994). Furthermore, the sensitivity of DNA ligase I mutant cells to ultraviolet (UV) irradiation and some DNA damaging agents suggests that DNA ligase I is involved in nucleotide excision repair and base excision repair (Henderson et al., 1985; Lehmann et al., 1988; Malkas et al., 1990; Tomkinson et al., 1991; Barnes et al., 1992; Li et al., 1994; Prigent et al., 1994; Waga et al., 1994).

Much less, however, is known about the function of the other three mammalian DNA ligases. It is currently unclear whether DNA ligase II and III arise from separate genes or by alternative splicing of the same gene (Roberts et al., 1994; Wang et al., 1994; Husain et al., 1995). However, ligase II is induced in response to alkylation damage (Creissen and Shall, 1982), suggesting a role in DNA repair. Similarly, the elevation of a splice variant of ligase III (ligase III-β) levels in spermatocytes undergoing meiotic recombination (Chen et al., 1995; Husain et al., 1995; Mackey et al., 1997) and the association of another splice variant (ligase III-α) with the DNA repair protein XRCC1 (Caldecott et al., 1994; Thompson et al., 1990) are consistent with this enzyme joining DNA strand breaks to complete DNA recombination and repair (Jessberger et al., 1993). Indeed, DNA ligase III, when present in a complex with XRCC-1, can reconstitute the ligation event necessary to complete base excision repair in vitro (Kubota et al., 1996).

A fourth enzyme, DNA ligase IV, has been purified recently from human cells and has distinct biochemical properties from other ligases (Robins and Lindahl, 1996). The physiological function of mammalian ligase IV is, however, unknown.

In most prokaryotes there is only one DNA ligase, and this enzyme catalyses all the DNA-joining events during replication, recombination and repair (Lindahl and Barnes, 1992). Similarly, genetic and biochemical data have suggested that there is only one DNA ligase in *Saccharomyces cerevisiae* (Lindahl and Barnes, 1992), although fractionation of yeast cell extracts has given an indication of a second DNA ligase activity (Tomkinson et al., 1992).

The present inventors searched for DNA ligase homologues in the *S. cerevisiae* genome, which was completely sequenced recently (Goffeau et al., 1996; Oliver, 1996). These searches identified a hitherto uncharacterized open reading frame (ORF) with sequence similarity along its entire length to mammalian DNA ligase IV. The experimental section below describes the effects of disrupting this gene, which the inventors have termed LIG4, on DNA replication, homologous recombination, and DNA repair in response to a variety of DNA-damaging agents. These studies show that LIG4 plays a crucial role in DNA double-strand break repair via the non-homologous end-joining (NHEJ) pathway but does not have an essential role in other DNA repair pathways studied.

Furthermore, it is shown that LIG4 functions in the same DNA repair pathway that utilizes the DNA end-binding protein Ku. However, the phenotype of lig4 mutant yeasts is not identical to those of yeasts disrupted for Ku function, revealing that Ku has additional roles in genome maintenance.

In summary, XRCC4 was known to be involved somehow in Ku-associated DNA double-strand break repair (KADR), but its biological activity was obscure. The present inventors have established for the first time biological activity of XRCC4, that is binding to DNA ligase IV. Furthermore, the physiological relevance of DNA ligase IV was not known. The inventors have now established that DNA ligase IV is important for double-strand DNA break repair via non-homologous end joining (NHEJ)—by unexpectedly identifying and cloning, then mutating, a yeast homologue gene and by establishing strong interaction between XRCC4 and DNA ligase IV.

The inventors have also established that XRCC4 interacts with DNA-PKcs/Ku, and shown that DNA-PKcs is able to phosphorylate XRCC4.

Based on this and other work described below, the present invention in various aspects provides for modulation of interaction between XRCC4 and DNA ligase IV.

Various aspect the present invention provide for the use of XRCC4 and DNA ligase IV in screening methods and assays for agents which modulate interaction between XRCC4 and DNA ligase IV.

Further aspects provide for modulation of interaction between XRCC4 and DNA-PKcs/Ku and use of these molecules in screening methods and assays for agents which modulate interaction between XRCC4 and DNA-PKcs/Ku. For simplicity, much of the present disclosure refers to XRCC4 and DNA ligase IV. However, unless the context requires otherwise, every such reference should be taken to be equally applicable to the interaction between XRCC4 and DNA-PKcs/Ku.

Methods of obtaining agents able to modulate interaction between XRCC4 and DNA ligase IV (or, it must be remembered, XRCC4 and DNA-PKcs/Ku) include methods wherein a suitable end-point is used to assess interaction in the presence and absence of a test substance. Detailed disclosure in this respect is included below. It is worth noting, however, that combinatorial library technology provides an efficient way of testing a potentially vast number of different substances for ability to modulate bind to and/or activity of a polypeptide. Such libraries and their use are known in the art, for all manner of natural products, small molecules and peptides, among others. The use of peptide libraries may be preferred in certain circumstances.

Appropriate agents may be obtained, designed and used for any of a variety of purposes.

One is anti-tumour or anti-cancer therapy, particularly augmentation of radiotherapy or chemotherapy. Ionizing radiation and radiomimetic drugs are commonly used to treat cancer by inflicting DNA damage. Cells deficient in DNA repair, particularly the KADR pathway, are hypersensitive to ionizing radiation and radiomimetics. Evidence provided herein shows the KADR pathway involves XRCC4 and DNA ligase IV, indicating that inhibition of their function, e.g. by inhibiting their interaction, will have an effect on the KADR pathway, DNA repair and cellular sensitivity to ionizing radiation and radiomimetics.

Another is the potentiation of gene targeting and gene therapy. Inhibition of KADR may be used to increase efficiencies of gene targeting, of interest and ultimate use in gene therapy. Two ways exist for repairing DNA double-stranded breaks (DSBs). One is through the process of illegitimate recombination (also known as DNA non-homologous end-joining or NHEJ) and this is catalysed by the KADR system now known to involve XRCC4 and DNA ligase IV. The other system is the process of homologous recombination, whereby the damaged DNA molecule exchanges information with an undamaged homologous partner DNA molecule. In mammalian cells, the illegitimate pathway tends to predominate. Inhibiting the KADR system will make the proportion of DSBs repaired by homologous recombination increase. Thus, anti-KADR factor agents, including those provided in accordance with the present invention, will have this effect. Homologous gene targeting is used in making knock-out mice and other transgenic animals but it is not very efficient, so increasing this efficiency in accordance with the present invention will be highly beneficial. Ultimately, gene therapist wish to precisely replace the mutated gene with a functional one. At present just to get the functional gene to integrate anywhere in the genome is the priority, but the long-term aim is for integration at the right site. KADR (e.g. XRCC4 and/or ligase IV, or XRCC4 and/or DNA-PKcs/Ku) inhibitors therefore have a great therapeutic potential in such context.

A further, related, purpose is in anti-retroviral therapy, since DNA repair pathways such as involving KADR and the components XRCC4 and DNA ligase IV are involved in effecting retroviral and retrotransposon integration into the genome of a host cell. Retroviruses are of considerable risk to the health of humans and animals, causing, inter alia, AIDS, various cancers and human adult T-cell leukemia/lymphoma. Integration of retroviral DNA into the genome is essential for efficient viral propagation and may be targeted by inhibition of DNA repair pathway components.

Additionally, modulators of KADR components such as XRCC4 and DNA ligase IV, DNA-PKcs/Ku, may be used in modulation of immune system function, since such factors are required for generation of mature immunoglobulin and T-cell receptor genes by site-specific V(D)J recombination.

Compounds which stabilize the interaction between two components, such as XRCC4 and DNA ligase IV, or XRCC4 and DNA-PKcs/Ku, and which may up-regulate activity, may be screened for using assays in which conditions are too harsh for the relevant interaction. Agents which stabilize the interaction may be identified. One alternative is to screen for substances that enhance DNA ligase IV catalytic activity, which may be determined as discussed elsewhere. An up-regulator of activity may be used to potentiate DNA repair further, and this may be in normal individuals, with possible long-term beneficial effects bearing in mind that many of the common manifestations of ageing arise through the gradual and inexorable accumulation of mutations in somatic cells. Up-regulators may be used in treating patients who are debilited in the KADR pathway or other DNA repair pathway.

Interaction between XRCC4 and DNA ligase IV, or XRCC4 and DNA-Pkcs/Ku may be inhibited by inhibition of the production of the relevant protein. For instance, production of one or more of these components may be inhibited by using appropriate nucleic acid to influence expression by antisense regulation. The use of anti-sense genes or partial gene sequences to down-regulate gene expression is now well-established. Double-stranded DNA is placed under the control of a promoter in a "reverse orientation" such that transcription of the "anti-sense" strand of the DNA yields RNA which is complementary to normal mRNA transcribed from the "sense" strand of the target gene. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works.

Another possibility is that nucleic acid is used which on transcription produces a ribozyme, able to cut nucleic acid at a specific site—thus also useful in influencing gene expression. Background references for ribozymes include Kashani-Sabet and Scanlon, 1995, *Cancer Gene Therapy*, 2(3): 213–223, and Mercola and Cohen, 1995, *Cancer Gene Therapy*, 2(1), 47–59.

Thus, various methods and uses of modulators, particularly inhibitors, of XRCC4 and DNA ligase IV, or XRCC4 and DNA-PKcs/Ku, interaction and/or activity are provided as further aspects of the present invention. The purpose of disruption, interference with or modulation of interaction between XRCC4 and DNA ligase IV, and/or XRCC4 and DNA-PKcs/Ku, may be to modulate any activity mediated by virtue of such interaction, as discussed above and further below.

BRIEF DESCRIPTION OF THE FIGURES

FIG. 1 illustrates co-purification of XRCC4 and DNA ligase IV from HeLa cells.

FIG. 2 shows that YOR005c encodes a homologue of mammalian DNA ligase IV, indicating amino acid sequence similarities between *S. cerevisiae* Lig4p (scLIG4; the product of the YOR005c ORF) and human DNA ligase IV (hLIGIV). The alignment was generated using the PILEUP programme on the GCG (Genetics Computer Group, Wisconsin) package, and identical and similar amino acid residues are indicated by reverse shading and grey shading, respectively, using the BOXSHADE programme. Amino acid residues are numbered from the amino termini of the full-length polypeptides. Gaps were introduced for maximum alignment. The active site lysine residue is indicated with an arrowhead. The "core" conserved region of DNA ligases of eukaryotes and eukaryotic viruses is delineated with a bar.

FIG. 3 shows that LIG4 functions in the Ku-dependent pathway for repairing ionizing radiation-induced DNA damage. The sensitivity of various yeast strains to killing by ionizing radiation was judged by exposure to various radiation doses. Error bars are not shown for simplicity; standard deviation is <5% of each value point.

FIG. 4 shows that disruption of LIG4 results in a dramatic reduction in the ability to repair restriction enzyme generated cohesive DNA DSBs in plasmid (pBTM116) DNA, plotting transformant recovery relative to uncut control plasmid where various yeast strains, wild-type and mutant, were transformed with pBTM116 digested with EcoRI (left panel) or PstI (right panel).

FIG. 6 shows the amino acid sequence and encoding nucleotide sequence for S. cerevisiae LIG4, provided in accordance with aspects of the present invention. Translation begins at the start site indicated by the arrow.

Figure 1A:
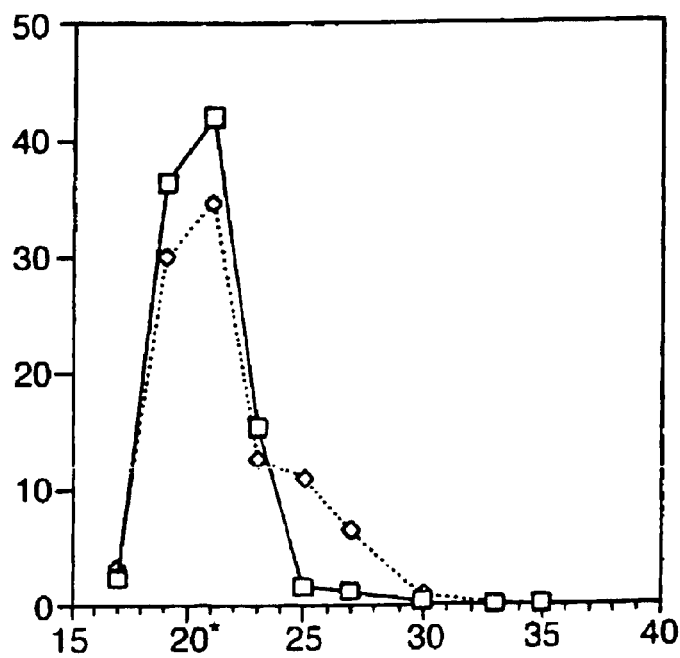
FIG. 1A shows the results of quantitative Western immunoblot analyses for DNA ligase IV (diamonds) and XRCC4 (squares) (percent of protein) for various fractions at each chromatographic stage of gel chromatography filtration for DNA ligase IV purification from HeLa cells.

Amino acid and nucleic acid sequences of polypeptides useful in various aspects of the present invention are available from GenBank under the following accession numbers: human Ku70-J04611; human Ku80-M30938; S. cerevisiae Ku70-X70379; S. cerevisiae Ku80-Z49702; human ligase IV-X83441; S. cerevisiae ligase IV-YOR005c on the right arm of S. cerevisiae chromosome XV, accession number Z74913; human XRCC4-U40622 (334 amino acid residue open reading frame); human DNA-Pkcs-U47077 (Hartley et al. originally provided the sequence, though lacking an intron. Poltoratsky et al. provided a partial sequence including the intron not included in the Hartley et al. sequence. The sequence available from GenBank is complete.).

All documents and GenBank sequences mentioned anywhere in this specification are incorporated by reference.

The present invention in various aspects provides for modulating, interfering with or interrupting interaction between the XRCC4 protein and DNA ligase IV, using an appropriate agent. The present invention also provides in analogous aspects for modulating, interfering with or interrupting interaction between the XRCC4 protein and DNA-Pkcs/Ku, using an appropriate agent.

Such an agent capable of modulating interaction between XRCC4 and DNA ligase IV may be capable of blocking binding between a site located within amino acid residues 550–884 of human DNA ligase IV, which may be at one or other or both of the BRCT domains (discussed further below), or between these domains, and a site on human XRCC4. The site on DNA ligase IV may be between amino acid residues 591–676, between amino acid residues 728–844 or between residues 677–727. The full amino acid sequence of the XRCC4 protein has been elucidated and is set out in Li et al. (Cell (1995) 83, 1079–1089) which is incorporated herein by reference, and of which the amino acid residue numbering is used along with the encoding nucleic acid sequence. The GenBank reference is indicated above. The DNA ligase IV amino acid and nucleotide coding sequences are given in Wei et al., of which the amino acid residue numbering is used, with the yeast LIG4 sequences being shown in FIG. 6. The GenBank references are given above.

Note, that recently Wilson, T. E. 1997, Nature 388: 495–498 has suggested that the initiating methionine for human DNA ligase IV is upstream from that indicated by Wei et al., 1995, whose amino acid sequence numbering is used herein. See the Wilson paper for details. The present inventors have preliminary data which disagrees with that of Wilson. However, should Wilson turn out to be correct this would have no bearing on any aspect of the present invention. The presence or absence of additional amino acids at the N-terminus of DNA ligase IV is unlikely to have any effect on its interaction with XRCC4, and the fact remains that the present inventors' work shows interaction of XRCC4 with the DNA ligase IV which occurs in human cells.

Agents may be identified by screening techniques which involve determining whether an agent under test inhibits or disrupts the binding of DNA ligase IV protein or a suitable fragment thereof (e.g. including amino acid residues 550–884, residues 591–676, residues 728–844 or residues 677–727, or a smaller fragment of any of these regions) of human DNA ligase IV, with XRCC4 or a fragment thereof, or a suitable analogue, fragment or variant thereof.

Suitable fragments of XRCC4 or DNA ligase IV include those which include residues which interact with the counterpart protein. Smaller fragments, and analogues and variants of this fragment may similarly be employed, e.g. as identified using techniques such as deletion analysis or alanine scanning.

Thus, the present invention provides a peptide fragment of XRCC4 which is able to bind DNA ligase IV and/or inhibit interaction between XRCC4 and DNA ligase IV, and provides a peptide fragment of DNA ligase IV which is able to bind DNA ligase IV and/or inhibit interaction between DNA ligase IV and XRCC4, such peptide fragments being obtainable by means of deletion analysis and/or alanine scanning of the relevant protein—making an appropriate mutation in sequence, bringing together a mutated fragment of one of the proteins with the other or a fragment thereof and determining interaction. In preferred embodiments, the peptide is short, as discussed below, and may be a minimal portion that is able to interact with the relevant counterpart protein and/or inhibit the relevant interaction.

Of course, similar considerations apply to XRRC4 and DNA-PKcs/Ku interacting portions.

Screening methods and assays are discussed in further detail below.

One class of agents that can be used to disrupt the binding of XRCC4 and DNA ligase IV are peptides based on the sequence motifs of XRCC4 or DNA ligase IV that interact with counterpart DNA ligase IV or XRCC4. Such peptides tend to be short, and may be about 40 amino acids in length or less, preferably about 35 amino acids in length or less, more preferably about 30 amino acids in length, or less, more preferably about 25 amino acids or less, more preferably about 20 amino acids or less, more preferably about 15 amino acids or less, more preferably about 10 amino acids or less, or 9, 8, 7, 6, 5 or less in length. The present invention also encompasses peptides which are sequence variants or derivatives of a wild type XRCC4 or DNA ligase IV sequence, but which retain ability to interact with DNA ligase IV or XRCC4 (respectively, as the case may be) and/or ability to modulate interaction between XRCC4 and DNA ligase IV.

Instead of using a wild-type XRCC4 or DNA ligase IV fragment, a peptide or polypeptide may include an amino acid sequence which differs by one or more amino acid residues from the wild-type amino acid sequence, by one or more of addition, insertion, deletion and substitution of one or more amino acids. Thus, variants, derivatives, alleles, mutants and homologues, e.g. from other organisms, are included.

Preferably, the amino acid sequence shares homology with a fragment of the relevant XRCC4 or DNA ligase IV fragment sequence shown preferably at least about 30%, or 40%, or 50%, or 60%, or 70%, or 75%, or 80%, or 85% homology, or at least about 90% or 95% homology. Thus, a peptide fragment of XRCC4 or DNA ligase IV may include 1, 2, 3, 4, 5, greater than 5, or greater than 10 amino acid alterations such as substitutions with respect to the wild-type sequence.

A derivative of a peptide for which the specific sequence is disclosed herein may be in certain embodiments the same length or shorter than the specific peptide. In other embodiments the peptide sequence or a variant thereof may be included in a larger peptide, as discussed above, which may or may not include an additional portion of XRCC4 or DNA ligase IV. 1, 2, 3, 4 or 5 or more additional amino acids, adjacent to the relevant specific peptide fragment in XRCC4 or DNA ligase IV, or heterologous thereto may be included at one end or both ends of the peptide.

(It should not be forgotten that references to XRCC4 and DNA ligase IV apply equally to XRCC4 and DNA-Pkcs/Ku.)

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art. Homology may be over the full-length of the relevant peptide or over a contiguous sequence of about 5, 10, 15, 20, 25, 30, 35, 50, 75, 100 or more amino acids, compared with the relevant wild-type amino acid sequence.

As noted, variant peptide sequences and peptide and non-peptide analogues and mimetics may be employed, as discussed further below.

Various aspects of the present invention provide a substance, which may be a single molecule or a composition including two or more components, which includes a peptide fragment of XRCC4 or DNA ligase IV which includes a sequence as included in the relevant GenBank entry, a peptide consisting essentially of such a sequence, a peptide including a variant, derivative or analogue sequence, or a non-peptide analogue or mimetic which has the ability to bind XRCC4 or DNA ligase IV and/or modulate, disrupt or interfere with interaction between XRCC4 or DNA ligase IV.

Variants include peptides in which individual amino acids can be substituted by other amino acids which are closely related as is understood in the art and indicated above.

Non-peptide mimetics of peptides are discussed further below.

As noted, a peptide according to the present invention and for use in various aspects of the present invention may include or consist essentially of a fragment of XRCC4 or DNA ligase IV as disclosed, such as a fragment whose sequence is included in the relevant GenBank entry. Where one or more additional amino acids are included, such amino acids may be from XRCC4 or DNA ligase IV or may be heterologous or foreign to XRCC4 or DNA ligase IV. A peptide may also be included within a larger fusion protein, particularly where the peptide is fused to a non-XRCC4 or DNA ligase IV (i.e. heterologous or foreign) sequence, such as a polypeptide or protein domain.

The invention also includes derivatives of the peptides, including the peptide linked to a coupling partner, e.g. an effector molecule, a label, a drug, a toxin and/or a carrier or transport molecule, and/or a targeting molecule such as an antibody or binding fragment thereof or other ligand. Techniques for coupling the peptides of the invention to both peptidyl and non-peptidyl coupling partners are well known in the art. In one embodiment, the carrier molecule is a 16 aa peptide sequence derived from the homeodomain of Antennapedia (e.g. as sold under the name "Penetratin"), which can be coupled to a peptide via a terminal Cys residue. The "Penetratin" molecule and its properties are described in WO 91/18981.

Peptides may be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing a peptidyl molecule according to the present invention (peptide or polypeptide) is to express nucleic acid encoding it, by use of nucleic acid in an expression system.

Accordingly the present invention also provides in various aspects nucleic acid encoding the polypeptides and peptides of the invention.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding a polypeptide or peptide in accordance with the present invention can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992), given the nucleic acid sequence and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding XRCC4 or DNA ligase IV fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the XRCC4 or DNA ligase IV sequences can be made, e.g. using site directed mutagenesis, to lead to the expression of modified XRCC4 or DNA ligase IV peptide or to take account of codon preference in the host cells used to express the nucleic acid.

In order to obtain expression of the nucleic acid sequences, the sequences can be incorporated in a vector having one or more control sequences operably linked to the nucleic acid to control its expression. The vectors may include other sequences such as promoters or enhancers to drive the expression of the inserted nucleic acid, nucleic acid sequences so that the polypeptide or peptide is produced as a fusion and/or nucleic acid encoding secretion signals so that the polypeptide produced in the host cell is secreted from the cell. Polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of *E. coli*, yeast, and eukaryotic cells such as COS or CHO cells.

Thus, the present invention also encompasses a method of making a polypeptide or peptide (as disclosed), the method including expression from nucleic acid encoding the polypeptide or peptide (generally nucleic acid according to the invention). This may conveniently be achieved by growing a host cell in culture, containing such a vector, under appropriate conditions which cause or allow expression of the polypeptide. Polypeptides and peptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing heterologous nucleic acid as disclosed herein.

The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell, or otherwise identifiably heterologous or foreign to the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide (or peptide) is produced. If the polypeptide is expressed coupled to an appropriate signal leader peptide it may be secreted from the cell into the culture medium. Following production by expression, a polypeptide or peptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Introduction of nucleic acid encoding a peptidyl molecule according to the present invention may take place in vivo by way of gene therapy, to disrupt or interfere with interaction between XRCC4 or DNA ligase IV.

Thus, a host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

This may have a therapeutic aim. (Gene therapy is discussed below.) Also, the presence of a mutant, allele, derivative or variant sequence within cells of an organism, particularly when in place of a homologous endogenous sequence, may allow the organism to be used as a model in testing and/or studying substances which modulate activity of the encoded polypeptide in vitro or are otherwise indicated to be of therapeutic potential. Knock-out mice, for instance, may be used to test for radiosensitivity. Conveniently, however, at least preliminary assays for such substances may be carried out in vitro, that is within host cells or in cell-free systems. Where an effect of a test compound is established on cells in vitro, those cells or cells of the same or similar type may be grafted into an appropriate host animal for in vivo testing.

Suitable screening methods are conventional in the art. They include techniques such as radioimnunosassay, scintillation proximetry assay and ELISA methods. Suitably either the XRCC4 protein or fragment or DNA ligase IV or fragment, or an analogue, derivative, variant or functional mimetic thereof, is immobilized whereupon the other is applied in the presence of the agents under test. In a scintillation proximetry assay a biotinylated protein fragment is bound to streptavidin coated scintillant—impregnated beads (produced by Amersham). Binding of radiolabelled peptide is then measured by determination of radioactivity induced scintillation as the radioactive peptide binds to the immobilized fragment. Agents which intercept this are thus inhibitors of the interaction. Further ways and means of screening for agents which modulate interaction between XRCC4 and DNA ligase IV are discussed below.

In one general aspect, the present invention provides an assay method for a substance with ability to modulate, e.g. disrupt or interfere with interaction or binding between XRCC4 and DNA ligase IV, the method including:

(a) bringing into contact a substance according to the invention including a peptide fragment of XRCC4 or a derivative, variant or analogue thereof as disclosed, a substance including the relevant fragment of DNA ligase IV or a variant, derivative or analogue thereof, and a test compound, under conditions wherein, in the absence of the test compound being an inhibitor of interaction or binding of said substances, said substances interact or bind; and (b) determining interaction or binding between said substances.

A test compound which disrupts, reduces, interferes with or wholly or partially abolishes binding or interaction between said substances (e.g. including a XRCC4 fragment and including a DNA ligase IV fragment), and which may modulate XRCC4 and/or DNA ligase IV activity, may thus be identified.

Another general aspect of the present invention provides an assay method for a substance able to bind the relevant region of XRCC4 or DNA ligase IV as the case may be, the method including:

(a) bringing into contact a substance which includes a peptide fragment of XRCC4 which interacts with DNA ligase IV as disclosed, or which includes a peptide fragment of DNA ligase IV which interacts with XRCC4, or a variant, derivative or analogue of such peptide fragment, as disclosed, and a test compound; and (b) determining binding between said substance and the test compound.

A test compound found to bind to the relevant portion of XRCC4 may be tested for ability to modulate, e.g. disrupt or interfere with, XRCC4 interaction or binding with DNA ligase IV and/or ability to affect DNA ligase IV and/or XRCC4 activity or other activity mediated by XRCC4 or DNA ligase IV as discussed already above.

Similarly, a test compound found to bind the relevant portion of DNA ligase IV may be tested for abiliy to modulate, e.g. disrupt or interfere with, DNA ligase IV interaction or binding with XRCC4 and/or ability to affect XRCC4 and/or DNA ligase IV activity or other activity mediated by DNA ligase IV or XRCC4 as discussed already above.

These aspects apply equally to interaction between DNA-Pkcs/Ku and XRCC4. Furthermore, since DNA-PKcs phosphorylates XRCC4, determining of such phosphorylation can be used in an appropriate assay.

A further aspect of the present invention provides an assay method including (a) bringing into contact a substance which includes at least a fragment of DNA-PKcs/Ku which phosphorylates XRCC4, a substance which includes at least a fragment of XRCC4 including a site phosphorylated by DNA-PKcs/Ku, and a test compound; and (b) determining phosphorylation at said site.

Of course, any suitable variant or derivative of DNA-PKcs/Ku and/or XRCC4 may be employed in such an assay.

Phosphorylation may be determined for example by immobilising XRCC4 or a fragment, variant or derivative thereof, e.g. on a bead or plate, and detecting phosphorylation using an antibody or other binding molecule which binds the relevant site of phosphorylation with a different affinity when the site is phosphorylated from when the site is not phosphorylated. Such antibodies may be obtained by means of any standard technique as discussed elsewhere herein, e.g. using a phosphorylated peptide (such as a fragment of XRCC4). Binding of a binding molecule which discriminates between the phosphorylated and non-phosphorylated form of XRCC4 or relevant fragment, variant or derivative thereof may be assessed using any technique available to those skilled in the art, which may involve determination of the presence of a suitable label, such as fluorescence. Phosphorylation may be determined by immobilisation of XRCC4 or a fragment, variant or derivative thereof, on a suitable substrate such as a bead or plate, wherein the substrate is impregnated with scintillant, such as in a standard scintillation proximetry assay, with phosphorylation being determined via measurement of the incorporation of radioactive phosphate. Rather than immobilising XRCC4, its phosphorylation by DNA-PKcs/Ku may be assayed by means of allowing its radio- or other labelling in solution, with a suitable specific binding member such as an antibody or DNA ligase IV or an XRCC4-binding fragment thereof being used to pull it out for determination of labelling. Phosphate incorporation into XRCC4 or a fragment, variant or derivative thereof, may be determined by precipitation with acid, such as trichloroacetic acid, and collection of the precipitate on a suitable material such as nitrocellulose filter paper, followed by measurement of incorporation of radiolabeled phosphate. SDS-PAGE separation of substrate may be employed followed by detection of radiolabel.

Another general aspect of the present invention provides an assay method for a substance able to affect DNA ligase IV activity, the method including:

(a) bringing into contact DNA ligase IV and a test compound; and (b) determining DNA ligase IV activity.

DNA ligase IV activity may be determined in the presence and absence of XRCC4 to allow for an effect of a test compound on activity to be attributed to an effect on interaction between DNA ligase IV and XRCC4.

DNA ligase IV activity may be conveniently determined by means of its adenylation. DNA ligase IV may be incubated with radiolabelled ATP (e.g. as described below) or any suitable ATP analogue that interacts with DNA ligase IV in an analogous manner, so that radiolabel is incorporated into the ligase. (The ligase goes through an enzyme-AMP adenylated intermediate.) Such radiolabel incorporation may be detected by various approaches, including for example scintillation proximetry assay Thus, radiolabelling of DNA ligase IV may be determined in the presence and absence of test compound and in the presence and absence of XRCC4. Pre-adenylation of DNA ligase IV with radiolabel allows for assaying for discharge of the radiolabel.

Another activity of DNA ligase IV which may be determined is DNA ligase IV-mediated DNA strand joining. For instance, two DNA molecules may be provided each of which includes a site to which a PCR primer anneals under appropriate conditions. When the two DNA molecules are covalently linked by DNA ligase IV to form a single DNA molecule, a PCR template results which can be amplified using the primers. No PCR product results in the absence of ligation. The amount of PCR product obtained in a given reaction can be quantitated with respect to DNA ligase activity. Another option is to attach a DNA molecule to an insoluble support and to add another, labelled DNA molecule. Following addition of DNA ligase IV in the presence or absence of a test compound and a washing step, attachment of the second molecule to the support, which can only take place via ligation to the DNA molecule bound to the support, can be determined by means of the label and related to DNA ligase IV activity. A further assay may include DNA end-joining, e.g. as described by Gawunder et al., 1997.

A substance found to be able to modulate DNA ligase IV activity, e.g. in the presence or absence of XRCC4, may be employed in a similar assay using DNA ligase I and/or DNA ligase III, in order to assess specificity for DNA ligase IV.

Performance of an assay method according to the present invention may be followed by isolation and/or manufacture and/or use of a compound, substance or molecule which tests positive for ability to modulate interaction between XRCC4 and DNA ligase IV and/or inhibit XRCC4 or DNA ligase IV activity or a mediated activity.

The precise format of an assay of the invention may be varied by those of skill in the art using routine skill and knowledge. For example, interaction between substances may be studied in vitro by labelling one with a detectable label and bringing it into contact with the other which has been immobilized on a solid support. Suitable detectable labels, especially for petidyl substances include $^{35}$S-methionine which may be incorporated into recombinantly produced peptides and polypeptides. Recombinantly produced peptides and polypeptides may also be expressed as a fusion protein containing an epitope which can be labelled with an antibody.

The protein which is immobilized on a solid support may be immobilized using an antibody against that protein bound to a solid support or via other technologies which are known per se. A preferred in vitro interaction may utilize a fusion protein including glutathione-S-transferase (GST). This may be immobilized on glutathione agarose beads. In an in vitro assay format of the type described above a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

An assay according to the present invention may also take the form of an in vivo assay. The in vivo assay may be performed in a cell line such as a yeast strain or mammalian cell line in which the relevant polypeptides or peptides are expressed from one or more vectors introduced into the cell.

The ability of a test compound to modulate interaction or binding between XRCC4 and DNA ligase IV may be determined using a so-called two-hybid assay.

For example, a polypeptide or peptide containing a fragment of XRCC4 or DNA ligase IV as the case may be, or a peptidyl analogue or variant thereof as disclosed, may be fused to a DNA binding domain such as that of the yeast transcription factor GAL 4. The GAL 4 transcription factor includes two functional domains. These domains are the DNA binding domain (GAL4DBD) and the GAL4 transcriptional activation domain (GAL4TAD). By fusing one polypeptide or peptide to one of those domains and another polypeptide or peptide to the respective counterpart, a functional GAL 4 transcription factor is restored only when two polypeptides or peptides of interest interact. Thus, interaction of the polypeptides or peptides may be measured by the use of a reporter gene probably linked to a GAL 4 DNA binding site which is capable of activating transcription of said reporter gene. This assay format is described by Fields and Song, 1989, Nature 340; 245–246. This type of assay format can be used in both mammalian cells and in yeast. Other combinations of DNA binding domain and transcriptional activation domain are available in the art and may be preferred, such as the LexA DNA binding domain and the VP60 transcriptional activation domain.

To take a Lex/VP60 two hybrid screen by way of example for the purpose of illustration, yeast or mammalian cells may be transformed with a reporter gene construction which expresses a selective marker protein (e.g. encoding β-galactosidase or luciferase). The promoter of that gene is designed such that it contains binding site for the LexA DNA-binding protein. Gene expression from that plasmid is usually very low. Two more expression vectors may be transformed into the yeast containing the selectable marker expression plasmid, one containing the coding sequence for the full length LexA gene linked to a multiple cloning site. This multiple cloning site is used to clone a gene of interest, i.e. encoding a XRCC4 or DNA ligase IV polypeptide or peptide in accordance with the present invention, in frame on to the LexA coding region. The second expression vector then contains the activation domain of the herpes simplex transactivator VP16 fused to a test peptide sequence or more preferably a library of sequences encoding peptides with diverse e.g. random sequences. Those two plasmids facilitate expression from the reporter construct containing the selectable marker only when the LexA fusion construct interacts with a polypeptide or peptide sequence derived from the peptide library.

A modification of this when looking for peptides or other substances which interfere with interaction between a XRCC4 polypeptide or peptide and DNA ligase IV polypeptide or peptide, employs the XRCC4 or DNA ligase IV polypeptide or peptide as a fusion with the LexA DNA binding domain, and the counterpart DNA ligase IV or XRCC4 polypeptide or peptide as a fusion with VP60, and involves a third expression cassette, which may be on a separate expression vector, from which a peptide or a library of peptides of diverse and/or random sequence may be expressed. A reduction in reporter gene expression (e.g. in the case of β-galactosidase a weakening of the blue colour) results from the presence of a peptide which disrupts the XRCC4/DNA ligase IV interaction, which interaction is required for transcriptional activation of the β-galactosidase gene. Where a test substance is not peptidyl and may not be expressed from encoding nucleic acid within a said third expression cassette, a similar system may be employed with the test substance supplied exogenously.

As noted, instead of using LexA and VP60, other similar combinations of proteins which together form a functional transcriptional activator may be used, such as the GAL4 DNA binding domain and the GAL4 transcriptional activation domain.

When performing a two hybrid assay to look for substances which interfere with the interaction between two polypeptides or peptides it may be preferred to use mammalian cells instead of yeast cells. The same principles apply and appropriate methods are well known to those skilled in the art.

The amount of test substance or compound which may be added to an assay of the invention will normally be determined by trial and error depending upon the type of compound used. Typically, from about 0.01 nM to 100 μM or more concentrations of putative inhibitor compound may be used, for example from 0.1 to 50 μM, such as about 10 μM. Greater concentrations may be used when a peptide is the test substance. Even a molecule with weak binding may be a useful lead compound for further investigation and development.

Compounds which may be used may be natural or synthetic chemical compounds used in drug screening programmes. Extracts of plants which contain several characterized or uncharacterized components may also be used.

Antibodies directed to the site of interaction in either protein form a further class of putative inhibitor compounds. Candidate inhibitor antibodies may be characterized and their binding regions determined to provide single chain antibodies and fragments thereof which are responsible for disrupting the interaction.

Antibodies may be obtained using techniques which are standard in the art. Methods of producing antibodies include immunizing a mammal (e.g. mouse, rat, rabbit, horse, goat, sheep or monkey) with the protein or a fragment thereof. Antibodies may be obtained from immunized animals using any of a variety of techniques known in the art, and screened, preferably using binding of antibody to antigen of interest. For instance, Western blotting techniques or immunoprecipitation may be used (Armitage et al., 1992, Nature 357: 80–82). Isolation of antibodies and/or antibody-producing cells from an animal may be accompanied by a step of sacrificing the animal.

As an alternative or supplement to immunizing a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunized with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimicks that of an antibody enabling it to bind an antigen or epitope.

Example antibody fragments, capable of binding an antigen or other binding partner are the Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

Antibodies may also be used in purifying and/or isolating a polypeptide or peptide according to the present invention, for instance following production of the polypeptide or peptide by expression from encoding nucleic acid therefor. Antibodies may be useful in a therapeutic context (which may include prophylaxis) to disrupt XRCC4/DNA ligase IV interaction with a view to inhibiting their activity. Antibodies can for instance be micro-injected into cells, e.g. at a tumour site. Antibodies may be employed in accordance with the present invention for other therapeutic and non-therapeutic purposes which are discussed elsewhere herein.

Other candidate inhibitor compounds may be based on modelling the 3-dimensional structure of a polypeptide or peptide fragment and using rational drug design to provide potential inhibitor compounds with particular molecular shape, size and charge characteristics.

A compound found to have the ability to affect XRCC4 and/or DNA ligase IV activity has therapeutic and other potential in a number of contexts, as discussed. For therapeutic treatment such a compound may be used in combination with any other active substance, e.g. for anti-tumour therapy another anti-tumour compound or therapy, such as radiotherapy or chemotherapy. In such a case, the assay of the invention, when conducted in vivo, need not measure the degree of inhibition of binding or of modulation of DNA ligase IV activity caused by the compound being tested. Instead the effect on DNA repair, homologous recombination, cell viability, cell killing (e.g. in the presence and absence of radio- and/or chemo-therapy), retroviral integration, and so on, may be measured. It may be that such a modified assay is run in parallel with or subsequent to the main assay of the invention in order to confirm that any such effect is as a result of the inhibition of binding or interaction between XRCC4 and DNA ligase IV caused by said inhibitor compound and not merely a general toxic effect.

Remember that the inventors have found interaction between XRCC4 and DNA-Pkcs/Ku and affecting this interaction is a part of the various aspects of the present invention in analogous fashion to affecting the interaction between XRCC4 and DNA ligase IV. The present inventors' finding in this respect is confirmed by Leber et al., "The XRCC4 gene product is a target for and interacts with the DNA-dependent protein kinase" *J. Biol. Chem* (1998) Jan. 16 273 (3), 1794—according to information available from the World Wide Web on Jan. 12, 1998.

An agent identified using one or more primary screens (e.g. in a cell-free system) as having ability to bind XRCC4 and/or DNA ligase IV and/or modulate activity of XRCC4 and/or DNA ligase IV may be assessed further using one or more secondary screens. A secondary screen may involve testing for cellular radiosensitisation and/or sensitisation to radiomimetic drugs, testing for impairment of V(D)J recombination in a transfection assay, and/or testing for ability to potentiate homologous recombination-mediated gene targeting. This may be tested directly and/or using a transfection assay that gives a read-out only after homologous recombination has occurred, (e.g. involving co-transformation or co-transfection of a cellular system with two plasmids that must undergo homologous recombination to yield an active reporter gene (such as luciferase or green fluorescent protein), or homologous integration of tranfected DNA into the genome.

Following identification of a substance or agent which modulates or affects XRCC4 and/or DNA ligase IV activity, the substance or agent may be investigated further Furthermore, it may be manufactured and/or used in preparation, i.e. manufacture or formulation, of a composition such as a medicament, pharmaceutical composition or drug. These may be administered to individuals, e.g. for any of the purposes discussed elsewhere herein.

As noted, the agent may be peptidyl, e.g. a peptide which includes a sequence as recited above, or may be a functional analogue of such a peptide.

As used herein, the expression "functional analogue" relates to peptide variants or organic compounds having the same functional activity as the peptide in question, which may interfere with the binding between XRCC4 and DNA ligase IV. Examples of such analogues include chemical compounds which are modelled to resemble the three dimensional structure of the XRCC4 or DNA ligase IV domain in the contact area, and in particular the arrangement of the key amino acid residues as they appear in XRCC4 or DNA ligase IV.

In a further aspect, the present invention provides the use of the above substances in methods of designing or screening for mimetics of the substances.

Accordingly, the present invention provides a method of designing mimetics of XRCC4 or DNA ligase IV having the biological activity of DNA ligase IV or XRCC4 binding or inhibition, the activity of allosteric inhibition of DNA ligase IV or XRCC4 and/or the activity of modulating, e.g. inhibiting, XRCC4/DNA ligase IV interaction, said method comprising:

(i) analysing a substance having the biological activity to determine the amino acid residues essential and important for the activity to define a pharmacophore; and, (ii) modelling the pharmacophore to design and/or screen candidate mimetics having the biological activity.

Suitable modelling techniques are known in the art. This includes the design of so-called "mimetics" which involves the study of the functional interactions fluorogenic oligonucleotide the molecules and the design of compounds which contain functional groups arranged in such a manner that they could reproduced those interactions.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesize, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The mimetic or mimetics found by this approach can then be screened to see whether they have the target property, or to what extent they exhibit it. Further optimisation or modification can then be carried out to arrive at one or more final mimetics for in vivo or clinical testing.

Mimetics of this type together with their use in therapy form a further aspect of the invention.

The present invention further provides the use of a peptide which includes a sequence as disclosed, or a derivative, active portion, analogue, variant or mimetic, thereof able to bind XRCC4 or DNA ligase IV and/or modulate, e.g. inhibit, interaction between XRCC4 and DNA ligase IV and/or modulate, e.g inhibit, XRCC4 and/or DNA ligase IV activity, in screening for a substance able to bind DNA ligase IV and/or XRCC4, and/or modulate, e.g. inhibit, interaction between XRCC4 and DNA ligase IV, and/or inhibit XRCC4 and/or DNA ligase IV activity.

Generally, such a substance, e.g. inhibitor, according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologicaly acceptable excipients. As noted below, a composition according to the present invention may include in addition to an inhibitor compound as disclosed, one or more other molecules of therapeutic use, such as an anti-tumour agent.

The present invention extends in various aspects not only to a substance identified as a modulator of XRCC4 and DNA ligase IV interaction and/or XRCC4 or DNA ligase IV-mediated activity, property or pathway, in accordance with what is disclosed herein, but also a pharmaceutical composition, medicament, drug or other composition comprising such a substance, a method comprising administration of such a composition to a patient, e.g. for a purpose discussed elsewhere herein, which may include preventative treatment, use of such a substance in manufacture of a composition for administration, e.g. for a purpose discussed elsewhere herein, and a method of making a pharmaceutical composition comprising admixing such a substance with a pharmaceutically acceptable excipient, vehicle or carrier, and optionally other ingredients.

A substance according to the present invention such as an inhibitor of XRCC4 and DNA ligase IV interaction or binding may be provided for use in a method of treatment of the human or animal body by therapy which affects DNA repair or other XRCC4 or DNA ligase IV-mediated activity in cells, e.g. tumour cells. Other purposes of a method of treatment employing a substance in accordance with the present invention are discussed elsewhere herein.

Thus the invention further provides a method of modulating DNA repair activity, particularly DSB end-joining, or other XRCC4 and/or DNA ligase IV-mediated activity, e.g. for a purpose discussed elsewhere herein, which includes administering an agent which modulates, inhibits or blocks the binding of XRCC4 to DNA ligase IV protein, such a method being useful in treatment where such modulation, inhibition or blocking is desirable.

The invention further provides a method of treatment which includes administering to a patient an agent which interferes with the binding of XRCC4 to DNA ligase IV. Exemplary purposes of such treatment are discussed elsewhere herein.

Whether it is a polypeptide, antibody, peptide, nucleic acid molecule, small molecule, mimetic or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

Liposomes, particularly cationic liposomes, may be used in carrier formulations.

Examples of techniques and protocols mentioned above can be found in Remington's Pharmaceutical Sciences, 16th edition, Osol, A. (ed), 1980.

The agent may be administered in a localized manner to a tumour site or other desired site or may be delivered in a manner in which it targets tumour or other cells.

Targeting therapies may be used to deliver the active agent more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering these agents directly, they may be produced in the target cells by expression from an encoding gene introduced into the cells, eg in a viral vector (a variant of the VDEPT technique—see below). The vector may targeted to the specific cells to be treated, or it may contain regulatory elements which are switched on more or less selectively by the target cells.

The agent (e.g. small molecule, mimetic) may be administered in a precursor form, for conversion to the active form by an activating agent produced in, or targeted to, the cells to be treated. This type of approach is sometimes known as ADEPT or VOEPT, the former involving targeting the activator to the cells by conjugation to a cell-specific antibody, while the latter involves producing the activator, e.g. an enzyme, in a vector by expression from encoding DNA in a viral vector (see for example, EP-A-415731 and WO 90/07936).

An agent may be administered in a form which is inactive but which is converted to an active form in the body. For instance, the agent may be phosphorylated (e.g. to improve solubility) with the phosphate being cleaved to provide an active form of the agent in the body.

A composition may be administered alone or in combination with other treatments, either simultaneously or sequentially dependent upon the condition to be treated, such as cancer, virus infection or any other condition in which a XRCC4 or DNA ligase IV-mediated effect is desirable.

Nucleic acid according to the present invention, encoding a polypeptide or peptide able to modulate, e.g. interfere with, XRCC4 and DNA ligase IV interaction or binding and/or induce or modulate activity or other XRCC4 or DNA ligase IV-mediated cellular pathway or function, may be used in methods of gene therapy, for instance in treatment of individuals, e.g. with the aim of preventing or curing (wholly or partially) a disorder or for another purpose as discussed elsewhere herein.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

A polypeptide, peptide or other substance able to modlate or interfere with the interaction of the relevant polypeptide, peptide or other substance as disclosed herein, or a nucleic acid molecule encoding a peptidyl such molecule, may be provided in a kit, e.g. sealed in a suitable container which protects its contents from the external environment. Such a kit may include instructions for use.

Further aspects of the present invention arise from the fact that the work described herein provides indication that mammals including humans deficient in XRCC4 and/or DNA ligase IV will have immune deficiencies, heightened cancer predisposition, particularly lyphoreticular malignancies, and/or will be radiosensitive.

For example, a small but significant percentage of human patients have disastrously debilitating (sometimes fatal) reactions to standard clinical doses of radiation. This is unfortunate, particularly where alternative modes of (e.g.) cancer treatment are available. The present invention allows and provides for diagnosis of such radiosensitive patients.

Diagnosis of XRCC4 and/or DNA ligase IV deficiency, which may be reduced ability of the particular polypeptide of an individual to interact with the other, or another component of a DNA repair pathway, may be used in conjunction with similar analysis of activity, function or structural integrity of other components of DNA repair pathways, such as Ku70, Ku80, DNA-PKcs, etc.

A number of methods are known in the art for analysing biological samples from individuals to determine whether the individual carries an allele of a particular gene predisposing them to a particular disorder. The purpose of such analysis may be used for diagnosis or prognosis, and serve to detect the presence of an existing defect (e.g. radiosensitivity), to help identify the type of defect (e.g. a factor in a manifest clinical disorder, such as cancer), to assist a physician in determining the severity or likely course of a disorder and/or to optimize treatment of it. Alternatively, the methods can be used to detect alleles that are statistically associated with a susceptibility to a disorder in the future, e.g. cancer, identifying individuals who would benefit from regular screening to provide early diagnosis of the disorder, e.g. cancer.

For instance, oligonucleotides designed to hybridize to a region within the gene of interest may be used in diagnostic and prognostic screening.

Oligonucleotide probes or primers, as well as the full-length gene sequence (and mutants, alleles, variants and derivatives) are useful in screening a test sample containing nucleic acid for the presence of alleles, mutants and variants, especially those that confer susceptibility or predisposition to a particular disorder, including radiosensitivity and cancers, the probes hybridizing with a target sequence from a sample obtained from the individual being tested. The conditions of the hybridization can be controlled to minimize non-specific binding, and preferably stringent to moderately stringent hybridization conditions are preferred. The skilled person is readily able to design such probes, label them and devise suitable conditions for the hybridization reactions, assisted by textbooks such as Sambrook et al (1989) and Ausubel et al (1992).

Nucleic acid isolated and/or purified from one or more cells (e.g. human) or a nucleic acid library derived from nucleic acid isolated and/or purified from cells (e.g. a cDNA library derived from mRNA isolated from the cells), may be probed under conditions for selective hybridization and/or subjected to a specific nucleic acid amplification reaction such as the polymerase chain reaction (PCR).

A method may include hybridization of one or more (e.g. two) probes or primers to target nucleic acid. Where the nucleic acid is double-stranded DNA, hybridization will generally be preceded by denaturation to produce single-stranded DNA. The hybridization may be as part of a PCR procedure, or as part of a probing procedure not involving PCR. An example procedure would be a combination of PCR and low stringency hybridization. A screening procedure, chosen from the many available to those skilled in the art, is used to identify successful hybridization events and isolated hybridized nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAase cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridized to the DNA fragments on the filter and binding determined. DNA for probing may be prepared from RNA preparations from cells.

Those skilled in the art are well able to employ suitable conditions of the desired stringency for selective hybridization, taking into account factors such as oligonucleotide length and base composition, temperature and so on.

PCR techniques for the amplification of nucleic acid are described in U.S. Pat. No. 4,683,195. In general, such techniques require that sequence information from the ends of the target sequence is known to allow suitable forward and reverse oligonucleotide primers to be designed to be identical or similar to the polynucleotide sequence that is the target for the amplification. PCR comprises steps of denaturation of template nucleic acid (if double-stranded), annealing of primer to target, and polymerisation. The nucleic acid probed or used as template in the amplification reaction may be genomic DNA, cDNA or RNA. PCR can be used to amplify specific sequences from genomic DNA, specific RNA sequences and cDNA transcribed from mRNA, bacteriophage or plasmid sequences. References for the general use of PCR techniques include Mullis et al, Cold Spring Harbor Symp. Quant. Biol., 51:263, (1987), Ehrlich (ed), PCR technology, Stockton Press, NY, 1989, Ehrlich et al, Science, 252:1643–1650, (1991), "PCR protocols; A Guide to Methods and Applications", Eds. Innis et al, Academic Press, New York, (1990).

On the basis of amino acid sequence information, oligonucleotide probes or primers may be designed, taking into account the degeneracy of the genetic code, and, where appropriate, codon usage of the organism from the candidate nucleic acid is derived. An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but not more than 18–20. Those skilled in the art are well versed in the design of primers for use processes such as PCR.

A further aspect of the present invention provides an oligonucleotide or polynucleotide fragment of XRCC4 or DNA ligase IV corresponding to part of the gene coding sequence or a complementary sequence, in particular for use in a method of obtaining and/or screening nucleic acid. The sequences referred to above may be modified by addition, substitution, insertion or deletion of one or more nucleotides, but preferably without abolition of ability to hybridize selectively with the relevant gene sequence, that is wherein the degree of homology of the oligonucleotide or polynucleotide with the sequence given is sufficiently high.

In some preferred embodiments, oligonucleotides according to the present invention that are fragments of the relevant gene sequence, in wild-type form or in the form of any allele associated with susceptibility to cancer or other disorder, are at least about 10 nucleotides in length, more preferably at least about 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of susceptibility to cancer or other disorder.

Preferred probes or primers according to certain embodiments of this aspect of the present invention are designed to hybridize with and/or amplify a fragment of the relevant sequence (e.g. XRCC4 or DNA ligase IV) including any residue mutation at which is associated with cancer susceptibility.

A number of methods are known in the art for analysing biological samples from individuals to determine whether the individual carries a gene allele with a mutation predisposing them to disease. The purpose of such analysis may be used for diagnosis or prognosis, and serve to detect the presence of, e.g., an existing cancer, to help identify the type of cancer, to assist a physician in determining the severity or likely course of the cancer and/or to optimize treatment of it. The methods may be used to detect alleles that are statistically associated with a susceptibility to cancer or other disorder in the future, e.g. early onset cancer, identifying individuals who would benefit from regular screening to provide early diagnosis of the disorder.

Broadly, the methods divide into those screening for the presence of nucleic acid sequences and those that rely on detecting the presence or absence of polypeptide. The methods make use of biological samples from individuals that are suspected of contain the nucleic acid sequences or polypeptide. Examples of biological samples include blood, plasma, serum, tissue samples, tumour samples, saliva and urine.

Exemplary approaches for detecting nucleic acid or polypeptides include:

(a) comparing the sequence of nucleic acid in the sample with a XRCC4 and/or DNA ligase IV nucleic acid sequence to determine whether the sample from the patient contains one or more mutations, e.g. in a particular region, such as a region which interacts with counterpart DNA ligase IV or XRCC4, as the case may be, or other component of a DNA repair pathway, or, particularly in the case of DNA ligase IV, a catalytic region, or, (b) determining the presence in a sample of a XRCC4 and/or DNA ligase polypeptide encoded by and, if present, determining whether the polypeptide includes a region corresponding to wild-type, and/or is mutated in such a region; or, (c) using DNA fingerprinting to compare the restriction pattern produced when a restriction enzyme cuts a sample of nucleic acid from the patient with the restriction pattern obtained from a particular region corresponding to that for the normal gene or from known mutations thereof; or, (d) using a specific binding member capable of binding to a nucleic acid sequence (either a normal sequence or a known mutated sequence) encoding a particular polypeptide fragment, the specific binding member comprising nucleic acid hybridisable with the relevant sequence, or substances comprising an antibody domain with specificity for a native or mutated polypeptide fragment nucleic acid sequence or the polypeptide encoded by it, the specific binding member being labelled so that binding of the specific binding member to its binding partner is detectable; or, (e) using PCR involving one or more primers based on the relevant normal or mutated gene sequence to screen for normal or mutant sequences within a particular region of the gene in a sample.

A "specific binding pair" in such a context may comprise a specific binding member (sbm) and a binding partner (bp) which have a particular specificity for each other and which in normal conditions bind to each other in preference to other molecules. Examples of specific binding pairs are antigens and antibodies (see above), molecules and receptors and complementary nucleotide sequences. The skilled person will be able to think of many other examples and they do not need to be listed here. Further, the term "specific binding pair" is also applicable where either or both of the specific binding member and the binding partner comprise a part of a larger molecule. In embodiments in which the specific binding pair are nucleic acid sequences, they will be of a length to hybridize to each other under the conditions of the assay, preferably greater than 10 nucleotides long, more preferably greater than 15 or 20 nucleotides long.

In most embodiments for screening for susceptibility alleles, the relevant nucleic acid (e.g. encoding XRCC4 and/or DNA ligase IV) in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

To reiterate in further detail, the identification of biochemical activity and physiological function of XRCC4 and DNA ligase IV and particular regions thereof paves the way for aspects of the present invention to provide the use of materials and methods, such as are disclosed and discussed above, for establishing the presence or absence in a test sample of an variant form of the gene, in particular an allele or variant specifically associated with cancer or other disorder such as radiosensitivity, as discussed. This may be for diagnosing a predisposition of an individual to a disorder. It may be for diagnosing a patient with a disorder as being associated with the gene.

This allows for planning of appropriate therapeutic and/or prophylactic treatment, permitting stream-lining of treatment by targeting those most likely to benefit.

A variant form of the gene may contain one or more insertions, deletions, substitutions and/or additions of one or more nucleotides compared with the wild-type sequence which may or may not disrupt the transcriptional activation function of the region examined herein. Differences at the nucleic acid level are not necessarily reflected by a difference in the amino acid sequence of the encoded polypeptide. However, a mutation or other difference in a gene may result in a frame-shift or stop codon, which could seriously affect the nature of the polypeptide produced, or a point mutation or gross mutational change to the encoded polypeptide, including insertion, deletion, substitution and/or addition of one or more amino acids or regions in the polypeptide, which may affect transcriptional activation.

There are various methods for determining the presence or absence in a test sample of a particular nucleic acid sequence, such as a sequence for XRCC4 or DNA ligase IV, or a fragment, mutant, variant or allele thereof.

Tests may be carried out on preparations containing genomic DNA, cDNA and/or MRNA. Testing cDNA or MRNA has the advantage of the complexity of the nucleic acid being reduced by the absence of intron sequences, but the possible disadvantage of extra time and effort being required in making the preparations. RNA is more difficult to manipulate than DNA because of the wide-spread occurrence of RN'ases.

Nucleic acid in a test sample may be sequenced and the sequence compared with the relevant wild-type sequence to determine whether or not a difference is present. If so, the difference can be compared with known susceptibility alleles, to determine whether the test nucleic acid contains one or more of the variations indicated, or the difference can be investigated for association with the disorder of interest.

Since it will not generally be time- or labour-efficient to sequence all nucleic acid in a test sample or even the whole gene for XRCC4 or DNA ligase IV, a specific amplification reaction such as PCR using one or more pairs of primers may be employed to amplify the region of interest in the nucleic aci. The amplified nucleic acid may then be sequenced as above, and/or tested in any other way to determine the presence or absence of a particular feature. Nucleic acid for testing may be prepared from nucleic acid removed from cells or in a library using a variety of other techniques such as restriction enzyme digest and electrophoresis.

Nucleic acid may be screened using a variant- or allele-specific probe. Such a probe corresponds in sequence to a region of the relevant gene, or its complement, containing a sequence alteration known to be associated with susceptibility to cancer or other disorder of interest. Under suitably stringent conditions, specific hybridization of such a probe to test nucleic acid is indicative of the presence of the sequence alteration in the test nucleic acid. For efficient screening purposes, more than one probe may be used on the same test sample.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected.

SSCP heteroduplex analysis may be used for screening DNA fragments for sequence variants/mutations. It generally involves amplifying radiolabelled 100–300 bp fragments of the gene, diluting these products and denaturing at 95° C. The fragments are quick-cooled on ice so that the DNA remains in single stranded form. These single stranded fragments are run through acrylamide based gels. Differences in the sequence composition will cause the single stranded molecules to adopt difference conformations in this gel matrix making their mobility different from wild type fragments, thus allowing detecting of mutations in the fragments being analysed relative to a control fragment upon exposure of the gel to X-ray film.

Fragments with altered mobility/conformations may be directly excised from the gel and directly sequenced for mutation.

Sequencing of a PCR product may involve precipitation with isopropanol, resuspension and sequencing using a TaqFS+ Dye terminator sequencing kit. Extension products may be electrophoresed on an ABI 377 DNA sequencer and data analysed using Sequence Navigator software.

A further possible screening approach employs a PTT assay in which fragments are amplified with primers that contain the consensus Kozak initiation sequences and a T7 RNA polymerase promoter. These extra sequences are incorporated into the 5' primer such that they are in frame with the native coding sequence of the fragment being analysed. These PCR products are introduced into a coupled transcription/translation system. This reaction allows the production of RNA from the fragment and translation of this RNA into a protein fragment. PCR products from controls make a protein product of a wild type size relative to the size of the fragment being analysed. If the PCR product analysed has a frame-shift or nonsense mutation, the assay will yield a truncated protein product relative to controls. The size of the truncated product is related to the position of the mutation, and the relative region of the gene from this patient may be sequenced to identify the truncating mutation.

An alternative or supplement to looking for the presence of variant sequences in a test sample is to look for the presence of the normal sequence, e.g. using a suitably specific oligonucleotide probe or primer.

Approaches which rely on hybridization between a probe and test nucleic acid and subsequent detection of a mismatch may be employed. Under appropriate conditions (temperature, pH etc.), an oligonucleotide probe will hybridize with a sequence which is not entirely complementary. The degree of base-pairing between the two molecules will be sufficient for them to anneal despite a mis-match. Various approaches are well known in the art for detecting the presence of a mis-match between two annealing nucleic acid molecules.

For instance, RN'ase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal gene (either sense or anti-sense strand) in which at least one mutation associated with, e.g., cancer susceptibility is known to occur, may be annealed to test nucleic acid and the presence or absence of a mis-match determined. Detection of the presence of a mis-match may indicate the presence in the test nucleic acid of a mutation associated with, e.g., cancer susceptibility. On the other hand, an oligonucleotide probe that has the sequence of a region of the gene including a mutation associated with, e.g., cancer susceptibility may be annealed to test nucleic acid and the presence or absence of a mis- match determined. The presence of a mis-match may indicate that the nucleic acid in the test sample has the normal sequence. In either case, a battery of probes to different regions of the gene may be employed. Indeed, probes may be included with probes or other materials for other genes for stream-lined testing.

The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enzyme or enzymes.

A test sample of nucleic acid may be provided for example by extracting nucleic acid from cells, e.g. in saliva or preferably blood, or for pre-natal testing from the amnion, placenta or foetus itself.

Nucleic acid according to the present invention, such as a full-length coding sequence or oligonucleotide probe or primer, may be provided as part of a kit, e.g. in a suitable container such as a vial in which the contents are protected from the external environment. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleosides, buffer solution etc. The nucleic acid may be labelled. A kit for use in determining the presence or absence of nucleic acid of interest may include one or more articles and/or reagents for performance of the method, such as means for providing the test sample itself, e.g. a swab for removing cells from the buccal cavity or a syringe for removing a blood sample (such components generally being sterile). In a further aspect, the present invention provides an apparatus for screening for XRCC4 and/or DNA ligase IV nucleic acid, the apparatus comprising storage means including the relevant gene nucleic acid sequence, or a fragment thereof, the stored sequence being used to compare the sequence of the test nucleic acid to determine the presence of mutations.

There are various methods for determining the presence or absence in a test sample of a particular polypeptide, such as a polypeptide including a fragment of XRCC4 or DNA ligase IV corresponding to a particular region involved in interaction with counterpart DNA ligase IV or XRCC4, as the case may be, involved in interaction with one or more other proteins or components of a DNA repair pathway, or having a particular biological activity, such as DNA ligase enzymatic activity.

A sample may be tested for the presence of a binding partner for a specific binding member such as an antibody (or mixture of antibodies), specific for one or more particular variants of the polypeptide, i.e. wild-type or a mutant, variant or allele thereof.

A sample may be tested for the presence of a binding partner for a specific binding member such as an antibody (or mixture of antibodies), specific for the polypeptide.

In such cases, the sample may be tested by being contacted with a specific binding member such as an antibody under appropriate conditions for specific binding, before binding is determined, for instance using a reporter system as discussed. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequence and/or properties of the polypeptide of interest, or if it is a mutant or variant form. Amino acid sequence is routine in the art using automated sequencing machines.

Protein may be detected using Western blots, and also Far-Western blots in which a non-antibody protein is used. For instance, XRCC4 could be used to determine the presence of DNA ligase IV, and vice versa. Immunoprecipitation, radio-immunoassay, ELISA and other standard approaches in the art may be employed, using antibodies and other appropriate specific binding agents.

Various further aspects and embodiments of the present invention will be apparent to those skilled in the art in view of the present disclosure. Certain aspects and embodiments of the invention will now be illustrated by way of example and with reference to the figures discussed already above.

EXAMPLE 1

DETERMINATION OF BIOLOGICAL ACTIVITY OF XRCC4

Generation of Antisera that Recognize XRCC4

With the aim of gaining insights into the mechanism of XRCC4 action, it was decided to try to characterize the human protein biochemically. Towards this end, full-length human XRCC4 and the C-terminal region of XRCC4 comprising residues 201–344 were expressed in *Escherichia coli* as hexa-histidine-tagged proteins. After purification to homogeneity, each antigen was then used to raise polyclonal antisera in rabbits.

In the course of these studies, we observed that recombinant full-length XRCC4 runs anomalously upon SDS-PAGE, with an apparent molecular mass of ~55 kDa, which is considerably larger than the predicted molecular weight of 38 kDa. Untagged and His-tagged versions of XRCC4 were found to behave similarly. Although the reason for this is currently unclear, this might reflect the fact that XRCC4 contains an unusually large proportion of glutamic acid amino acid residues, increasing the negative charge of the protein. One possible result of this would be a net decrease in the amount of SDS bound to the protein which would decrease the mobility of XRCC4 upon SDS-PAGE analysis.

Western blot analyses revealed that each of the anti-XRCC4 antisera raised was capable of recognizing less than 1 ng of recombinant XRCC4 protein. To establish whether these antisera are capable of detecting endogenous XRCC4 in mammalian cell lysates, crude HeLa cell nuclear extracts were subjected to SDS-PAGE followed by Western immunoblot analysis.

Importantly, each antiserum, but none of the pre-immune sera, was found to recognize a HeLa cell protein of 55–60 kDa, which is in good agreement with the size of recombinant XRCC4. In addition, each immune serum also detects several other polypeptides weakly. Although the identities of these are not established, some may correspond to alternative forms of XRCC4 or its proteolytic degradation products. For instance, one band in particular is likely to represent a N-terminal XRCC4 proteolytic product because it is recognized by all sera raised against the full-length protein but not by serum SJ5 that was raised against the XRCC4 C-terminal region. Interestingly, despite the high degree of sequence conservation between XRCC4 in rodents and humans (Li et al., 1995), we have been unable to detect XRCC4 in extracts of mouse or hamster cells by direct Western blotting using these antibodies. This could in part reflect low immunological cross-reactivity between the human and rodent proteins. However, given the evolutionary conservation of XRCC4, the model that we currently favour is that, as is the case for other DNA DSB repair factors, such as Ku and DNA-PKcs (Blunt et al., 1995; Finnie et al., 1995; Danska et al., 1996), XRCC4 is expressed at much lower levels in rodent cells than in human cells (also, see below).

To enhance further the specificity of anti-XRCC4 antiserum SJ4B, this was subjected to immuno-affinity chromatography using XRCC4 that had been attached covalently to Sepharose beads. Significantly, whereas the crude serum recognizes a number of polypeptides in HeLa whole cell extracts in addition to full-length XRCC4, much of the reactivity towards the other proteins is recovered in the flow-through fractions, resulting in the affinity-purified antibody material (eluate) having improved specificity and selectivity as compared to the unfractionated serum.

XRCC4 is a Nuclear Phosphoprotein and Serves as an Effective Substrate for DNA-PK in vitro As a first step towards establishing the biochemical function of XRCC4, we decided to try to determine its subcellular localisation. Nuclear and cytosolic fractions were prepared from HeLa cells and were subjected to Western blot analysis using affinity-purified XRCC4 antibody SJ4B. The integrity of the fractions was established by also probing with antisera against Sp1 which is located predominantly in the nuclear fraction.

Figure 5:
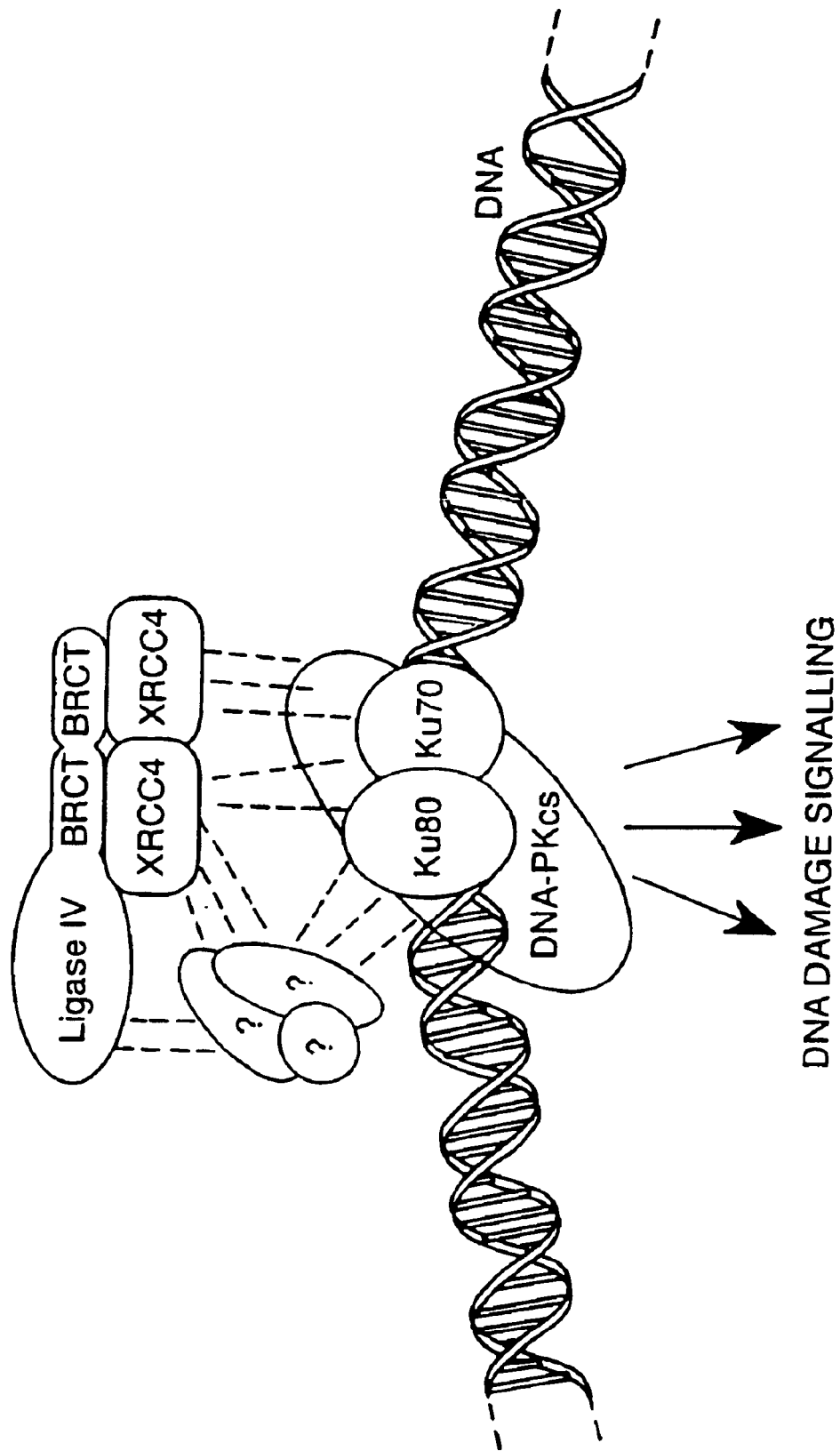
FIG. 5 shows a model in which XRCC4 serves as a molecular bridge to target DNA ligase IV to a DNA DSB.

Notably, these studies revealed that XRCC4 is present in the nuclear extract, with low amounts being detectable in the cytosolic fraction. These data therefore reveal that XRCC4 is a nuclear protein and are consistent with models in which XRCC4 serves as part of a DNA DSB repair apparatus, for instance as illustrated in FIG. 5.

In this model (which is proposed without in any way limiting the nature or scope of any aspect of the present invention or embodiment thereof), Ku binds to the free DNA ends and recruits DNA-PKcs, activating the kinase catalytic function of the latter. A DNA ligase IV/XRCC4 complex is then recruited to the DNA DSB. One or more additional components may be involved: some possibilities are indicated by means of question marks. Active DNA-PK may also trigger DNA damage signalling events or may phosphorylate other DNA DSB repair components, such as XRCC4 as has been demonstrated by the inventors, thus regulating their activity. The stoichiometry of the XRCC4-DNA ligase IV complex is for the purpose of illustration only. XRCC4 may interact with DNA ligase IV anywhere within residues 550–884 of human DNA ligase IV, e.g. at or between the BRCT domains.

During the course of the above studies, we observed that HeLa XRCC4 reproducibly migrates more slowly than recombinant XRCC4 on SDS-PAGE, suggesting that human XRCC4 is modified post-translationally. To determine whether this reflects XRCC4 phosphorylation, HeLa nuclear extract was either mock-treated, treated with λ protein phosphatase, or was treated with λ phosphatase in the presence of phosphatase inhibitors.

Significantly, Western analysis of these samples revealed that λ phosphatase increases the SDS-PAGE mobility of HeLa XRCC4 so that it is now equivalent to that of the recombinant protein, whereas this effect is abrogated by phosphatase inhibitors. These data therefore reveal that XRCC4 is phosphorylated to high stoichiometry in HeLa cell extracts and suggest that this modification is used to modulate XRCC4 activity in vivo.

In light of this, and because cells deficient in XRCC4 have very similar phenotypes to those defective in components of DNA-PK, we tested whether DNA-PK is able to phosphorylate XRCC4 in vitro. XRCC4 indeed serves as an effective substrate for DNA-dependent phosphorylation by DNA-PK, so DNA-PK may control XRCC4 activity within the cell.

Endogenous XRCC4 Appears to be Completed With Another Protein(s)

There are various ways in which XRCC4 might function in DNA DSB repair and V(D)J recombination.

One possibility the inventors considered is that it interacts directly with DNA and plays a role in repairing DNA damage or signalling its presence to the cell. However, we have been unable to detect binding of recombinant XRCC4 to various DNA species in electrophoretic mobility shift assays. Furthermore, when HeLa nuclear extracts are passed through DNA-agarose columns under salt concentrations in which many DNA binding proteins are retained, the majority of endogenous XRCC4 flows through.

These data therefore argue that XRCC4 does not bind avidly to DNA.

Another possible role for XRCC4 considered by the inventors is for it to interact with another component of the DNA DSB repair apparatus. As an approach to address this idea, we investigated the biochemical fractionation of XRCC4 and other known and potential DNA DSB repair factors upon gel-filtration chromatography on Superose-6. To disrupt possible non-specific protein-protein associations, such experiments were performed under stringent conditions of 1 M NaCl.

These studies revealed that recombinant untagged XRCC4 elutes in a manner consistent with a mass of just over 66 kDa, which is larger than the predicted XRCC4 monomer molecular weight (Li et al., 1995) and its apparent mass as determined by SDS-PAGE. This suggests either that XRCC4 is a monomeric protein with shape characteristics causing it to behave anomolously upon gel-filtration, or exists in solution as a multimer, most likely a dimer.

Most significantly, gel-filtration analysis of HeLa nuclear extract in the presence of 1 M NaCl reveals that endogenous XRCC4 fractionates in a manner consistent with a molecular mass of around 200 kDa, which is markedly higher than that for recombinant XRCC4. These data therefore suggest strongly that HeLa XRCC4 is associated with another protein(s). We took the same set of gel-filtration fractions tested above for XRCC4 and examined them for the presence of Ku, DNA-PK$_{cs}$, and DNA ligases I, III and IV.

Significantly, although some overlap was evident in each case, the XRCC4 elution profile did not parallel those exhibited for DNA ligase I, Ku or DNA-PK$_{cs}$. Thus, ligase I peaked at ~150 kDa which is slightly larger than the predicted monomer molecular weight of 1–2 kDA, DNA-PK$_{cs}$ (465 kDA) eluted at around 200 kDa which may indicate that the tertiary structure of DNA-PK is disrupted under these conditions, and Ku elution peaked at ~150 kDa, consistent with the predicted size of a Ku70/Ku80 heterodimer.

In marked contrast, the elution profile of XRCC4 was found to be virtually identical to those of DNA ligases III and IV. These results therefore raised the possibility that XRCC4 exists in stable association with either DNA ligase III or IV.

HeLa Cell XRCC4 co-immunoprecipitates With DNA Ligase IV

To further test for possible interactions between XRCC4 and the factors described above, we immunoprecipitated XRCC4 from its peak gel-filtration fractions in the presence of 1 M NaCl and 50 μg/ml ethidium bromide (to abolish non-specific interaction mediated via DNA), and tested the resulting precipitated material for the presence of Ku, DNA-PKC$_{cs}$, and ligases I, III, and IV. Significantly, Western immunoblot analyses revealed that DNA-PK$_{cs}$, Ku, and DNA ligase I that were present in the XRCC4 fractions did not co-immunoprecipitate with XRCC4, confirming that XRCC4 does not interact stably with any of these factors under these assay conditions. Note, however, that as discussed elsewhere herein, the inventors have established that DNA-PKcs/Ku is able to interact with XRCC4 under other conditions. They have shown also that it phosphorylates XRCC4, which of course requires some interaction between the proteins. This is confirmed by Leber et al., "The XRCC4 gene product is a target for and interacts with the DNA-dependent protein kinase" J. Biol. Chem (1998) Jan. 16 273 (3), 1794—according to information available from the World Wide Web on Jan. 12, 1998.

To assay for possible interactions between XRCC4 and a DNA ligase enzyme, we employed the fact that mammalian DNA ligases form covalently-linked adenylate complexes (Tomkinson et al., 1991; Wei et al., 1995; Danska et al., 1996; Robins and Lindahl, 1996). When the XRCC4-containing gel-filtration fraction was incubated with [α-$^{32}$P]-ATP and was then examined by SDS-PAGE followed by autoradiography, adenylated proteins of approximately 120 kDa and 100 kDa were detected, which correspond to DNA ligase I and a mixture of DNA ligases III and IV, respectively.

To see whether any of these ligases associate with XRCC4, unlabelled extract was incubated with pre-immune or anti-XRCC4 antisera in the presence of 1 M NaCl then, after stringent washing, the immunoprecipitated material was incubated with [α-$^{32}$P]-ATP and tested for radioactively-labelled adenylated proteins.

Significantly, these studies revealed that an adenylated protein species of ~100 kDa, corresponding to DNA ligase III and/or IV is immunoprecipitated efficiently by the affinity purified XRCC4 antiserum but not by pre-immune sera. By contrast, the adenylated species corresponding to DNA ligase I is not recovered. Importantly, and consistent with the fact that the adenylate moiety of adenylated-DNA ligase complexes is discharged in the presence of ligatable polynucleotide substrates, the radiolabel associated with the XRCC4-precipitated material is lost upon incubation in the presence of DNA that has been nicked by treatment with DNase I.

To rule out the possibility that the immunoprecipitated ligase was being recognized directly by the anti-XRCC4 antiserum, we performed parallel immunoprecipitation reactions on extracts derived from the hamster cell lines K1 and XR-1, which contain and lack XRCC4 protein, respectively. Importantly, the ~100 kDa adenylated ligase species is recovered from K1 extracts but not from XR-1 extracts. These data therefore reveal that the ligase is not recognized by the antiserum directly and, instead, is immunoprecipitated via its association with XRCC4.

Taken together, the above results reveal that XRCC4 forms a tight salt-stable interaction with DNA ligase III and/or DNA ligase IV. To establish which of these two enzymes is associated with XRCC4, we took advantage of the fact that ligases III and IV have different abilities to join single-strand breaks in polynucleotide substrates containing one DNA strand and one RNA strand. Thus, whereas DNA ligase III can catalyse joining in both oligo(rA).poly(dT) and oligo(dT).poly(rA) substrates, ligase IV is only able to mediate joining of the latter (Robins, 1996).

In light of this, we performed adenylation assays on material immunoprecipitated with XRCC4 and then incubated the labelled immunoprecipitates with either oligo(dT) .poly(rA) or oligo(rA).poly(dT). Notably, only oligo(dT) .poly(rA) resulted in dissociation of the adenylate group from the ligase that is immunoprecipitated with XRCC4.

These results therefore suggest strongly that XRCC4 interacts tightly and specifically with DNA ligase IV but not with DNA ligase III.

XRCC4 and Ligase IV Co-purify Extensively

To confirm the interaction between XRCC4 and DNA ligase IV, and to gain insight into what proportion of the two proteins exists in this complex, we purified DNA ligase IV using established protocols (Robins, 1996) and tested for the presence of ligase IV and XRCC4 by quantitative Western immunoblot analyses at each chromatographic stage.

Fractions collected from the chromatographic columns were analysed on SDS-polyacrylamide gels and specific binding of antibodies was detected by immunoblots. The amount of specified protein in each fraction was quantitated from densitometric scans of the gels. The amount of each protein in analysed fractions as a proportion of its total amount was plotted for the samples separated by gel chromatography fractionation (FIG. 1A), followed by a Mono S column (FIG. 1B)

Figure 1B:
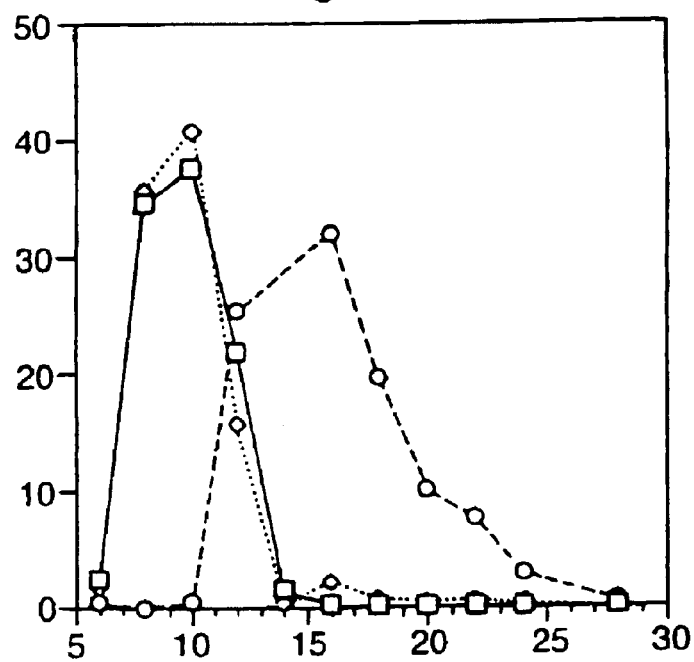
FIG. 1B shows results of quantitative Western immunoblot analyses for DNA ligase IV (diamonds), XRCC4 (squares) and DNA ligase III (circles) (percent of protein) for various tractions at each stage of Mono S column fractionation on the fraction marked with an asterisk in FIG. 1A.

As demonstrated previously, we observed that DNA ligases III and IV co-elute during gel filtration chromatography (FIG. 1A) but are resolved from one another by chromatography on Mono-S (FIG. 1B) Significantly, XRCC4 tracks with ligase IV throughout these procedures but, in contrast, becomes separated from DNA ligase III at the Mono-S chromatography step (FIGS. 1A and 1B). Furthermore, XRCC4 is present even in more highly purified samples of DNA ligase IV generated via subsequent chromatography on Mono Q, and immunoblot analyses of near homogenous ligase IV preparations that we had prepared previously demonstrates the existence of XRCC4. Samples further purified on a Mono Q column (Robins, 1996) were analysed on a 10% SDS-polyacrylamide gel by immunoblots testing for the presence of XRCC4 or DNA ligase IV. Molecular sizes were estimated from the migration of Kaleidoscope pre-stained markers.

In additional studies, we have also observed that XRCC4 and DNA ligase IV co-purify on phenyl-Sepharose. Indeed, short of incubation with harsh ionic detergents, we have yet to find a procedure to separate these two proteins.

Interestingly, the XRCC4 that co-purifies with ligase IV corresponds to the phosphorylated form of the protein as evidenced by its SDS-PAGE mobility and by the fact that this mobility is increased by phosphatase treatment.

Finally, it is particularly noteworthy that XRCC4 and ligase IV co-purify almost quantitatively with one another, and that no free pools of either factor are evident (for example, see FIGS. 1A and 1B). This therefore suggests that XRCC4 and DNA ligase IV are present at similar levels in the cell and that virtually all of each polypeptide exists in a complex with its partner.

XRCC4 Interacts With the C-terminal Portion of DNA Ligase IV That Comprises Two BRCT Homology Domains To gain insights into the basis for the highly specific binding of DNA ligase IV to XRCC4, we decided to try to determine which region(s) of ligase IV are involved in this interaction.

DNA ligase I, III and IV display high levels of sequence similarity to one another within a section that has been defined as the core ligase catalytic domain (Wei et al., 1995). In addition, each ligase possesses discrete N- and/or C-terminal extensions that have been proposed to confer unique properties on the three enzymes. Significantly, although the C-terminal extensions of DNA ligases III and IV show very little homology with one another at the primary sequence level, they possess one and two copies, respectively, of the recently identified BRCT homology domain (Koonin et al., 1996; Callebaut and Mornon, 1997); see Discussion below).

With the aim of finding which region(s) of ligase IV interacts with XRCC4, we divided the ligase IV polypeptide into three portions—an N-terminal region (corresponding to amino acid residues 1–198) that exhibits homology with ligase I and III, a central region (residues 199–549) that shows highest levels of homology with ligase I and III and which contains the ligase catalytic site, and a C-terminal region (residues 550–844) that contains the two BRCT homology domains. After transcribing and translating the three regions separately in vitro, these were tested for an ability to bind to Sepharose beads or to Sepharose beads containing covalently-attached XRCC4. Samples of LigIV (1–198), Lig IV(199–549), Lig IV(550–844) and luciferase were applied to XRCC4-Sepharose beads or negative control beads (ON) and unbound proteins collected (FT). After washes with either 0.1 M and 1.0 M NaCl, bound proteins were eluted with gel loading buffer (SDS). After SDS-PAGE, the [$^{35}$S]methionine-labelled fragments were detected by autoradiography.

The N-terminal and central fragments of DNA ligase IV fail to bind detectably to the XRCC4-beads, as is the case for the luciferase protein that was employed as a control. In marked contrast, the ligase IV C-terminal fragment is retained almost quantitatively on the XRCC4-beads but not on control beads lacking XRCC4. Moreover, the binding of the C-terminal portion of ligase IV to XRCC4 appears to be very strong, as evidenced by the fact that the ligase IV C-terminal region is not eluted by washing at 1 M NaCl and is only recovered following addition of the ionic detergent SDS.

Finally, to further address the specificity of the above interaction, we assessed whether XRCC4-containing beads could be used to purify the C-terminal region of ligase IV from crude bacterial lysates. To do this, an unfractionated extract of E. coli expressing this region (LIGIV (550–844)) at fairly low levels was incubated with XRCC4-containing Sepharose beads and unbound proteins collected. Bound material was then eluted with step-wise increases in salt concentrations, followed by a final elution in the presence of gel loading buffer, SDS.

Strikingly, as shown by total Coomassie-blue protein staining of an SDS-polyacrylamide gel containing these fractions, this procedure results in the C-terminal region of ligase IV being purified to virtual homogeneity in a single step. The identity of this polypeptide as the ligase IV C-terminus was confirmed by Western blot analyses, and this protein was not retained by Sepharose beads alone.

Taken together, these results attest to the extreme strength and specificity of the interaction between the ligase IV C-terminal region and XRCC4.

MATERIALS AND METHODS

Enzymes, Antibodies and DNA pET-30b and pQE-30 were obtained from Novagen and Qiagen, respectively. Purified mouse monoclonal MRG-S.His antibody (Qiagen) that recognizes pQE-30-derived His-tagged proteins was used as per manufacturer's instructions. Ku70, Ku80, and DNA-PK$_{cs}$ antisera were used as described previously (Hartley et al., 1995; Finnie et al., 1996). Antibodies against ligase I (TL5), ligase III (TL25) and ligase IV (TL18) were used as described by (Lasko et al., 1990; Robins and Lindahl, 1996). Antigen-antibody complexes were detected by enhanced chemi-luminescence (Amersham) according to the manufacturer's instructions. HeLa nuclear extract was obtained from Computer Cell Culture Centre, Mons, Belgium. All plasmid constructs were verified by automated DNA sequencing.

Expression and Purification of XRCC4 Derivatives

To generate recombinant untagged XRCC4, the full-length XRCC4 coding region was amplified from pBlue-Script containing the human XRCC4 gene by PCR and inserted into pET-30a (Novagen) digested with Nde I/Sal I such that the N-terminal His/S tags are not present and so that the XRCC4 stop codon prevents the addition of the C-terminal His-tag. For protein expression, BL21(DE3) cells harbouring the resulting plasmid (pET30XRCC4) were grown in 500 ml cultures of LB/kanamycin (50 µg/ml) to mid-log prior to induction with 0.4 mM JPTG for 4 h at 37° C. After lysing the collected cell pellet by sonication, 30.2 g of ammonium sulphate was added slowly per 100 ml of supernatant and incubated with stirring at 4° C. for 30 min. After centrifugation, the pellet was resuspended in TED (50 mM Tris-HCl pH 7.5, 2 mM DTT and 1 mM EDTA) and dialysed extensively against TED. Protein was then loaded onto a heparin-Sepharose column pre-equilibrated with TED and protein was eluted with a linear gradient of 0 to 0.6 M NaCl. Fractions containing XRCC4 were pooled and dialysed against TED containing 1.0 M ammonium sulphate then were loaded onto a pre-equilibrated phenyl-Sepharose column. Proteins were eluted with a 100 ml linear gradient of 1.0 to 0 M $(NH_4)_2SO_4$. Fractions containing XRCC4, eluting at ~0.2 M $(NH_4)_2SO_4$, were pooled and dialysed against 50 mM Tris.HCl pH 7.5, 2 mM DTT, 1 mM EDTA and 10% (w/v) glycerol, and stored at ~80° C.

Anti-XRCC4 Antibody Production and Purification

Regions of the XRCC4 gene were amplified by PCR from pBlueScript containing the human XRCC4 gene then were inserted in-frame downstream of the hexa-histidine (His) tag of pQE-30 (Qiagen, USA) and were expressed and purified according to the manufacturer's instructions from the soluble fraction of bacterial lysates. Antibodies against the soluble recombinant proteins were raised in rabbits using standard procedures (Harlow and Lane, 1988) and are available commercially from Serotec, UK. Western immunoblot analyses were performed as described previously (Harlow and Lane, 1988) and blots were developed by enhanced chemi-luminescence (Amersham). Recombinant His-tagged full-length XRCC4 was attached to Sulfolink Coupling Gel (Pierce, USA) and was used to immuno-affinity purify anti-XRCC4 antibodies from crude SJ4 serum as described previously (Lakin et al., 1996).

Phosphatase-treatment of HeLa Cell Extracts

To analyse for XRCC4 phosphorylation, HeLa nuclear extract (50 µg) was treated with λ protein phosphatase (New England Biolabs) in the presence of 2 mM $MnCl_2$ and incubated for 30 min at 30° C. prior to SDS-PAGE and Western blotting.

Co-immunoprecipitations and Ligase Adenylylation Assays

XRCC4 was immunoprecipitated from HeLa nuclear extract using polyclonal anti-XRCC4 and a pre-immune control. Specifically HeLa nuclear extract was dialysed into Buffer D* (20 mM HEPES-KOH, 20% (w/v) glycerol, 50 mM KCl, 2 mM $MgCl_2$, 0.2 mM EDTA, 1 mM DTT, 0.5 mM PMSF, 1 mM sodium metabisulphite and 0.1% NP-40) and then incubated with either pre-immune or immune serum for 1 h at 4° C. in the presence of 50 µg/ml ethidium bromide to disrupt non-specific interactions (Lai and Herr, 1992). Immune complexes were bound to protein A Sepharose beads (Pharmacia), followed by extensive washing with Buffer D* containing 0.15–1 M NaCl. The protein A Sepharose beads were finally washed in Buffer D* containing 0.15 M NaCl prior to analysis. The samples were then tested for the ability to form DNA ligase-adenylated complexes as described previously (Robins and Lindahl, 1996). The polynucleotide substrates oligodT.polyrA and oligorA.polydT were prepared as described (Tomkinson et al., 1991). The reactivity of the enzyme-adenylate intermediates formed was examined by adding 0.8 µg of unlabelled oligodT.polyrA or oligorA.polydT for 1 hr at 30° C. The reactions were stopped by the addition of SDS sample buffer and adenylylated proteins detected by autoradiography following SDS-PAGE.

Gel-filtration Chromatography

Total HeLa nuclear extract (6 mg protein) was dialysed extensively against Buffer A (50 mM Tris-HCl pH 7.5, 1 mM EDTA, 0.5 mM DTT, 10% (w/v) glycerol) containing 1 M NaCl. The protein was then loaded onto a Superose 6 (Pharmacia) column (60×1.5 cm) pre-equilibrated with Buffer A containing 1 M NaCl. On an identical gel-filtration run, 0.2 mg of pure untagged recombinant XRCC4 was analysed in buffer A containing 1 M NaCl.

Purification of DNA Ligase IV From HeLa Cells

DNA ligase IV was purified from HeLa cells as described previously (Robins, 1996). Fractions collected from each of the columns were analysed by immunoblots with antibodies specific for DNA ligases III and IV and XRCC4.

Expression of Recombinant Ligase IV Derivatives

For generation of recombinant ligase IV derivatives, fragments of the human ligase IV gene coding region were amplified by PCR from reverse transcribed HeLa RNA. Each PCR product included a Bam HI site at the 5' end and a stop codon followed by aSal I site at the 3' end, and after digestion were ligated into pET30b digested with Bam HI/Sal I. The 550–844 fragment of ligase IV was also cloned into pQE-30 and the resultant clone was expressed in *E. coli* M15(Rep4). For in vitro transcription and translation of ligase IV fragments, 1 µg of pET30LigIV(1–198), pET30LigIV(199–549), pET30LigIV(550–844) or a luciferase control (Promega) were transcribed in vitro and translated using the TnT rabbit reticulocyte lysate kit (Promega) according to the manufacturer's instructions. Resulting N-terminally His-tagged ligase IV products were purified by $Ni^{2+}$-NTA agarose chromatography.

Briefly, a 100 µl bed volume of Qiagen $Ni^{2+}$-NTA agarose was pre-equilibrated in wash buffer (50 mM Tris-HCl pH 7.5, 20 mM imidazole, 10% (w/v) glycerol and 0.5 M NaCl) prior to the addition of 20 µl of the crude [$^{35}$S]methionine-labelled in vitro translated ligase fragment. Unbound proteins were removed after low-speed centrifugation and the resin was washed 3 times with wash buffer to remove non-specifically bound proteins. Finally, ligase IV proteins were eluted with 100 µl of elution buffer consisting of 50 mM Tris-HCl pH 7.5, 100 mM imidazole and 10% (w/v) glycerol.

Interaction Assays Between Recombinant XRCC4 and Ligase IV Derivatives

Full-length XRCC4 was immobilized on Sepharose-4B gel beads (Pharmacia) using the cyanogen bromide method according to the manufacturer's instructions. As a negative control, coupling was also performed without XRCC4 protein. A 30 µl bed volume of beads (with and without XRCC4) was pre-equilibrated with Binding Buffer (50 mM Tris-HCl pH 7.5, 2 mM DTT, 1 mM EDTA, 10% (w/v) glycerol, 0.1% NP-40 and 0.36 mg/ml BSA) before the addition of the His-tag purified in vitro translated ligase products or luciferase. Unbound material was collected after centrifugation and the beads were washed with Binding Buffer containing 0.1 M NaCl and 1.0 M NaCl. The beads were resuspended in gel loading buffer and boiled in preparation for analysis by SDS-PAGE. Finally SDS-PAGE gels were fixed in 10% acetic acid for 30 min and dried, and labelled proteins were detected by autoradiography. The ability of the recombinant C-terminal fragment of ligase IV (residues 550–844) to bind XRCC4-Sepharose beads was tested as above, except that analysis was by Coomassie-brilliant blue staining and immunoblotting with the anti-ligase IV antibody.

EXAMPLE 2

DETERMINATION OF BIOLOGICAL ACTIVITY OF DNA LIGASE IV

Identification of a Second, Hitherto Uncharacterized, Yeast DNA Ligase

Using a consensus sequence within the core catalytic domain of all published DNA ligases the present inventors searched through the recently fully sequenced *S. cerevisiae* genome (Goffeau et al., 1996).

In addition to detecting CDC9, which encodes DNA ligase I, these searches identified an ORF (YOR005c) present on chromosome XV as a highly significant hit.

Figure 2:
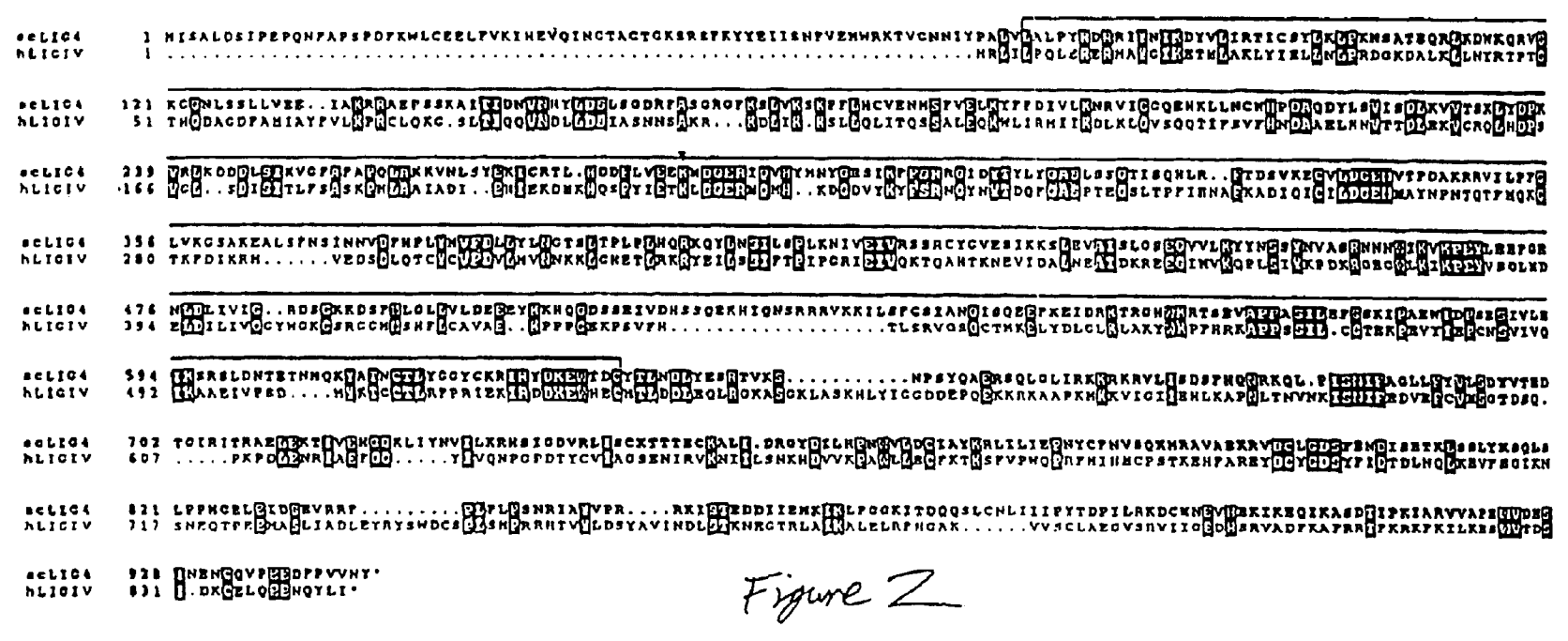

This ORF encodes a 944 amino acid residue polypeptide of predicted molecular mass of 109 kDa that exhibits extensive similarity (24% identity; 43% similarity) in its central region to the "core" ligase conserved domain of DNA ligase I (FIG. 2).

Phylogenetic analyses of protein alignments over this region reveal that YOR005c is considerably more related to DNA ligases of eukaryotes and eukaryotic viruses than to those of prokaryotes, and in particular, is most closely related to human ligase IV. A phenogram was generated using the PHYLIP package with the aligned "core" conserved sequence of each protein as designated in FIG. 2 using the UPGMA method. Accession numbers are as follows: *A. thaliana* I (X97924); *C. albicans* (X95001); *C. elegans* I (Z73970); Fowlpox virus (U00761); *H. sapiens* I (M36067), III (X84740) and IV (X83441); *M. musculus* I (U04674); *Rabbit fibroma* virus (Z29716); *S. cerevisiae* I (X03246), IV (Z74913); *S. pombe* I (X05107); T7 bacteriophage (P00969); Vaccinia virus (X16512); *X. laevis* I (L43496).

Consistent with this, YOR005c shares an N-terminal extension with the mammalian enzymes that is lacking in prokaryotic DNA ligases. Furthermore, it possesses an additional C-terminal extension that is homologous throughout its length to that of mammalian ligase IV. We thus conclude that YOR005c encodes a homologue of mammalian DNA ligase IV and designate this locus LIG4.

Disruption of LIG4 Does not Lead to Marked Hypersensitivity to a Variety of DNA-damaging Agents To study LIG4 function, we inactivated this gene in the haploid yeast strain W303α by a one-step gene disruption.

Notably, resulting lig4 mutants do not have readily observable growth defects when propagated at temperatures ranging from 18° C. to 37° C. This contrasts markedly with CDC9, the gene encoding yeast ligase I, whose disruption results in lethality due to an inability to progress through S-phase (Johnston and Nasmyth, 1978). It is thus concluded that LIG4 does not play an essential role in DNA replication, and that yeast ligase I is the only DNA ligase required for this process.

Figure 3A:
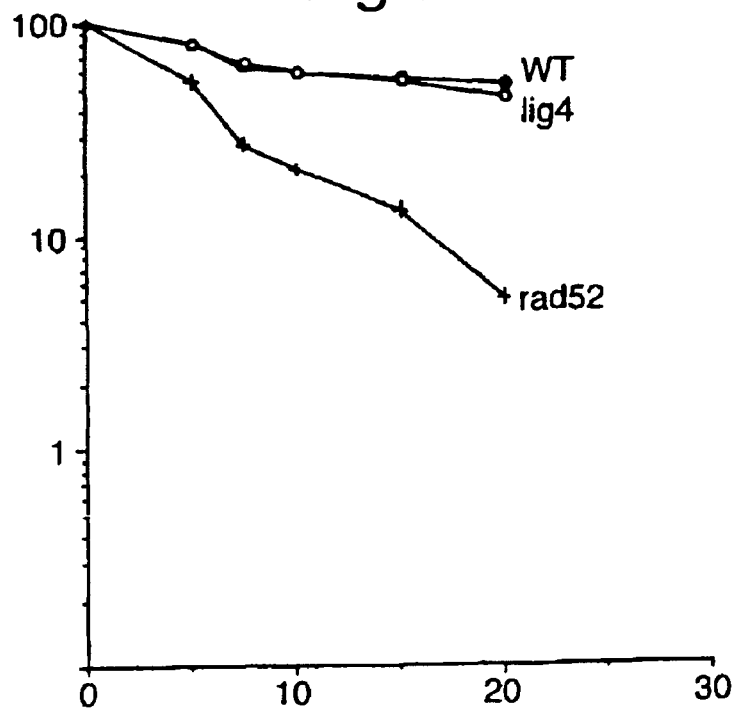
FIG. 3A shows % cell survival for wild-type, lig4 mutants and rad52 mutants at various doses in kRads of ionizing radiation.

Next, we tested whether lig4 mutant yeast are defective in any of the predominant DNA repair pathways by assessing their sensitivity to killing by various DNA damaging agents. Notably, lig4 mutant strains are not hypersensitive to DNA damage induced by exposure to ultraviolet radiation, showing that it is not essential in nucleotide excision repair. In addition, strains disrupted for LIG4 are not hypersensitive a range of concentrations of the radiomimetic drug, methyl methanesulfonate (MMS) in the growth medium. Finally, lig4 mutant yeasts also do not display significantly elevated sensitivity to killing by ionizing radiation at a range of doses (0–45 kRad). Unlike rad52 mutants, lig4 mutant yeast are as resistant to ionizing radiation as parental strains: lig4 mutants were not significantly more sensitive even at high doses (up to 45 kRad) (FIG. 3A).

Since radiation-induced DNA double-strand-breaks (DSBs) are repaired primarily by homologous recombination in *S. cerevisiae*, these data suggest that LIG4 is not essential for the latter process. Consistent with this, we have found that the efficiency of homologous recombination-mediated targeted integration into various loci in the yeast genome is indistinguishable between wild-type and lig4 mutant strains.

LIG4 Functions in the Ku-dependent NHEJ Pathway of DNA Double-strand Break Repair In *S. cerevisiae*, radiation-induced DNA double-strand breaks (DSBs) are repaired primarily by homologous recombination, which is mediated by genes in the RAD52 epistasis group (Friedberg et al., 1995). Thus, disruption of RAD52 sensitizes yeast cells to ionizing radiation (FIG. 3A). However, eukaryotic cells can also repair DNA DSBs by a second pathway, non-homologous end-joining (NHEJ), that utilizes gene products distinct from those employed in homologous recombination. In both yeast and mammals, one of these components is the DNA-binding protein Ku, comprising subunits of ~70 kDa and ~80 kDa [Ku70 and Ku80 in mammals (Jackson and Jeggo, 1995); Yku70p/Hdf1p and Yku80p/Hdf2p in yeast (Feldmann and Winnacker, 1993; Boulton and Jackson, 1996a; 1996b; Feldmann et al., 1996; Mages et al., 1996; Milne et al., 1996; Siede et al., 1996; Tsukamoto et al., 1996)]. NHEJ appears to be the predominant pathway for DSB repair in mammals but represents a minor pathway in yeast; consequently, disruption of *S. cerevisiae* YKU70 or YKU80 only results in significantly increased sensitivity to ionizing radiation or MMS when homologous recombination is inoperative (Boulton and Jackson, 1996a; 1996b; Milne et al., 1996; Siede et al., 1996).

Figure 3B:
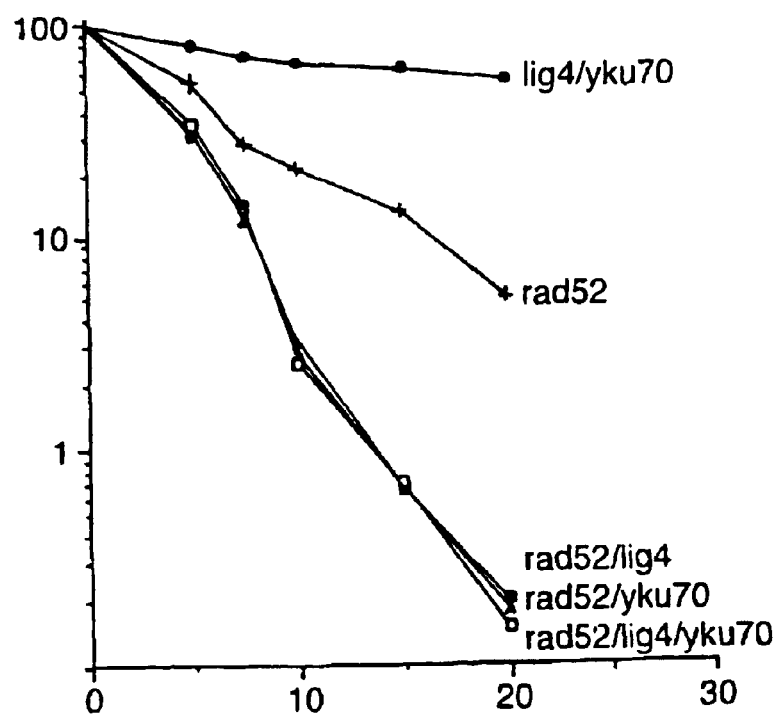
FIG. 3B shows % cell survival for lig4/yku70 mutants, rad52 mutants rad52/lig4 mutants, rad52/yku70 mutants and rad52/lig4/yku70 mutants at various doses in kRads of ionizing radiation.

We have found that lig4/rad52 double mutants are considerably more radiosensitive than are strains disrupted for RAD52 alone (FIG. 3B). As in the case for YKU70 (mutant in the Ku70 subunit of yeast Ku), disruption of LIG4 hypersensitizes yeast to ionizing radiation in rad52 mutant backgrounds. Furthermore, lig4/yku70/rad52 triple mutants are not appreciably more radiosensitive than are yku70/rad52 double mutant or lig4/rad52 double mutant strains, indicating that Lig4p and Yku70p function on the same RAD52-independent repair pathway. This provides indication that LIG4 is involved in the repair of ionizing radiation-induced DNA damage and that it functions in a RAD52-independent pathway.

Since the effects of disrupting LIG4 are similar to those obtained by disrupting YKU70 or YKU80, we assessed the radiosensitivity of lig4/yku70/rad52 triple mutants. Such mutant strains are no more sensitive to ionizing radiation than are the lig4/rad52 or yku70/rad52 mutant strains (FIG. 3B).

Taken together, these data provided indication that Ku and LIG4 function in the same DNA repair pathway.

Previous work has shown that Ku functions in DNA NHEJ and that this process can be measured through employing an in vivo plasmid repair assay (Boulton and Jackson, 1996a; 1996b; Milne et al., 1996). In this assay, a yeast—*E. coli* shuttle plasmid pBTM116 (Boulton and Jackson, 1996a; 1996b) is linearized by restriction enzyme digestion, then is introduced into *S. cerevisiae* by transformation. The plasmid contains the yeast selectable marker TRP1, the β-lactamase gene, the ADH1 promoter and EcoRI and PstI restriction sites. Since the plasmid must be recircularized to be propagated, the number of yeast transformant colonies obtained quantifies the ability of the strain to repair the plasmid. Furthermore, since the DNA DSB generated in these studies resides in a region that is not homologous to the yeast genome, homologous recombination is suppressed and repair operates predominantly via NHEJ.

We therefore analysed the ability of lig4 mutant yeasts to repair pBTM116 after cleavage with various restriction endonucleases. Wild-type, lig4, yku70 and lig4/yku70 yeast strains were used. Cells for each strain were transformed in parallel with supercoiled pBTM116 or with an equivalent amount of pBTM116 that had been digested to completion with EcoRI (left panel of FIG. 4) or PstI (right panel of FIG. 4). For each experiment, the value plotted is the number of transformants obtained with the linear plasmid expressed as a percentage of the number obtained for supercoiled DNA. Each experiment was repeated at least three times and, in each case, cells were plated and counted in duplicate.

As with strains disrupted for YKU70 or YKU80, lig4 mutant strains are severely impaired in plasmid NHEJ, and this is observed both with 5' or 3' overhanging DNA ends. Interestingly, these studies reveal that the effect of lig4 mutations is less pronounced with 3' overhanging DNA ends than it is with 5' overhanging ends. Although other alternatives exist, it is possible that this reflects differences in the mechanisms by which the two types of DNA ends can be repaired or is due to differential sensitivities of the different end structures to nuclease attack. Notably, DNA repair is not impaired further in yku70/lig4 double mutant strains (FIG. 4). In addition, although the precise reason for this effect is not known, as is the case for yku70 or yku80 mutants, we have found that lig4 mutant yeasts have a slightly elevated ability to rejoin pBTM116 bearing blunt-ends.

Taken together, these results reveal that Lig4p plays a crucial role in the repair of plasmid molecules bearing cohesive DNA double-strand breaks in vivo. Secondly, they show that, although purified DNA ligase I (CDC9) has been shown to be capable of catalysing DSB joining in vitro (Tomkinson et al., 1992), this enzyme does not play a major role in this pathway as assayed by in vivo plasmid DSB rejoining, and is unable to substitute efficiently for Lig4p in this process. Finally these results also show that Lig4p plays an important role in the Ku-dependent NHEJ pathway.

Although plasmid repair is reduced dramatically in lig4 mutant strains, it is not abolished. To determine precisely the types of DNA repair events that are dependent or independent of LIG4, repaired plasmids were recovered and then analysed by restriction enzyme digestion and DNA sequencing. In the absence of functional LIG4, the cohesive DNA termini are repaired by an inefficient error-prone DNA repair pathway. The plasmid pBTM116 contains the ADH1 promoter and some repair products were generated by the gap-repair process involving the chromosomal ADH1 gene. Of the large number of plasmids recovered from parental strains, all had been repaired by direct ligation of the cohesive DNA termini, thus regenerating the restriction enzyme cleavage site (Boulton and Jackson, 1996a; 1996b). Plasmid repair products recovered from yku70 or lig4 mutant strains, however, were found to fall into several categories. Some of these corresponded to "gap repair" products which we have shown are generated via RAD52-dependent homologous recombination with yeast genomic DNA (sequence analyses reveal that homologous recombination is employed in the generation of these products and their production is abolished by disruption of RAD52; Boulton and Jackson, 1996a; 1996b and data not shown). This therefore provides further evidence that LIG4, like YKU70 and YKU80, does not play a crucial role in homologous recombination processes. In yku70 or yku80 mutant strains, virtually all of the residual repair products were found to have suffered deletions (Boulton and Jackson, 1996a; 1996b). In contrast, although many of the residual repair products generated in lig4 mutants had also suffered deletion of terminal sequences, some were rejoined accurately.

Collectively, these results provide insights into the distinct roles performed by Lig4p and Ku in DNA NHEJ (see Discussion below).

Lig4p, Unlike Ku, Does Not Appear to Function in Telomere Length Maintenance

Telomeres occur at the ends of eukaryotic chromosomes, are structurally distinct, and have unusual replication intermediates for which it is unclear whether a distinct DNA ligase is necessary (Blackburn, 1991; Zakian, 1995; Lundblad and Wright, 1996). Recent work has demonstrated that Ku functions in telomere homeostasis, since disruption of either YKU70 or YKU80 results in a dramatic reduction in telomeric length (Boulton and Jackson, 1996b; Porter et al., 1996).

Given that Lig4p and Ku function together in DNA NHEJ, we tested whether LIG4 is involved in telomere length control.

To do this, yeast genomic DNA was digested with the restriction enzyme XhoI, which in wild-type strains produces a predominant telomeric fragment of ~1.3 kb that is detected by Southern hybridization to an oligonucleotide probe that binds to the repetitive telomeric sequences, including ~400 bp of repeating $(C_{1-3}A)$ sequence and is detected by Southern hybridization using a radiolabelled poly $(GT)_{20}$ oligonucleotide. Notably, whereas disruption of YKU70 results in telomeric shortening, loss of LIG4 function has no detectable effect.

These data therefore reveal that, although Ku and Lig4p function together in DNA DSB repair, Ku but not Lig4p has an additional essential function in telomere length homeostasis.

MATERIALS AND METHODS

Gene Disruptions

Full length LIG4 was amplified by PCR with primers LIG4-1 and LIG4-2 (5' TCAGTAGTTGACTACGG-GAAAGTCT 3' and 5' ATGATATCAGCACTAGATTC-TATAC 3', respectively) using the Expand High Fidelity DNA polymerase (Boehringer Mannheim). After cloning into pGEM-T (Promega), the resultant plasmid was digested with EcoRI, treated with Pfu DNA polymerase and then digested with XbaI. The HIS3 marker was inserted to replace the LIG4 ORF between residues 289 and 592. The disruption fragment was excised with SphI and SpeI and was used to transform the appropriate yeast strains to His$^+$. Gene disruption was verified by using LIG4 and HIS3 primers in PCR. Two RAD52 disruption constructs were provided by D. Weaver and have TRP1 and URA3 selection respectively.

Assessment of Sensitivity to Temperature and DNA Damaging Agents

Aliquots (15 µl) of serial 5-fold dilutions of mid-log phase yeast cultures were spotted onto YPDA plates and were grown for 36 h at 30° C. or 37° C. Strains on one plate were exposed to 50 J/m$^2$ ultraviolet (UV-C) radiation (Stratalinker; Stratagene). On another plate, YPDA medium contained 0.0025% methylmethanesulfonate. In other studies, lig4 mutant strains did not display hypersensitivity to MMS (0.0005% and 0.005% in the growth medium) nor to UV-C (20–150 J/m$^2$).

Ionizing Irradiation Survival Assays

Three independent isolates of each strain were inoculated either into minimal media lacking the appropriate amino acid(s) or into YPDA and were grown overnight at 30° C. Cultures were diluted in sterile water to an OD$_{600nm}$ value equivalent to 1×10$^7$ cells/ml and 1 ml aliquots were irradiated using a $^{137}$Cs source at a dose of 0.18 kRad/min. Irradiated samples and unirradiated controls were then diluted and plated in duplicate using an automated spiral plater (Whitley) on YPDA or minimal media. Colony numbers were ascertained following incubation at 30° C. for 3–4 days.

Plasmid Repair Assay

Plasmid repair assays were performed as described previously (Boulton and Jackson, 1996a; 1996b). Briefly, the yeast-*Escherichia coli* shuttle plasmid pBTM116 (2–5 µg), which contains TRP1 for selection in yeast, was digested with the appropriate restriction enzyme to completion and the enzyme was inactivated by treatment at 65° C. for 20 min. Linearized DNA was then used to transform yeast by the lithium acetate method (Ausubel et al., 1987). Parallel transformations were performed with an equivalent amount of uncut plasmid to enable normalisation for differences in transformation efficiency. Diluted samples were plated in duplicate on minimal media lacking the appropriate amino acids, and colonies were counted following incubation at 30° C. for 3–4 days. To analyse plasmid repair products, DNA from single yeast transformants was isolated via the Yeast DNA Isolation kit (Stratagene) and this was used to transform E. coli XL1-Blue cells (Stratagene) to ampicillin resistance. Plasmid DNA was then isolated and was analysed by restriction enzyme digestion and by DNA sequencing.

Yeast DNA Extraction and Analyses of Telomeric DNA

Genomic DNA from S. cerevisiae was isolated essentially as described (Ausubel et al., 1987). For telomere analyses, 2 µg of genomic DNA was digested with 30 U of XhoI (Boehringer Mannheim) at 37° C. overnight. The digested DNA was then separated on a 1.2% agarose 1×TAE gel and was transferred to Hybond Nfp+ membrane (Amersham) by capillary transfer in 20×SSC as suggested by the manufacturer. Membranes were pre-hybridized in 0.5 M sodium phosphate, pH 7.2, 1% SDS and then hybridized with 3 ng/ml of $^{32}$P-end-labelled poly $(GT)_{20}$ oligonucleotide (specific activity of >$10^9$/µg) in a Church-based buffer (0.2 M sodium phosphate, pH 7.2, 1% BSA, 6% polyethyleneglycol 6000, 1% SDS) overnight at 62° C. Finally, membranes were washed twice at room temperature for 30. min in 0.2 M sodium phosphate, 0.1% SDS, then exposed to pre-flashed X-ray film at −70° C.

DISCUSSION

The inventors' work with XRCC4 indicates that it is a predominantly nuclear protein. Moreover, through a variety of approaches, we have demonstrated that XRCC4 mediates extremely tight and specific interactions with DNA ligase IV. For example, these two components co-immunoprecipitate highly specifically with one another from HeLa cell extracts, even in the presence of 1 M NaCl. Furthermore, such interactions are not abrogated by ethidium bromide, indicating that the interaction between XRCC4 and ligase IV is not mediated by a DNA intermediate. Indeed, we show that bacterially expressed XRCC4 and ligase IV also bind to one another tightly, revealing that their interaction is direct. In addition, XRCC4 and ligase IV co-purify over every chromatographic fractionation procedure we have employed, including gel-filtration in the presence of 1 M NaCl, anion and cation exchange chromatography, and hydrophobic interaction chromatography. Indeed, so far we have only resolved these two proteins by the addition of harsh ionic detergents.

The fact that XRCC4 interacts tightly with ligase IV but not with the other DNA ligases that we have analysed has lead us to investigate the basis for this binding specificity. Notably, although all characterized mammalian DNA ligases contain a common highly related core catalytic region, each possesses unique N- and/or C-terminal extensions. We have found that it is the unique C-terminal domain and not the ligase catalytic region of ligase IV that interacts with XRCC4. Interestingly, this region of ligase IV contains two tandem copies of the weakly conserved BRCT homology domain (Koonin et al., 1996; Callebaut and Mornon, 1997), leading one to speculate that it is one or both of these domains that mediate the interaction with XRCC4. BRCT domains also exist in a variety of other factors and are required for those factors to interact (Mackey et al., 1997; Nash et al., 1997), suggesting that the BRCT domain of one protein interacts with a BRCT domain of the other. Thus, in light of our work showing interaction between XRCC4 and DNA ligase IV it might be expected that XRCC4 would also possess one or more copies of the BRCT consensus. Although XRCC4 has not been identified as a BRCT domain-containing protein by previous analyses, we have used manual and computer-aided inspections of the XRCC4 sequence to reveal limited homologies to other BRCT domains, suggesting that XRCC4 might contain one or more divergent copies of this putative protein structural unit.

Given that XRCC4 clearly functions in DNA NHEJ, our data indicate that DNA ligase IV also plays a crucial role in this process. XRCC4 may serve as a molecular bridge to target ligase IV to DNA DSBs, perhaps through XRCC4 also interacting with other components of the DNA NHEJ apparatus (FIG. 5). In regard to such a putative bridging function for XRCC4, it is worthy of note that immunoprecipitation studies suggest that XRCC4 can interact with Ku and/or DNA-PK$_{cs}$, although these interactions only occur at low salt concentrations and hence are weak compared to those exhibited between XRCC4 and ligase IV. A possible physical linkage between XRCC4 and DNA-PK is attractive in light of the fact that we have shown that HeLa cell XRCC4 is a phospho-protein and is an effective substrate for DNA-PK in vitro. Since XRCC4 possesses a DNA-PK kinase consensus motif (Li et al., 1995), mutation of this site may affect XRCC4 function in vivo.

Consistent with the proposal that ligase IV plays an important role in DNA DSB repair, we have identified a S. cerevisiae homologue of DNA ligase IV (displaying extensive sequence similarity along its length with mammalian DNA ligase IV) and have shown that inactivation of this factor debilitates DNA NHEJ in a manner that is epistatic with mutations in the yeast homologues of Ku70 and Ku80 (Boulton and Jackson, 1996; Boulton and Jackson, 1996; Teo and Jackson, 1997). By contrast, we find that yeast ligase IV does not appear to play an essential role in the repair of ultraviolet light-induced DNA damage nor in the repair of DNA DSBs by homologous recombination (Teo and Jackson, 1997). Taken together with the data on XRCC4, this provides indication that ligase IV is dedicated to DNA NHEJ and that this function is conserved throughout the eukaryotic kingdom.

The yeast gene, which we have designated LIG4, is not essential for DNA replication, RAD52-dependent homologous recombination nor the pathways of nucleotide excision repair and base excision repair. Instead, we have shown that LIG4 is specifically involved in the rejoining of DNA double-strand breaks by the process of DNA NHEJ, which does not demand homology between the two recombining DNA molecules and does not require RAD52. Notably, genetic epistasis experiments reveal that LIG4 acts in the same DNA repair pathway as Ku, a nuclear protein that specifically recognizes DNA strand breaks. We have thus identified a novel S. cerevisiae DNA ligase and have shown that it is involved specifically in the Ku-dependent NHEJ pathway of DNA DSB repair.

In light of this, and given that mutations in YKU70 or YKU80 result in dramatic telomeric shortening in yeast (Boulton et al., 1996b; Porter et al., 1996), we have also assessed the potential involvement of LIG4 in telomere length homeostasis. Telomeres are the protein-DNA structures at the ends of eukaryotic chromosomes that ensure the complete replication of chromosome ends, protect these ends from degradation, and prevent chromosomal termini from activating DNA damage signalling pathways or engaging in fusion and recombination reactions with other loci (for reviews (Blackburn, 1991; Zakian, 1995; Lundblad and Wright, 1996)). In most organisms, telomeres are composed of variable numbers of simple repeat sequences and, at least in S. cerevisiae, the length of these sequence arrays is maintained by a combination of telomerase activity and RAD52-dependent and -independent recombination. In yeast, deficiencies in Ku result in an approximately 70% reduction in the number of telomeric repeat sequences (Boulton et al., 1996b; Porter et al., 1996). Given that Ku binds to the ends of double-strand DNA (Mimori and Hardin, 1986; Paillard and Strauss, 1991), one possibility is that Ku may interact directly with telomeric DNA ends and potentiate telomere lengthening by protecting telomeric DNA termini from nucleases or by augmenting telomerase recruitment. An alternative explanation is that the effect of Ku inactivation on telomere length is indirect—perhaps the DNA repair defects that are associated with Ku deficient yeasts result in changes in cell physiology that impinge indirectly on telomere length control. Although it is not possible at present for us to identify precisely how Ku affects telomere length, the fact that mutations in LIG4 have essentially the same DNA repair defect as Ku but do not alter telomere length argues for a specific role for Ku in telomere homeostasis that is distinct from its activities in DNA DSB repair. In this regard, it will be of interest to see whether mutated derivatives of Ku can be generated that have no effect on DNA repair but do result in defective telomeric maintenance.

Yeast cells mutated in LIG4 have pronounced defects in DNA NHEJ, showing that Lig4p plays a crucial role in this process that cannot be complemented efficiently by yeast DNA ligase I. Conversely, yeast CDC9 and human DNA ligase I mutants are defective in DNA replication and, at least in vitro, this function is not performed efficiently by other enzymes. This indicates that yeast DNA ligases I and IV have distinct and largely separate cellular functions and cannot substitute effectively for one another. Thus, DNA ligase I plays a crucial role in DNA replication and also appears to seal single-strand DNA breaks that are the end-products of nucleotide- and base-excision repair, and moreover, is likely to complete recombination events between homologous duplex DNA molecules. There are also data suggesting that mammalian DNA ligase III is specialized towards particular functions. One splice variant (DNA ligase III-α) may operate in a separate pathway for base excision repair while another variant (DNA ligase III-β) has been implicated in meiotic recombination. Notably, there are no obvious homologues of mammalian DNA ligase II/III in S. cerevisiae. However, sequence analyses (FIG. 1; Colinas et al., 1990; Kerr et al., 1991; Husain et al., 1995) reveal that these ligases are related more closely to DNA ligases encoded by cytoplasmic poxviruses than they are to DNA ligase I, suggesting that ligases II and III may have arisen fairly recently in vertebrate evolution. Interestingly, and largely consistent with the proposed functions for mammalian ligase III, inactivation of poxvirus DNA ligase does not affect viral DNA replication or recombination but renders the mutant virus more sensitive to DNA damage induced by UV or bleomycin (Colinas et al., 1990; Kerr et al., 1991). Collectively, these data suggest that DNA ligase I and perhaps DNA ligase II/III are involved predominantly in the rejoining of single-stranded nicks whereas DNA ligase IV is the major enzyme catalysing the joining of double-stranded breaks.

In light of these points, and given that LIG4 functions in the highly evolutionarily conserved Ku-dependent NHEJ pathway, mammalian DNA ligase IV is indicated as having a key role in Ku-dependent DNA DSB rejoining. As is the case for Ku (reviewed in Jackson and Jeggo, 1995), deficiency in mammalian ligase IV may result in cellular radiosensitivity and an inability to rejoin site-specific V(D)J recombination intermediates.

Although the available data suggest diversification of function for the different eukaryotic DNA ligases, it is unclear whether this arises from intrinsic differences in catalytic activity or from differences conferred, for example, by the distinct C- and N-terminal extensions of the enzymes. At least in vitro, purified human DNA ligases I, III and IV show differing capacities to join single-stranded breaks in hybrid polynucleotide substrates (Arrand et al., 1986; Tomkinson et al., 1991; Robins and Lindahl, 1996). Furthermore, purified mammalian DNA ligases differ in their abilities to rejoin DNA DSBs. It is noteworthy, however, that in contrast with the available in vivo data, these studies show that purified ligase I but no other mammalian DNA ligase is able to catalyse the joining of blunt DNA ends effectively in vitro (Arrand et al., 1986; Tomkinson et al., 1991; Tomkinson et al., 1992; Robins and Lindahl, 1996). One possible explanation for this discrepancy between the in vitro and in vivo data is that at least some of the eukaryotic DNA ligases may not have high intrinsic affinity for DNA and, within the cell, are targeted to appropriate DNA lesions by accessory factors. Consistent with this is the identification herein of strong interaction between DNA ligase IV and XRCC4.

Inactivation of either yeast Ku or Lig4p both result in a similar dramatic reduction of NHEJ in the in vivo plasmid DNA DSB repair assay. Because of this and since the level of DNA repair does not fall further in yeast strains defective in both Ku and Lig4p, we conclude that these two factors function in the same illegitimate recombination pathway. However, it is apparent that Ku and Lig4p have distinct functions in DNA NHEJ, as evidenced by the different spectra of residual plasmid repair products that are generated in the respective mutant strains. Thus, whereas nearly all the residual plasmid repair products arising in yku70 mutants suffer deletions, in lig4 mutant strains these correspond to a mixture of deletion products and products generated by accurate DNA end-joining. Collectively, these results suggest that Ku may function in at least two ways to potentiate DNA repair. Firstly, it may protect exposed DNA ends from nuclease attack. Secondly, it might serve to specifically recruit Lig4p, directly or indirectly, to the sites of DNA damage, perhaps via the Lig4p C-terminal extension that is absent from DNA ligase I. Consequently, the phenotypes of strains defective in Ku or Lig4p can both be explained to result from an inability to target a ligase to DNA DSBs efficiently. In Ku deficient strains, the ready access of nucleases to the DNA ends may lead to deletions in virtually all the residual NHEJ repair products, which presumably arise via inefficient DNA end joining by untargeted ligase I or Lig4p. In contrast, when Lig4p is absent, Ku is still able to protect the DNA ends and this can explain how some accurate repair can still occur—this presumably being mediated by DNA ligase I. However, the reduced repair kinetics in lig4 mutant yeast may mean that, even in the presence of Ku, nucleases ultimately gain access to the DNA termini and lead deletions in a large proportion of the residual repair products. Consistent with the above model, we find that virtually all of the residual NHEJ products generated in yku70/lig4 double mutants have sustained terminal deletions.

Interaction Between XRCC4 and Ku/DNA-PKcs Complex

XRCC4 interaction with DNA-PKcs/Ku was demonstrated by incubation of HeLa cell nuclear extract with anti-XRCC4 or pre-immune antiserum with purification of the resulting immunocomplexes by adsoprtion onto protein A-Sepharose, then analysis by Western immunoblotting.

Both DNA-PKcs and the two subunits of Ku are immunoprecipitated by the anti-XRCC4 antiserum but not the pre-immune serum.

In these studies, immunocomplexes were washed under relatively mild conditions of 0.25 M NaCl and 0.1% Nonidet-P40. However, when more stringent washes were employed (for example, in the presence of 1 M NaCl, 0.1% Nonidet-P40 and 50 μg/ml ethidium bromide) the interaction between XRCC4 and Ku/DNA-PKcs complex was abolished.

Taken together, these data reveal that although the interaction between Ku/DNA-PKcs and XRCC4 appears specific, it is relatively weak.

The interaction may be inhibited using appropriate agents, including peptide fragments of the respective proteins. Such agents may be identified and obtained using assay methods and used in therapeutic and other contexts, as disclosed above.

REFERENCES

Araki, et al., (1997). *Proc. Natl. Acad. Sci. USA* 94, 2438–2443.
Arrand, et al., (1986) *J. Biol. Chem.*, 261, 9079–9082
Ausubel, et al., (1987) *Current Protocols in Molecular Biology* K. Janssen, Eds., Current Protocols (Green Publishing Associates, Inc. and John Wiley & Sons, Inc.)
Barnes, et al., (1992). *Cell* 69, 495–503.
Blackburn, E. H. (1991) *Nature*, 350, 569–573
Blunt, et al., (1995). *Cell* 90, 813–823.
Blunt, et al., (1996). *Proc. Natl. Acad. Sci. USA* 93, 10285–10290.
Boubnov, (1995). *Proc. Natl. Acad. Sci. USA* 92, 890–894.
Boulton, S. J. and Jackson, S. P. (1996b) *Nucl. Acids Res.*, 24, 4639–4648
Boulton, S. J. and Jackson, S. P. (1996a) *EMBO J.*, 15, 5093–5103
Caldecott, et al., (1996). *Nucleic Acids. Res.* 24, 4387–4394.
Caldecott, et al., (1994). *Mol. Cell. Biol.* 14, 68–76.
Callebaut, I. and Mornon, J. P. (1997) *FEBS Lett.*, 400, 25–30
Chen, et al., (1995). *Mol. Cell. Biol.* 15, 5412–5422.
Colinas, et al., (1990) *Virology*, 179, 267–275
Creissen, D. and Shall, S. (1982) *Nature*, 296, 271–272
Critchlow et al., (1997) *Curr. Biol.* 7, 588–598.
Danska, et al., (1996). *Mol. Cell. Biol.* 16, 5507–5517.
Dolganov, et al., (1996) *Mol. Cell. Biol.*, 16, 4832–4841
Feldmann, H. and Winnacker, E. L. (1993) *J. Biol. Chem.*, 268, 12895–12900.
Feldmann, et al., (1996) *J. Biol. Chem.*, 271, 27765–27769
Finnie, et al., (1996). *Phil. Trans. R. Soc. Lond. B* 351, 173–179.
Finnie, et al., (1995). *Proc. Natl. Acad. Sci. USA* 92, 320–324.
Friedberg, et al., (1995) *DNA Repair and Mutagenesis* (American Society of Microbiology Press, Washington, DC)
Getts, R. C. and Stamato, T. D. (1994). *J. Biol. Chem.* 269, 15981–15984.
Goffeau, et al. (1996) *Science*, 274, 546
Grawunder, et al., (1997) *Nature* 398, 492–495.
Hartley, et al., (1995). *Cell* 82, 849–856.
Henderson, et al., (1985) *Proc. Natl. Acad. Sci. USA*, 82, 2044–2048
Husain, et al., (1995). *J. Biol. Chem.* 270, 9683–9690.
Jackson, S. P. (1997). *Int. J. Biochem. Cell. Biol.*
Jackson, S. P. and Jeggo, P. A. (1995). *TIBS* 20, 412–415.
Jeggo, et al., (1995). *BioEssays* 17, 949–957.
Jessberger, et al., (1993) *J. Biol. Chem.*, 268, 15070–15079
Johnston, L. H. and Nasmyth, K. A. (1978) *Nature*, 274, 891–893
Kerr, et al., (1991) *EMBO J.*, 10, 4343–4350
Kirchgessner, et al., (1995). *Science* 267, 1178–1183.
Koonin, et al., (1996) *Nature Genetics*, 13, 266–268.
Kubota, et al., (1996) *EMBO J.*, 15, 6662–6670
Lai, J.-S. and Herr, W. (1992). *Proc. Natl. Acad. Sci. USA* 89, 6958–6962.
Lakin, et al., (1996). *Oncogene* 13, 2707–2716.
Lasko, et al., (1990). *J. Biol. Chem.* 265, 12618–12622.
Lehmann, et al., (1988) *Cancer Res.*, 48, 6343–6347
Li, et al., (1994) *Nucl. Acids Res.*, 22, 632–638
Li, et al., (1995). *Cell* 83, 1079–1089.
Lieber, et al., (1997). *Current Opinions in Genetics and Development* 7, 99–104.
Lieber, M. R. (1996). *Current Biology* 6, 134–136.
LindAhl, T. and Barnes, D. E. (1992) *Ann. Rev. Biochem.*, 61, 251–281
Lundblad, V. and Wright, W. E. (1996) *Cell*, 87, 369–375
Mackenny, et al., (1997). *J. Biol. Chem.* 272, 11550–11556.
Mackey, et al., (1997). *Mol. Cell. Biol.* 17, 989–998.
Mages, et al., (1996) *J. Biol. Chem.*, 271, 7910–7915
Malkas, et al., (1990) *Biochemistry*, 29, 6362–6374
Milne, et al., (1996) *Mol. Cell. Biol.*, 16, 4189–4198
Mimori, T. and Hardin, J. A. (1986) *J. Biol. Chem.*, 261, 10375–10379
Mizuta, et al., (1996). *International Immunology* 8, 1467–1471.
Mizuta, et al., (1997). *Internationl Immunology* 9, 1607–1613.
Montecucco, (1995) *EMBO J.* 14, 5379–5386
Nash, et al., (1997). XRCC1 protein interacts with one of two distinct forms of DNA ligase III. submitted to Biochemistry
Otevrel, T. and Stamato, T. D. (1995). *Genomics* 27, 211–214.
Oliver, S. (1996) *Trends Genet.*, 12, 241–242
Paillard, S. and Strauss, F. (1991) *Nucl. Acids Res.*, 19, 5619–5624
Peterson, et al., (1995). *Proc. Natl. Acad. Sci. USA* 92, 3171–3174.
Petrini, et al., (1995). *Mol. Cell. Biol.* 15, 4303–4308.
Poltoratsky et al. (1995) *The Journal Of Imunology*, 4529–4533.
Porter, et al., (1996) *Nucl. Acids Res.*, 24, 582–585
Prigent, et al., (1994) *Mol. Cell. Biol.*, 14, 310–317
Ramsden, et al., (1997). *Current Opinion in Immunology* 8, 114–120.
Rathmell, W. K. and Chu, G. (1994). *Mol. Cell. Biol.* 14, 4741–4748.
Roberts, et al., (1994) *J. Biol. Chem.*, 269, 3789–3792
Robins, P. and Lindahl, T. (1996) *J. Biol. Chem.*, 271, 24257–24261
Roth, et al., (1995). *Current Biology* 5, 496–499.
Schwartz, et al., (1996). *Mutation Res.* 351, 53–60.
Siede, et al., (1996) *Genetics*, 142, 91–102
Singleton, et al., (1997). *Mol. Cell. Biol.* 17, 1264–1273.
Smider, et al., (1994). *Science* 266, 288–291.
Taccioli, et al., (1994). *Science* 265, 1442–1445.
Teo, S.-H. and Jackson, S. P. (1997). *EMBO J.* 16: 4788–4795.

Thompson, et al., (1990). *Mol. Cell. Biol.* 10, 6160–6171.
Tomkinson, et al., (1991). *J. Biol. Chem.* 266, 21728–21735.
Tomkinson, et al., (1992) *Biochemistry*, 31, 11762–11771
Tsukamoto, et al., (1996) *Nucl. Acids Res.*, 24, 2067–2072

Waga, et al., (1994). *J. Biol. Chem.* 269, 10923–10934.
Wang, et al., (1994) *J. Biol. Chem.*, 269, 31923–31928
Wei, et al., (1995). *Mol. Cell. Biol.* 15, 3206–3216.
Zakian, V. A. (1995) *Science*, 270, 1601–1607

---

What is claimed is:

1. A screening method for identifying a compound which inhibits the binding between XRCC4 (XR-1 Cell Complementing 4) and DNA ligase IV, or XRCC4 and DNA-$PK_{cs}$/Ku (DNA-dependent Protein Kinase catalytic subunit/Ku), or XRCC4, DNA ligase IV and DNA-$PK_{cs}$/Ku, the method comprising the steps of:

(i) contacting XRCC4 with a test compound and one or more components selected from the group consisting of DNA ligase IV and DNA-$PK_{cs}$/Ku; under conditions wherein, in the absence of said test compound being a compound which inhibits binding of XRCC4 to said one or more compounds, said XRCC4 binds to said one or more components; and (ii) determining binding between said XRCC4 and said one or more components;

wherein reduction or abolition in binding between said XRCC4 and said one or more components is indicative that said test compound is a compound which inhibits binding between XRCC4 and DNA ligase IV, or XRCC4 and DNA-$PK_{cs}$/Ku or XRCC4, DNA ligase IV and DNA-$PK_{cs}$/Ku.

2. A screening method for identifying a compound which inhibits DNA ligase IV activity, the method including the steps of:

(i) contacting DNA ligase IV, XRCC4 and a test compound; and (ii) determining DNA ligase activity in the presence and the absence of test compound X, wherein a decrease in the activity in the presence relative to the absence of test compound is indicative that said test compound is a compound which inhibits the activity of DNA ligase IV.

3. A screening method for identifying a compound which inhibits the phosphorylation of XRCC4 by DNA-$PK_{cs}$ comprising (i) contacting a test compound, DNA-$PK_{cs}$ and XRCC4; and (ii) determining phosphorylation of said XRCC4 in the presence and the absence of the test compound;

a decrease in phosphorylation in the presence relative to the absence of the test compound being indicative that said test compound inhibits the phosphorylation of XRCC4 by DNA-$PK_{cs}$.

* * * * *

SEQUENCE LISTING

<160> NUMBER OF SEQ ID NOS: 18

<210> SEQ ID NO 1
<211> LENGTH: 944
<212> TYPE: PRT
<213> ORGANISM: Saccharomyces cerevisiae

<400> SEQUENCE: 1

```
Met Ile Ser Ala Leu Asp Ser Ile Pro Glu Pro Gln Asn Phe Ala Pro
  1               5                  10                  15

Ser Pro Asp Phe Lys Trp Leu Cys Glu Glu Leu Phe Val Lys Ile His
             20                  25                  30

Glu Val Gln Ile Asn Gly Thr Ala Gly Thr Gly Lys Ser Arg Ser Phe
         35                  40                  45

Lys Tyr Tyr Glu Ile Ile Ser Asn Phe Val Glu Met Trp Arg Lys Thr
     50                  55                  60

Val Gly Asn Asn Ile Tyr Pro Ala Leu Val Leu Ala Leu Pro Tyr Arg
 65                  70                  75                  80

Asp Arg Arg Ile Tyr Asn Ile Lys Asp Tyr Val Leu Ile Arg Thr Ile
                 85                  90                  95

Cys Ser Tyr Leu Lys Leu Pro Lys Asn Ser Ala Thr Glu Gln Arg Leu
                100                 105                 110

Lys Asp Trp Lys Gln Arg Val Gly Lys Gly Asn Leu Ser Ser Leu
            115                 120                 125

Leu Val Glu Glu Ile Ala Lys Arg Arg Ala Glu Pro Ser Ser Lys Ala
    130                 135                 140

Ile Thr Ile Asp Asn Val Asn His Tyr Leu Asp Ser Leu Ser Gly Asp
145                 150                 155                 160

Arg Phe Ala Ser Gly Arg Gly Phe Lys Ser Leu Val Lys Ser Lys Pro
                165                 170                 175

Phe Leu His Cys Val Glu Asn Met Ser Phe Val Glu Leu Lys Tyr Phe
                180                 185                 190

Phe Asp Ile Val Leu Lys Asn Arg Val Ile Gly Gly Gln Glu His Lys
            195                 200                 205

Leu Leu Asn Cys Trp His Pro Asp Ala Gln Asp Tyr Leu Ser Val Ile
    210                 215                 220

Ser Asp Leu Lys Val Val Thr Ser Lys Leu Tyr Asp Pro Lys Val Arg
225                 230                 235                 240

Leu Lys Asp Asp Asp Leu Ser Ile Lys Val Gly Phe Ala Phe Ala Pro
                245                 250                 255

Gln Leu Ala Lys Lys Val Asn Leu Ser Tyr Glu Lys Ile Cys Arg Thr
                260                 265                 270

Leu His Asp Asp Phe Leu Val Glu Glu Lys Met Asp Gly Glu Arg Ile
            275                 280                 285

Gln Val His Tyr Met Asn Tyr Gly Glu Ser Ile Lys Phe Phe Ser Arg
    290                 295                 300

Arg Gly Ile Asp Tyr Thr Tyr Leu Tyr Gly Ala Ser Leu Ser Ser Gly
305                 310                 315                 320

Thr Ile Ser Gln His Leu Arg Phe Thr Asp Ser Val Lys Glu Cys Val
```

-continued

```
                325                 330                 335
Leu Asp Gly Glu Met Val Thr Phe Asp Ala Lys Arg Val Ile Leu
            340                 345                 350
Pro Phe Gly Leu Val Lys Gly Ser Ala Lys Glu Ala Leu Ser Phe Asn
            355                 360                 365
Ser Ile Asn Asn Val Asp Phe His Pro Leu Tyr Met Val Phe Asp Leu
    370                 375                 380
Leu Tyr Leu Asn Gly Thr Ser Leu Thr Pro Leu Pro Leu His Gln Arg
385                 390                 395                 400
Lys Gln Tyr Leu Asn Ser Ile Leu Ser Pro Leu Lys Asn Ile Val Glu
                405                 410                 415
Ile Val Arg Ser Ser Arg Cys Tyr Gly Val Glu Ser Ile Lys Lys Ser
                420                 425                 430
Leu Glu Val Ala Ile Ser Leu Gly Ser Glu Gly Val Val Leu Lys Tyr
                435                 440                 445
Tyr Asn Ser Ser Tyr Asn Val Ala Ser Arg Asn Asn Asn Trp Ile Lys
    450                 455                 460
Val Lys Pro Glu Tyr Leu Glu Glu Phe Gly Glu Asn Leu Asp Leu Ile
465                 470                 475                 480
Val Ile Gly Arg Asp Ser Gly Lys Lys Asp Ser Phe Met Leu Gly Leu
                485                 490                 495
Leu Val Leu Asp Glu Glu Tyr Lys Lys His Gln Gly Asp Ser Ser
                500                 505                 510
Glu Ile Val Asp His Ser Ser Gln Glu Lys His Ile Gln Asn Ser Arg
                515                 520                 525
Arg Arg Val Lys Lys Ile Leu Ser Phe Cys Ser Ile Ala Asn Gly Ile
    530                 535                 540
Ser Gln Glu Glu Phe Lys Glu Ile Asp Arg Lys Thr Arg Gly His Trp
545                 550                 555                 560
Lys Arg Thr Ser Glu Val Ala Pro Pro Ala Ser Ile Leu Glu Phe Gly
                565                 570                 575
Ser Lys Ile Pro Ala Glu Trp Ile Asp Pro Ser Glu Ser Ile Val Leu
                580                 585                 590
Glu Ile Lys Ser Arg Ser Leu Asp Asn Thr Glu Thr Asn Met Gln Lys
                595                 600                 605
Tyr Ala Thr Asn Cys Thr Leu Tyr Gly Gly Tyr Cys Lys Arg Ile Arg
                610                 615                 620
Tyr Asp Lys Glu Trp Thr Asp Cys Tyr Thr Leu Asn Asp Leu Tyr Glu
625                 630                 635                 640
Ser Arg Thr Val Lys Ser Asn Pro Ser Tyr Gln Ala Glu Arg Ser Gln
                645                 650                 655
Leu Gly Leu Ile Arg Lys Lys Arg Val Leu Ile Ser Asp Ser
                660                 665                 670
Phe His Gln Asn Arg Lys Gln Leu Pro Ile Ser Asn Ile Phe Ala Gly
    675                 680                 685
Leu Leu Phe Tyr Val Leu Ser Asp Tyr Val Thr Glu Asp Thr Gly Ile
    690                 695                 700
Arg Ile Thr Arg Ala Glu Leu Glu Lys Thr Ile Val Glu His Gly Gly
705                 710                 715                 720
Lys Leu Ile Tyr Asn Val Ile Leu Lys Arg His Ser Ile Gly Asp Val
                725                 730                 735
Arg Leu Ile Ser Cys Lys Thr Thr Thr Glu Cys Lys Ala Leu Ile Asp
                740                 745                 750
```

-continued

```
Arg Gly Tyr Asp Ile Leu His Pro Asn Trp Val Leu Asp Cys Ile Ala
            755                 760                 765

Tyr Lys Arg Leu Ile Leu Ile Glu Pro Asn Tyr Cys Phe Asn Val Ser
            770                 775                 780

Gln Lys Met Arg Ala Val Ala Glu Lys Arg Val Asp Cys Leu Gly Asp
785                 790                 795                 800

Ser Phe Glu Asn Asp Ile Ser Glu Thr Lys Leu Ser Ser Leu Tyr Lys
            805                 810                 815

Ser Gln Leu Ser Leu Pro Pro Met Gly Glu Leu Glu Ile Asp Ser Glu
            820                 825                 830

Val Arg Arg Phe Pro Leu Phe Leu Phe Ser Asn Arg Ile Ala Tyr Val
            835                 840                 845

Pro Arg Arg Lys Ile Ser Thr Glu Asp Asp Ile Ile Glu Met Lys Ile
            850                 855                 860

Lys Leu Phe Gly Gly Lys Ile Thr Asp Gln Gln Ser Leu Cys Asn Leu
865                 870                 875                 880

Ile Ile Ile Pro Tyr Thr Asp Pro Ile Leu Arg Lys Asp Cys Met Asn
            885                 890                 895

Glu Val His Glu Lys Ile Lys Glu Gln Ile Lys Ala Ser Asp Thr Ile
            900                 905                 910

Pro Lys Ile Ala Arg Val Val Ala Pro Glu Trp Val Asp His Ser Ile
            915                 920                 925

Asn Glu Asn Cys Gln Val Pro Glu Glu Asp Phe Pro Val Val Asn Tyr
            930                 935                 940

<210> SEQ ID NO 2
<211> LENGTH: 844
<212> TYPE: PRT
<213> ORGANISM: Homo sapiens

<400> SEQUENCE: 2

Met Arg Leu Ile Leu Pro Gln Leu Glu Arg Glu Arg Met Ala Tyr Gly
  1               5                  10                  15

Ile Lys Glu Thr Met Leu Ala Lys Leu Tyr Ile Glu Leu Leu Asn Leu
            20                  25                  30

Pro Arg Asp Gly Lys Asp Ala Leu Lys Leu Leu Asn Tyr Arg Thr Pro
        35                  40                  45

Thr Gly Thr His Gly Asp Ala Gly Asp Phe Ala Met Ile Ala Tyr Phe
    50                  55                  60

Val Leu Lys Pro Arg Cys Leu Gln Lys Gly Ser Leu Thr Ile Gln Gln
65                  70                  75                  80

Val Asn Asp Leu Leu Asp Ser Ile Ala Ser Asn Asn Ser Ala Lys Arg
                85                  90                  95

Lys Asp Leu Ile Lys Lys Ser Leu Leu Gln Leu Ile Thr Gln Ser Ser
            100                 105                 110

Ala Leu Glu Gln Lys Trp Leu Ile Arg Met Ile Ile Lys Asp Leu Lys
        115                 120                 125

Leu Gly Val Ser Gln Gln Thr Ile Phe Ser Val Phe His Asn Asp Ala
    130                 135                 140

Ala Glu Leu His Asn Val Thr Thr Asp Leu Glu Lys Val Cys Arg Gln
145                 150                 155                 160

Leu His Asp Pro Ser Val Gly Leu Ser Asp Ile Ser Ile Thr Leu Phe
                165                 170                 175

Ser Ala Ser Lys Pro Met Leu Ala Ala Ile Ala Asp Ile Glu His Ile
```

-continued

```
                180                 185                 190
Glu Lys Asp Met Lys His Gln Ser Phe Tyr Ile Glu Thr Lys Leu Asp
            195                 200                 205
Gly Glu Arg Met Gln Met His Lys Asp Gly Asp Val Tyr Lys Tyr Phe
        210                 215                 220
Ser Arg Asn Gly Tyr Asn Tyr Thr Asp Gln Phe Gly Ala Ser Pro Thr
225                 230                 235                 240
Glu Gly Ser Leu Thr Pro Phe Ile His Asn Ala Phe Lys Ala Asp Ile
                245                 250                 255
Gln Ile Cys Ile Leu Asp Gly Glu Met Met Ala Tyr Asn Pro Asn Thr
            260                 265                 270
Gln Thr Phe Met Gln Lys Gly Thr Lys Phe Asp Ile Lys Arg Met Val
        275                 280                 285
Glu Asp Ser Asp Leu Gln Thr Cys Tyr Cys Val Phe Asp Val Leu Met
290                 295                 300
Val Asn Asn Lys Lys Leu Gly His Glu Thr Leu Arg Lys Arg Tyr Glu
305                 310                 315                 320
Ile Leu Ser Ser Ile Phe Thr Pro Ile Pro Gly Arg Ile Glu Ile Val
                325                 330                 335
Gln Lys Thr Gln Ala His Thr Lys Asn Glu Val Ile Asp Ala Leu Asn
            340                 345                 350
Glu Ala Ile Asp Lys Arg Glu Glu Gly Ile Met Val Lys Gln Pro Leu
        355                 360                 365
Ser Ile Tyr Lys Pro Asp Lys Arg Gly Glu Gly Trp Leu Lys Ile Lys
370                 375                 380
Pro Glu Tyr Val Ser Gly Leu Met Asp Glu Leu Asp Ile Leu Ile Val
385                 390                 395                 400
Gly Gly Tyr Trp Gly Lys Gly Ser Arg Gly Met Met Ser His Phe
                405                 410                 415
Leu Cys Ala Val Ala Glu Lys Pro Pro Gly Glu Lys Pro Ser Val
            420                 425                 430
Phe His Thr Leu Ser Arg Val Gly Ser Gly Cys Thr Met Lys Glu Leu
        435                 440                 445
Tyr Asp Leu Gly Leu Lys Leu Ala Lys Tyr Trp Lys Pro Phe His Arg
450                 455                 460
Lys Ala Pro Pro Ser Ser Ile Leu Cys Gly Thr Glu Lys Pro Glu Val
465                 470                 475                 480
Tyr Ile Glu Pro Cys Asn Ser Val Ile Val Gln Ile Lys Ala Ala Glu
                485                 490                 495
Ile Val Pro Ser Asp Met Tyr Lys Thr Gly Cys Thr Leu Arg Phe Pro
            500                 505                 510
Arg Ile Glu Lys Ile Arg Asp Asp Lys Glu Trp His Glu Cys Met Thr
        515                 520                 525
Leu Asp Asp Leu Glu Gln Leu Arg Gly Lys Ala Ser Gly Lys Leu Ala
530                 535                 540
Ser Lys His Leu Tyr Ile Gly Gly Asp Glu Pro Gln Glu Lys Lys
545                 550                 555                 560
Arg Lys Ala Ala Pro Lys Met Lys Lys Val Ile Gly Ile Ile Glu His
                565                 570                 575
Leu Lys Ala Pro Asn Leu Thr Asn Val Asn Lys Ile Ser Asn Ile Phe
            580                 585                 590
Glu Asp Val Glu Phe Cys Val Met Ser Gly Thr Asp Ser Gln Pro Lys
        595                 600                 605
```

```
Pro Asp Leu Glu Asn Arg Ile Ala Glu Phe Gly Gly Tyr Ile Val Gln
    610                 615                 620

Asn Pro Gly Pro Asp Thr Tyr Cys Val Ile Ala Gly Ser Glu Asn Ile
625                 630                 635                 640

Arg Val Lys Asn Ile Ile Leu Ser Asn Lys His Asp Val Val Lys Pro
            645                 650                 655

Ala Trp Leu Leu Glu Cys Phe Lys Thr Lys Ser Phe Val Pro Trp Gln
            660                 665                 670

Pro Arg Phe Met Ile His Met Cys Pro Ser Thr Lys Glu His Phe Ala
        675                 680                 685

Arg Glu Tyr Asp Cys Tyr Gly Asp Ser Tyr Phe Ile Asp Thr Asp Leu
    690                 695                 700

Asn Gln Leu Lys Glu Val Phe Ser Gly Ile Lys Asn Ser Asn Glu Gln
705                 710                 715                 720

Thr Pro Glu Glu Met Ala Ser Leu Ile Ala Asp Leu Glu Tyr Arg Tyr
            725                 730                 735

Ser Trp Asp Cys Ser Pro Leu Ser Met Phe Arg Arg His Thr Val Tyr
            740                 745                 750

Leu Asp Ser Tyr Ala Val Ile Asn Asp Leu Ser Thr Lys Asn Glu Gly
        755                 760                 765

Thr Arg Leu Ala Ile Lys Ala Leu Glu Leu Arg Phe His Gly Ala Lys
    770                 775                 780

Val Val Ser Cys Leu Ala Glu Gly Val Ser His Val Ile Gly Glu
785                 790                 795                 800

Asp His Ser Arg Val Ala Asp Phe Lys Ala Phe Arg Arg Thr Phe Lys
            805                 810                 815

Arg Lys Phe Lys Ile Leu Lys Glu Ser Trp Val Thr Asp Ser Ile Asp
            820                 825                 830

Lys Cys Glu Leu Gln Glu Glu Asn Gln Tyr Leu Ile
        835                 840

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 3
tcagtagttg actacgggaa agtct                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
atgatatcag cactagattc tatac                                          25

<210> SEQ ID NO 5
<211> LENGTH: 3323
<212> TYPE: DNA
<213> ORGANISM: Saccharomyces cerevisiae

<400> SEQUENCE: 5
attttttcct taagttaatt gactggccaa tcttttgaat ataattgcgc atcttccact    60
```

-continued

```
cttattgata aacgttacgg aagtatttaa tgtacatatg taggatagta ttaaataaac    120
ttcaaaaaat taagcctccg caaaacgcac catcagtagt tgactacggg gaagtcttct    180
tcaggcactt gacagttttc attaatagaa tgatccaccc attcaggggc aacgaccctg    240
gctattttcg gtatagtatc agaagccttt atttgttctt ttatttttc gtgtacctca     300 ttcatgcagt cttcctcaa aataggatca gtatatggta taattattaa gttacaaagt    360
gactgttgat ctgttatttt tccaccaaac aacttaattt tcatttctat aatgtcatct    420
tctgtgctaa ttttgcgacg tggtacgtat gcaatcctgt tggagaataa aaataatgga    480
aaccgccgaa cctcagaatc tatctcgagt tcccccatcg gtggtagact tagttgtgat    540
ttatacaatg atgacagttt ggtttccgaa atgtcatttt caaaactatc acccaaacaa    600 tctaccctt tttcagcgac ggctctcatt ttttgagaga cgttaaagca ataattgggc     660
tcgatcagga tgagcctctt atatgctata caatcgagta cccaatttgg gtgcaatata    720
tcatatcctc gatctattaa agccttgcat tccgtggtag ttttacagct gattaaccga    780
acgtccccaa ttgaatgacg ttttaaaatt acattatata tcagtttacc accatgttcc    840
acaatagttt tttcaagttc tgcccgtgta atccgtattc cagtgtcctc cgtgacatag    900
tcagagagaa cataaaaaag taatccggca aagatgtttg aaattggcag ttgtttcctg    960
ttttggtgaa agctgtctga aataagtact ctctttctct ttttccgtat caatccaagc   1020
tgtgaccttt ccgcttgata gctggggtta gatttaaccg tcctactttc gtataagtcg   1080
ttaagtgtgt aacaatctgt ccattcttta tcgtaccgta ttcttttaca atagccaccg   1140
tacaaagtac aattggtagc gtacttctgc atattcgttt ctgtgttatc caaagaccgt   1200
gattttattt ctagaacaat tgattcactg gggtcaatcc attcggcagg tattttttgag  1260 ccaaattcta aaattgaagc agggggagca acttcggagg ttcttttcca atgtcctctc   1320
gttttgcggt cgatttcttt gaattcttct tgagatatac cgtttgcgat agaacagaat   1380
gaaagtattt ttttcaccct tcttcttgaa ttttgtatgt gttttcttg gcttgagtgg    1440 tctacaattt cagaggagtc tccttggtgc tttttatact cttcttcatc tagcacaagt   1500
aaccctagca taaagaatc tttttttccca gaatctctgc ctattactat taagtctaaa   1560
ttctctccaa attcctccaa atattcaggt tttaccttga tccagttgtt gtttcgactg   1620
gcgacattat aacttgaatt ataatatttc aaaacaactc cttctgaacc cagtgagatt   1680
gcaacttcta aagacttttt gattgactcc acaccataac atctagaaga tcgtactatt   1740
tctacaatat ttttcaaggg acttaaaatg ctgttcagat attgcttcct ttgatgaagg   1800
ggtaatggtg tcaacgaagt cccattcagg tataacagat caaacaccat atataagggg   1860
tgaaagtcaa cattatttat actattaaaa gatagcgctt cctttgcact tcctttaaca   1920
agaccgaatg gaagaatcac ccgtctttt gcatcaaacg tcaccatttc tccatctaaa    1980
acacattctt taacactatc tgtaaacctc aaatgttgag atatagttcc tgatgataag   2040
ctcgctccgt acaaataggt atagtcgatg ccccgtctac taaaaatttt tatggattca   2100
ccataattca tataatgaac ttgaattcgt tctccatcca ttttttcttc taccaaaaaa   2160
tcatcatgta gtgtacggca tattttctca taagaaagat tcactttttt ggctaattgg   2220
ggggcgaatg caaagccaac ttttatactc aaatcatcat cctttagacg aacttttgga   2280
tcataaagtt ttgaagttac cacctttaaa tcagatatca cgctaagata atcctgagca   2340
tcaggatgcc agcagtttag caatttgtgc tcttgacctc ctattactct attttaagc    2400
```

-continued

| | |
|---|---|
| acgatatcaa agaagtattt taattcgacg aaactcatat tctccacaca gtgcaggaaa | 2460 |
| ggtttggact tgacaagact cttaaatcct cgtccggaag cgaacctgtc tccactcaaa | 2520 |
| ctatccagat agtgattgac gttatcaatt gtaatcgctt ttgagctagg ttcagccctt | 2580 |
| cttttagcaa tttcttccac aagaagagaa gaaagattcc cacctttacc gacacgctgt | 2640 |
| ttccaatctt ttaaccgctg ctctgttgca gaattttttg gcaacttcaa gtaagagcat | 2700 |
| atagttctta ttaatacata atccttaata ttatagattc gtctatcgcg gtagggaaga | 2760 |
| gcaagaacca gtgcaggata tatattattt cccacggttt ttctccacat ttcgacgaaa | 2820 |
| ttcgatatta tttcatagta cttgaaagac cttgatttgc cagtgccggc cgttccatta | 2880 |
| atttgaactt catgtatctt cacaaatagc tcttcacaaa gccatttgaa atctggacta | 2940 |
| ggcgcaaagt tttggggctc gggtatagaa tctagtgctg atatcatacc taaataatcc | 3000 |
| gttactattt ccttcagttc tagattttta ttttagtatt tattttccac atattaacat | 3060 |
| atgtttaaag gattttttca tagttagatt tgtttaaaga tttaatatgg tgacaaaagg | 3120 |
| taaaagaga aaataacaa aaaaaggaa aaagaagaa aataagggat cgaaaacgat | 3180 |
| cttaactcta gtactgcaca aacaacgtaa gtgatgaaac cgatattatt gatctatact | 3240 |
| cggcgaatct tacgatttat atcacaatgt tacatgtaca acgtacgtag ttactaaaca | 3300 |
| ctgatttcag cctatttaat cac | 3323 |

<210> SEQ ID NO 6
<211> LENGTH: 3323
<212> TYPE: DNA
<213> ORGANISM: Saccharomyces cerevisiae

<400> SEQUENCE: 6

| | |
|---|---|
| gtgattaaat aggctgaaat cagtgtttag taactacgta cgttgtacat gtaacattgt | 60 |
| gatataaatc gtaagattcg ccgagtatag atcaataata tcggtttcat cacttacgtt | 120 |
| gtttgtgcag tactagagtt aagatcgttt tcgatcccct attttcttct tttttccttt | 180 |
| tttttgttat ttttctcttt ttaccttttg tcaccatatt aaatctttaa acaaatctaa | 240 |
| ctatgaaaaa atcctttaaa catatgttaa tatgtggaaa ataaatacta aataaaaat | 300 |
| ctagaactga aggaaatagt aacggattat ttaggtatga tatcagcact agattctata | 360 |
| cccgagcccc aaaactttgc gcctagtcca gatttcaaat ggctttgtga agagctattt | 420 |
| gtgaagatac atgaagttca aattaatgga acggccggca ctggcaaatc aaggtctttc | 480 |
| aagtactatg aaataatatc gaatttcgtc gaaatgtgga gaaaaccgt gggaaataat | 540 |
| atatatcctg cactggttct tgctcttccc taccgcgata gacgaatcta taatattaag | 600 |
| gattatgtat taataagaac tatatgctct tacttgaagt tgccaaaaaa ttctgcaaca | 660 |
| gagcagcgt taaagattg gaaacagcgt gtcggtaaag gtgggaatct ttcttctctt | 720 |
| cttgtggaag aaattgctaa aagaagggct gaacctagct caaaagcgat tacaattgat | 780 |
| aacgtcaatc actatctgga tagtttgagt ggagacaggt tcgcttccgg acgaggattt | 840 |
| aagagtcttg tcaagtccaa accttttcctg cactgtgtgg agaatatgag tttcgtcgaa | 900 |
| ttaaaatact tctttgatat cgtgcttaaa aatagagtaa taggaggtca agagcacaaa | 960 |
| ttgctaaact gctggcatcc tgatgctcag gattatctta gcgtgatatc tgatttaaag | 1020 |
| gtggtaactt caaaacttta tgatccaaaa gttcgtctaa aggatgatga tttgagtata | 1080 |
| aaagttggct ttgcattcgc cccccaatta gccaaaaaag tgaatctttc ttatgagaaa | 1140 |
| atatgccgta cactacatga tgattttttg gtagaagaaa aaatggatgg agaacgaatt | 1200 |

-continued

```
caagttcatt atatgaatta tggtgaatcc ataaaatttt ttagtagacg gggcatcgac    1260
tataccactt tgtacggagc gagcttatca tcaggaacta tatctcaaca tttgaggttt    1320
acagatagtg ttaaagaatg tgttttagat ggagaaatgg tgacgtttga tgcaaaaaga    1380
cgggtgattc ttccattcgg tcttgttaaa ggaagtgcaa aggaagcgct atcttttaat    1440
agtataaata atgttgactt tcacccctta tatggtgt ttgatctgtt atacctgaat      1500
gggacttcgt tgacaccatt accccttcat caaaggaagc aatatctgaa cagcatttta    1560
agtcccttga aaatattgt agaaatagta cgatcttcta gatgttatgg tgtggagtca     1620 atcaaaagt ctttagaagt tgcaatctca ctgggttcag aaggagttgt tttgaaatat     1680
tataattcaa gttataatgt cgccagtcga acaacaact ggatcaaggt aaaacctgaa     1740
tatttggagg aatttggaga gaatttagac ttaatagtaa taggcagaga ttctgggaaa    1800
aaagattctt ttatgctagg gttacttgtg ctagatgaag aagagtataa aaagcaccaa    1860
ggagactcct ctgaaattgt agaccactca agccaagaaa acacataca aaattcaaga     1920 agaagggtga aaaaaatact ttcattctgt tctatcgcaa acggtatatc tcaagaagaa    1980
ttcaaagaaa tcgaccgcaa aacgagagga cattggaaaa gaacctccga agttgctccc    2040
cctgcttcaa ttttagaatt tggctcaaaa atacctgccg aatggattga ccccagtgaa    2100
tcaattgttc tagaaataaa atcacggtct ttggataaca cagaaacgaa tatgcagaag    2160
tacgctacca attgtacttt gtacggtggc tattgtaaaa gaatacggta cgataaagaa    2220
tggacagatt gttacacact taacgactta tacgaaagta ggacggttaa atctaacccc    2280
agctatcaag cggaaaggtc acagcttgga ttgatacgga aaaagagaaa gagagtactt    2340
atttcagaca gctttcacca aaacaggaaa caactgccaa tttcaaacat ctttgccgga    2400
ttactttttt atgttctctc tgactatgtc acggaggaca ctggaatacg gattacacgg    2460
gcagaacttg aaaaaactat tgtggaacat ggtggtaaac tgatatataa tgtaatttta    2520
aaacgtcatt caattgggga cgttcggtta atcagctgta aaactaccac ggaatgcaag    2580
gctttaatag atcgaggata tgatatattg cacccaaatt gggtactcga ttgtatagca    2640
tataagaggc tcatcctgat cgagcccaat tattgcttta acgtctctca aaaaatgaga    2700
gccgtcgctg aaaaaagggt agattgtttg ggtgatagtt ttgaaaatga catttcggaa    2760
accaaactgt catcattgta taaatcacaa ctaagtctac caccgatggg ggaactcgag    2820
atagattctg aggttcggcg gtttccatta tttttattct ccaacaggat tgcatacgta    2880
ccacgtcgca aaattagcac agaagatgac attatagaaa tgaaaattaa gttgtttggt    2940
ggaaaaataa cagatcaaca gtcactttgt aacttaataa ttataccata tactgatcct    3000
attttgagga aagactgcat gaatgaggta cacgaaaaaa taaaagaaca aataaaggct    3060
tctgatacta taccgaaaat agccagggtc gttgccccctg aatgggtgga tcattctatt    3120
aatgaaaact gtcaagtgcc tgaagaagac ttccccgtag tcaactactg atggtgcgtt    3180
ttgcggaggc ttaattttt gaagtttatt taatactatc ctacatatgt acattaaata     3240
cttccgtaac gtttatcaat aagagtggaa gatgcgcaat tatattcaaa agattggcca    3300
gtcaattaac ttaaggaaaa aat                                            3323
```

<210> SEQ ID NO 7
<211> LENGTH: 5
<212> TYPE: PRT
<213> ORGANISM: Saccharomyces cerevisiae

```
<400> SEQUENCE: 7

Ala Glu Ile Ser Val
1               5

<210> SEQ ID NO 8
<211> LENGTH: 6
<212> TYPE: PRT
<213> ORGANISM: Saccharomyces cerevisiae

<400> SEQUENCE: 8

Leu Arg Thr Leu Tyr Met
1               5

<210> SEQ ID NO 9
<211> LENGTH: 11
<212> TYPE: PRT
<213> ORGANISM: Saccharomyces cerevisiae

<400> SEQUENCE: 9

His Cys Asp Ile Asn Arg Lys Ile Arg Arg Val
1               5                   10

<210> SEQ ID NO 10
<211> LENGTH: 43
<212> TYPE: PRT
<213> ORGANISM: Saccharomyces cerevisiae

<400> SEQUENCE: 10

Ile Asn Asn Ile Gly Phe Ile Thr Tyr Val Val Cys Ala Val Leu Glu
1               5                   10                  15

Leu Arg Ser Phe Ser Ile Pro Tyr Phe Leu Leu Phe Ser Phe Phe Leu
            20                  25                  30

Leu Phe Phe Ser Phe Tyr Leu Leu Ser Pro Tyr
        35                  40

<210> SEQ ID NO 11
<211> LENGTH: 5
<212> TYPE: PRT
<213> ORGANISM: Saccharomyces cerevisiae

<400> SEQUENCE: 11

Ile Phe Lys Gln Ile
1               5

<210> SEQ ID NO 12
<211> LENGTH: 7
<212> TYPE: PRT
<213> ORGANISM: Saccharomyces cerevisiae

<400> SEQUENCE: 12

Lys Asn Pro Leu Asn Ile Cys
1               5

<210> SEQ ID NO 13
<211> LENGTH: 6
<212> TYPE: PRT
<213> ORGANISM: Saccharomyces cerevisiae

<400> SEQUENCE: 13

Tyr Val Glu Asn Lys Tyr
1               5

<210> SEQ ID NO 14
```

<211> LENGTH: 959
<212> TYPE: PRT
<213> ORGANISM: Saccharomyces cerevisiae

<400> SEQUENCE: 14

```
Asn Lys Asn Leu Glu Leu Lys Glu Ile Val Thr Asp Tyr Leu Gly Met
 1               5                  10                  15

Ile Ser Ala Leu Asp Ser Ile Pro Glu Pro Gln Asn Phe Ala Pro Ser
            20                  25                  30

Pro Asp Phe Lys Trp Leu Cys Glu Glu Leu Phe Val Lys Ile His Glu
        35                  40                  45

Val Gln Ile Asn Gly Thr Ala Gly Thr Gly Lys Ser Arg Ser Phe Lys
    50                  55                  60

Tyr Tyr Glu Ile Ile Ser Asn Phe Val Glu Met Trp Arg Lys Thr Val
65                  70                  75                  80

Gly Asn Asn Ile Tyr Pro Ala Leu Val Leu Ala Leu Pro Tyr Arg Asp
                85                  90                  95

Arg Arg Ile Tyr Asn Ile Lys Asp Tyr Val Leu Ile Arg Thr Ile Cys
            100                 105                 110

Ser Tyr Leu Lys Leu Pro Lys Asn Ser Ala Thr Glu Gln Arg Leu Lys
        115                 120                 125

Asp Trp Lys Gln Arg Val Gly Lys Gly Gly Asn Leu Ser Ser Leu Leu
    130                 135                 140

Val Glu Glu Ile Ala Lys Arg Arg Ala Glu Pro Ser Ser Lys Ala Ile
145                 150                 155                 160

Thr Ile Asp Asn Val Asn His Tyr Leu Asp Ser Leu Ser Gly Asp Arg
                165                 170                 175

Phe Ala Ser Gly Arg Gly Phe Lys Ser Leu Val Lys Ser Lys Pro Phe
            180                 185                 190

Leu His Cys Val Glu Asn Met Ser Phe Val Glu Leu Lys Tyr Phe Phe
        195                 200                 205

Asp Ile Val Leu Lys Asn Arg Val Ile Gly Gly Gln Glu His Lys Leu
    210                 215                 220

Leu Asn Cys Trp His Pro Asp Ala Gln Asp Tyr Leu Ser Val Ile Ser
225                 230                 235                 240

Asp Leu Lys Val Val Thr Ser Lys Leu Tyr Asp Pro Lys Val Arg Leu
                245                 250                 255

Lys Asp Asp Asp Leu Ser Ile Lys Val Gly Phe Ala Phe Ala Pro Gln
            260                 265                 270

Leu Ala Lys Lys Val Asn Leu Ser Tyr Glu Lys Ile Cys Arg Thr Leu
        275                 280                 285

His Asp Asp Phe Leu Val Glu Glu Lys Met Asp Gly Glu Arg Ile Gln
    290                 295                 300

Val His Tyr Met Asn Tyr Gly Glu Ser Ile Lys Phe Ser Arg Arg
305                 310                 315                 320

Gly Ile Asp Tyr Thr Tyr Leu Tyr Gly Ala Ser Leu Ser Ser Gly Thr
                325                 330                 335

Ile Ser Gln His Leu Arg Phe Thr Asp Ser Val Lys Glu Cys Val Leu
            340                 345                 350

Asp Gly Glu Met Val Thr Phe Asp Ala Lys Arg Arg Val Ile Leu Pro
        355                 360                 365

Phe Gly Leu Val Lys Gly Ser Ala Lys Glu Ala Leu Ser Phe Asn Ser
    370                 375                 380

Ile Asn Asn Val Asp Phe His Pro Leu Tyr Met Val Phe Asp Leu Leu
```

-continued

```
            385                 390                 395                 400

Tyr Leu Asn Gly Thr Ser Leu Thr Pro Leu Pro Leu His Gln Arg Lys
                405                 410                 415

Gln Tyr Leu Asn Ser Ile Leu Ser Pro Leu Lys Asn Ile Val Glu Ile
                420                 425                 430

Val Arg Ser Ser Arg Cys Tyr Gly Val Glu Ser Ile Lys Lys Ser Leu
                435                 440                 445

Glu Val Ala Ile Ser Leu Gly Ser Glu Gly Val Val Leu Lys Tyr Tyr
                450                 455                 460

Asn Ser Ser Tyr Asn Val Ala Ser Arg Asn Asn Asn Trp Ile Lys Val
465                 470                 475                 480

Lys Pro Glu Tyr Leu Glu Glu Phe Gly Glu Asn Leu Asp Leu Ile Val
                485                 490                 495

Ile Gly Arg Asp Ser Gly Lys Lys Asp Ser Phe Met Leu Gly Leu Leu
                500                 505                 510

Val Leu Asp Glu Glu Tyr Lys Lys His Gln Gly Asp Ser Ser Glu
                515                 520                 525

Ile Val Asp His Ser Ser Gln Glu Lys His Ile Gln Asn Ser Arg Arg
                530                 535                 540

Arg Val Lys Lys Ile Leu Ser Phe Cys Ser Ile Ala Asn Gly Ile Ser
545                 550                 555                 560

Gln Glu Glu Phe Lys Glu Ile Asp Arg Lys Thr Arg Gly His Trp Lys
                565                 570                 575

Arg Thr Ser Glu Val Ala Pro Pro Ala Ser Ile Leu Glu Phe Gly Ser
                580                 585                 590

Lys Ile Pro Ala Glu Trp Ile Asp Pro Ser Glu Ser Ile Val Leu Glu
                595                 600                 605

Ile Lys Ser Arg Ser Leu Asp Asn Thr Glu Thr Asn Met Gln Lys Tyr
                610                 615                 620

Ala Thr Asn Cys Thr Leu Tyr Gly Gly Tyr Cys Lys Arg Ile Arg Tyr
625                 630                 635                 640

Asp Lys Glu Trp Thr Asp Cys Tyr Thr Leu Asn Asp Leu Tyr Glu Ser
                645                 650                 655

Arg Thr Val Lys Ser Asn Pro Ser Tyr Gln Ala Glu Arg Ser Gln Leu
                660                 665                 670

Gly Leu Ile Arg Lys Lys Arg Lys Val Leu Ile Ser Asp Ser Phe
                675                 680                 685

His Gln Asn Arg Lys Gln Leu Pro Ile Ser Asn Ile Phe Ala Gly Leu
                690                 695                 700

Leu Phe Tyr Val Leu Ser Asp Tyr Val Thr Glu Asp Thr Gly Ile Arg
705                 710                 715                 720

Ile Thr Arg Ala Glu Leu Glu Lys Thr Ile Val Glu His Gly Gly Lys
                725                 730                 735

Leu Ile Tyr Asn Val Ile Leu Lys Arg His Ser Ile Gly Asp Val Arg
                740                 745                 750

Leu Ile Ser Cys Lys Thr Thr Thr Glu Cys Lys Ala Leu Ile Asp Arg
                755                 760                 765

Gly Tyr Asp Ile Leu His Pro Asn Trp Val Leu Asp Cys Ile Ala Tyr
                770                 775                 780

Lys Arg Leu Ile Leu Ile Glu Pro Asn Tyr Cys Phe Asn Val Ser Gln
785                 790                 795                 800

Lys Met Arg Ala Val Ala Glu Lys Arg Val Asp Cys Leu Gly Asp Ser
                805                 810                 815
```

```
Phe Glu Asn Asp Ile Ser Glu Thr Lys Leu Ser Ser Leu Tyr Lys Ser
        820                 825                 830

Gln Leu Ser Leu Pro Pro Met Gly Glu Leu Glu Ile Asp Ser Glu Val
        835                 840                 845

Arg Arg Phe Pro Leu Phe Leu Phe Ser Asn Arg Ile Ala Tyr Val Pro
        850                 855                 860

Arg Arg Lys Ile Ser Thr Glu Asp Asp Ile Ile Glu Met Lys Ile Lys
865                 870                 875                 880

Leu Phe Gly Gly Lys Ile Thr Asp Gln Gln Ser Leu Cys Asn Leu Ile
            885                 890                 895

Ile Ile Pro Tyr Thr Asp Pro Ile Leu Arg Lys Asp Cys Met Asn Glu
            900                 905                 910

Val His Glu Lys Ile Lys Glu Gln Ile Lys Ala Ser Asp Thr Ile Pro
            915                 920                 925

Lys Ile Ala Arg Val Val Ala Pro Glu Trp Val Asp His Ser Ile Asn
        930                 935                 940

Glu Asn Cys Gln Val Pro Glu Glu Asp Phe Pro Val Val Asn Tyr
945                 950                 955

<210> SEQ ID NO 15
<211> LENGTH: 13
<212> TYPE: PRT
<213> ORGANISM: Saccharomyces cerevisiae

<400> SEQUENCE: 15

Trp Cys Val Leu Arg Arg Leu Asn Phe Leu Lys Phe Ile
  1               5                  10

<210> SEQ ID NO 16
<211> LENGTH: 7
<212> TYPE: PRT
<213> ORGANISM: Saccharomyces cerevisiae

<400> SEQUENCE: 16

Tyr Tyr Pro Thr Tyr Val His
  1               5

<210> SEQ ID NO 17
<211> LENGTH: 19
<212> TYPE: PRT
<213> ORGANISM: Saccharomyces cerevisiae

<400> SEQUENCE: 17

Arg Leu Ser Ile Arg Val Glu Asp Ala Gln Leu Tyr Ser Lys Asp Trp
  1               5                  10                  15

Pro Val Asn

<210> SEQ ID NO 18
<211> LENGTH: 4
<212> TYPE: PRT
<213> ORGANISM: Saccharomyces cerevisiae

<400> SEQUENCE: 18

Leu Lys Glu Lys
  1
```